US008551489B2

(12) United States Patent
Moussa et al.

(10) Patent No.: US 8,551,489 B2
(45) Date of Patent: Oct. 8, 2013

(54) METHODS FOR THE TREATMENT OF CANCERS

(75) Inventors: Omar Moussa, Charleston, SC (US); Dennis K. Watson, Charleston, SC (US); Perry V. Halushka, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 239 days.

(21) Appl. No.: 12/811,321

(22) PCT Filed: Jan. 2, 2009

(86) PCT No.: PCT/US2009/030025
§ 371 (c)(1),
(2), (4) Date: Jan. 3, 2011

(87) PCT Pub. No.: WO2009/089098
PCT Pub. Date: Jul. 16, 2009

(65) Prior Publication Data
US 2011/0117078 A1    May 19, 2011

Related U.S. Application Data

(60) Provisional application No. 61/018,784, filed on Jan. 3, 2008.

(51) Int. Cl.
| A61P 35/00 | (2006.01) |
| A61K 38/00 | (2006.01) |
| A61K 39/00 | (2006.01) |
| C12Q 1/68  | (2006.01) |
| G01N 33/53 | (2006.01) |

(52) U.S. Cl.
USPC .... 424/174.1; 514/764; 514/19.3; 424/130.1; 435/6.1; 435/6.14; 435/7.1

(58) Field of Classification Search
None
See application file for complete search history.

(56) References Cited

U.S. PATENT DOCUMENTS

| 4,243,671 | A  | 1/1981  | Harris et al.     |
| 5,021,448 | A  | 6/1991  | Piraino et al.    |
| 5,091,191 | A  | 2/1992  | Oda et al.        |
| 5,128,359 | A  | 7/1992  | Bru-Magniez et al.|
| 5,158,967 | A  | 10/1992 | Hall              |
| 5,280,034 | A  | 1/1994  | Hall et al.       |
| 5,597,848 | A  | 1/1997  | Ito et al.        |
| 5,618,941 | A  | 4/1997  | Dickinson et al.  |
| 2002/0016342 | A1 | 2/2002 | Scolnick et al.   |
| 2006/0217431 | A1 | 9/2006 | Daemmgen          |
| 2006/0228299 | A1 | 10/2006 | Thorpe et al.    |

OTHER PUBLICATIONS

Casey et al., "Expression of cyclooxygenase-2 and thromboxane synthase in non-neoplastic and neoplastic thyroid lesions," *Endocr. Pathol.*, 15:107-1 16, 2004.
Finnerty et al., "Effect of GR32191, a potent thromboxane receptor antagonist, on exercise induced bronchoconstriction in asthma," *Thorax*, 46:190-192, 1991.
Fitzgerald et al., "Thromboxane A2 biosynthesis in human disease," *Fed. Proc.*, 46:154-158, 1987.
Fujimura et al., "Up-regulation of ICH-II protein by thromboxane A2 antagonists enhances cisplatin-induced apoptosis in non-small-cell lung-cancer cell lines," *J. Cancer Res. Clin. Oncol.*, 125(7): 389-394, 1999.
Halushka et al., "Thromboxane A2 receptors: where have you gone?" *Prostaglandins Other Lipid Mediators*, 60:175-189, 2000.
Halushka et al., "Thromboxane, prostaglandin and leukotriene receptors," *Annu. Rev. Pharmacol., Toxicol.*, 29:213-239, 1989.
Halushka et al., In: *Handbook of Experimental Pharmacology, Platelets and Their Factors*, Von Bruchhusen and Walter (Eds.), Springer-Verlag, Berlin, Germany, vol. 126:459-482, 1997.
Humphrey et al., "Pathophysiological actions of Thromboxane A2 and their pharmacological antagonism by thromboxane receptor blockade with GR32191," *Circulation*, 81, 142-152; 159-160, 1990.
Jariyawat et al., "Thromboxane A2 mediates cisplatin-induced apoptosis of renal tubule cells," *IUBMB Life*, 42: 113-121, 1997.
Kasahara et al., "Modulation of sensitivity to cis-diamminedichloroplatinum (II) by thromboxane A2 receptor antagonists in non-small-cell lung cancer cell lines," *Br. J. Cancer*, 74(10):1553-1558, 1996.
Miggin and Kinsella, "Expression and tissue distribution of the mRNAs encoding the human thromboxane A2 receptor (TP) α and β isoforms," *Biochim. Biophys. Acta.*, 1425:543-559, 1998.
Moussa et al., "Prognostic and Functional Significance of Thromboxane Synthase Gene Overexpression in Invasive Bladder Cancer ," *Cancer Res.*, 65:11581-11587, 2005.
Moussa et al., "Inhibition of thromboxane synthase activity modulates bladder cancer cell responses to chemotherapeutic agents," *Oncogene*, 27:55-62, 2007. [published online Jul. 2, 2007.]
Nie et al., "Differential expression of thromboxanes synthase in prostate carcinoma," *Am J Pathol.*, 164(2):429-439, 2004.
Onguru et al., "Analysis of Cox-2 and thromboxane synthase expression in pituitary adenomas and carcinomas ," *Endocr. Pathol.*, 15:17-27, 2004.
Parent et al., "Internalization of the TXA2 Receptor α and β Isoforms: role of the differentially spliced cooh terminus in agonist-promoted receptor internalization," *The Journal of Biological Chemistry*, 274:8941-8948, 1999.
Parent et al., "Role of the Differentially Spliced Carboxyl Terminus in Thromboxane A2 Receptor Trafficking: identification of a distinct motif for tonic internalization," *The Journal of Biological Chemistry*, 276:7079-7085, 2001.
Rochdi et al., "Nm23-H2 interacts with a G protein-coupled receptor to regulate Its endocytosis through an RacI-dependent mechanism," *The Journal of Biological Chemistry*, 279:18981-18989, 2004.
Theriault et al., "Role of the RabI I-Associated Intracellular Pool of Receptors Formed by Constitutive Endocytosis of the β Isoform of the Thromboxane A2 Receptor (TPβ)," *Biochemistry*, 2004:43(19): 5600-5607, 2004.
Thomas and Lumley, "Preliminary assessment of a novel thromboxane A2 receptor-blocking drug, GR32191, in healthy subjects," *Circulation*, 81(1 Suppl):153-8; discussion 159-60, 1990.
Yoshimoto et al., "Characterization of the prostaglandin biosynthetic pathway in non-small cell lung cancer: a comparison with small cell lung cancer and correlation with angiogenesis, angiogenic factors and metastases," *Oncology Reports*, 13:1049-1057, 2005.

*Primary Examiner* — Christine J Saoud
*Assistant Examiner* — Jon M Lockard
(74) *Attorney, Agent, or Firm* — Parker Highlander PLLC

(57) ABSTRACT

Methods for the treatment of cancers involving dysregulation of thromboxane receptor β (TP-β) are provided, including in certain aspects methods for diagnosing such cancers. Specific cancers included are genitourinary cancers, gastrointestinal cancers and leukemias.

16 Claims, 6 Drawing Sheets

METHODS FOR THE TREATMENT OF CANCERS

The present application is a national phase application under 35 U.S.C. §371 of International Patent Application No. PCT/US2009/030025 filed Jan. 2, 2009 which claims benefit of priority to U.S. Provisional Application Ser. No. 61/018,784, filed Jan. 3, 2008, the entire contents of which are hereby incorporated by reference.

This invention was made with government support under grant no. CA106570 awarded by the National Cancer Institute and grant no. 42153MK-GC-3532/N66001-03 awarded by the Department of Defense. The government has certain rights in the invention.

BACKGROUND OF THE INVENTION

I. Field of the Invention

The invention relates to the fields of molecular and cellular biology and oncology, and particularly to the treatment of cancers that involve the overexpression of thromboxane receptor β.

II. Related Art

Bladder cancer is the fifth most common cancer in the United States accounting for about 4.6% of all cases (Jemal et al., 2007). Most incidences of bladder cancer are superficial and localized in character with about 74% of all cases being localized when diagnosed (Jemal et al., 2007). It exists in two main forms, non-invasive which lacks invasion into surrounding muscle tissue and is the more common form accounting for 75% of all cases and muscle invasive in which it spreads into surrounding urinary areas and may metastasize (Sengupta and Blute, 2006).

The inventors have previously found that thromboxane synthase was over-expressed in patients with bladder cancer and was associated with a significantly poorer prognosis (Moussa et al., 2005). Thromboxane synthase catalyzes the formation of thromboxane $A_2$ from prostaglandin $H_2$, which is derived from the precursor arachidonic acid (Needleman et al., 1976). Thromboxane $A_2$, although very labile, stimulates it receptors to produce a myriad of pharmacologic events (Halushka et al., 1989; Halushka et al., 1997; Halushka, 2000). Thromboxane $A_2$ (TP) receptors are G protein coupled receptors (GPCR) and are expressed as two different isoforms, TP-α (Hirata et al., 1991) and TP-β (Raychowdhury et al., 1994), and arise by alternative mRNA splicing (Miggin and Kinsella, 1998). Stimulation of TP receptors is associated with a mitogenic response (Nagata et al., 1992). The isoforms share both common and different intracellular signaling mechanisms and different trafficking patterns. Both isoforms signal through $G\alpha_q$ resulting in transient increases in intracellular calcium and IP3 formation and through $G\alpha_{12}$ to stimulate sodium-hydrogen exchange (Halushka, 2000; Becker et al., 1999; Shenker et al., 1991). When stimulated by ligand, TP-β, but not TP-α, couples to Gαi which decreases cAMP production (Hirata et al., 1994; Hirata et al., 1996). Stimulation of both receptors results in phosphorylation of ERK and FAK (Miggin and Kinsella, 2002; Gao et al., 2001). Nonetheless, the role of TP receptors in bladder cancer remains unclear.

SUMMARY OF THE INVENTION

In one non-limiting aspect there is disclosed a method of treating cancer in a subject. The method can include (a) assessing thromboxane receptor β (TP-β) expression in a cancer cell or other sample from said subject; and (b) administering to said subject a TP-β antagonist and/or a thromboxane synthase (TXAS) inhibitor if TP-β expression in said cancer cell or other sample is elevated as compared to an appropriate control cell or sample. Examples of cancer cells include a lung cancer cell, a bladder cancer cell, a prostate cancer cell, a kidney cancer cell, a colon cancer cell, a stomach cancer cell, a pancreatic cancer cell or a hematopoietic cancer cell. Other sources of cells which can be assayed are white cells, brain, thymus, heart, kidney, liver, lung, endothelial cells, placenta, uterus, prostate, thyroid, normal bladder or bone marrow. In particular, the other sample may be blood or urine. In certain aspects, step (b) can include administering said TP-β antagonist. Non-limiting examples of TP-β antagonists that can be used in the context of the present invention include GR32191, SQ29548, sulotroban, daltroban, Z-335, LCB-2853 (CAS141335-11-7) SQ28668, ICI 192605, AH 23848, ONO3708, pinane $TXA_2$ or ifetroban, or derivatives or analogues thereof. In particular embodiments, step (b) includes administering said TXAS inhibitor. Non-limiting examples of TXAS inhibitors that can be used in the context of the present invention include dazoxiben, furegulate, ozagrel, OKY1581 or CGS-12970, or derivatives or analogues thereof. In another aspect, step (b) can include administering both said TP-β antagonist and said TXAS inhibitor or compounds that have both actions as TP receptor antagonist and TXAS inhibitor within a single molecular entity. Step (a), in certain embodiments, can include using immunohistochemistry, ELISA, RIA, or Western blot techniques. The method can also include assessing TP-β expression from said control cell or sample. The control cell can be a non-cancer cell obtained from said subject. The method can include administering said TP-β antagonist or said TXAS inhibitor more than once (e.g., 1, 2, 3, 4, 5, 6, 7, 8, 9, 10, or more, etc.). In one aspect, the method also includes administering to said subject a second anti-cancer therapy. Non-limiting examples of said second anti-cancer therapy include chemotherapy, radiotherapy, toxin therapy, gene therapy, surgery, targeted therapy using small molecules or immunotherapy. The method can include administering said second anti-cancer therapy more than once (e.g., 1, 2, 3, 4, 5, 6, 7, 8, 9, 10, or more, etc.). Non-limiting examples of cancer include recurrent, metastatic or multi-drug resistant cancer. The subject can be a human or a non-human mammal. Non-limiting examples of non-human animals include a monkey, a dog, a cat, a rabbit, a rat, a mouse, a goat, a sheep, a horse or a cow. The method can include obtaining said cancer cell from said subject. In certain embodiments, administering includes intravenous, intra-arterial, subcutaneous, intratumoral, oral, topical, intraperitoneal or aerosol delivery.

In another aspect, there is disclosed a method of treating cancer in a subject, which comprises administering to said subject a TP-β antagonist, wherein cancer cells in said subject exhibit elevated TP-β expression as compared to an appropriate control cell. In a further embodiment, the cancer cells of said subject may not exhibit elevated TP-α expression as compared to appropriate control cells. The cancer may be a solid tumor. In a further embodiment, the cancer is renal cell carcinoma, prostate, breast, colorectal, bladder, stomach, kidney, pancreatic or lung cancer. In yet a further embodiment, the cancer is renal cell carcinoma, prostate, breast, colorectal or bladder cancer. In another embodiment, the cancer is a genitourinary cancer, gastrointestinal cancer or hematopoietic cancer. In one aspect, the method also includes administering to said subject a second anti-cancer therapy. Non-limiting examples of said second anti-cancer therapy include chemotherapy, radiotherapy, toxin therapy, gene therapy, surgery, targeted therapy using small molecules or immunotherapy. The method can include administering said second anti-cancer therapy more than once (e.g., 1, 2, 3, 4, 5, 6, 7, 8, 9, 10, or more, etc.). Non-limiting examples of cancer include recurrent, metastatic or multi-drug resistant cancer. The subject can be a human or a non-human mammal. Non-limiting examples of non-human animals include a monkey, a dog, a cat, a rabbit, a rat, a mouse, a goat, a sheep, a horse or a cow. In certain embodiments, administering includes intravenous, intra-arterial, subcutaneous, intratumoral, oral, topical, intraperitoneal or aerosol delivery. In another embodiment, the TP-β antagonist that can be used include GR32191, SQ29548, sulotroban, daltroban, Z-335, LCB-2853 (CAS141335-11-7) SQ28668, ICI 192605, AH 23848, ONO3708, pinane $TXA_2$ or ifetroban, or derivatives or analogues thereof.

In yet another embodiment, there is disclosed a method of treating a genitourinary (GU) cancer in a subject comprising administering to said subject (a) a thromboxane receptor β (TP-β) antagonist and/or a thromboxane synthase (TXAS) inhibitor and (b) a second anti-cancer therapy, wherein cancer cells in said subject exhibit elevated TP-β expression as compared to an appropriate control cell. Non-limiting examples of GU cancer include bladder cancer, prostate cancer, urethral cancer or kidney cancer. In certain aspects, step (a) includes administering said TP-β antagonist. Non-limiting examples of TP-β antagonists that can be used in the context of the present invention include GR32191, SQ29548, sulotroban, daltroban, Z-335, LCB-2853 (CAS141335-11-7) SQ28668, ICI 192605, AH 23848, ONO3708, pinane $TXA_2$ or ifetroban, or derivatives or analogues thereof. Step (a) can also include administering said TXAS inhibitor. Non-limiting examples of TXAS inhibitors that can be used in the context of the present invention include dazoxiben, furegulate, ozagrel, OKY1581 or CGS-12970, or derivatives or analogues thereof. The method can further include administering said TP-β antagonist and/or said TXAS inhibitor or said second anti-cancer therapy more than once. Non-limiting examples of said second anti-cancer therapy is chemotherapy, radiotherapy, toxin therapy, gene therapy, surgery or immunotherapy. Non-limiting examples of cancers include recurrent, metastatic or multi-drug resistant cancers. Non-limiting examples of administering include intravenous, intra-arterial, subcutaneous, intratumoral, oral, topical or aerosol delivery.

Also disclosed is a method of treating a gastrointestinal (GI) cancer in a subject comprising administering to said subject (a) a thromboxane receptor β (TP-β) antagonist and/or a thromboxane synthase (TXAS) inhibitor and (b) a second anti-cancer therapy, wherein cancer cells in said subject exhibit elevated TP-β expression as compared to an appropriate control cell. Non-limiting examples of GI cancer include colon cancer, esophageal cancer, intestinal cancer (e.g., small intestinal cancer and GIST), stomach cancer or pancreatic cancer. Step (a) can include administering said TP-β antagonist. Non-limiting examples of TP-β antagonists that can be used in the context of the present invention include GR32191, SQ29548, sulotroban, daltroban, Z-335, LCB-2853 (CAS141335-11-7) SQ28668, ICI 192605, AH 23848, ONO3708, pinane $TXA_2$ or ifetroban, or derivatives or analogues thereof. Step (a) can include administering said TXAS inhibitor. Non-limiting examples of TXAS inhibitors that can be used in the context of the present invention include dazoxiben, furegulate, ozagrel, OKY1581 or CGS-12970, or derivatives or analogues thereof. The method can include administering said TPβ antagonist and/or said TXAS inhibitor or said second anti-cancer therapy more than once. Non-limiting examples of a second anti-cancer therapy include chemotherapy, radiotherapy, toxin therapy, gene therapy, surgery or immunotherapy. Non-limiting examples of cancer include recurrent, metastatic or multi-drug resistant cancer. Non-limiting examples of administrating include intramuscular, intravenous, intra-arterial, subcutaneous, intratumoral, oral, topical, intraperitoneal or aerosol delivery.

In another embodiment, there is disclosed a method of treating a hematopoietic cancer in a subject comprising administering to said subject (a) a thromboxane receptor β (TP-β) antagonist and/or a thromboxane synthase (TXAS) inhibitor and (b) a second anti-cancer therapy, wherein cancer cells in said subject exhibit elevated TP-β expression as compared to an appropriate control cell. Non-limiting examples of hematopoietic cancer or non-solid cancers include leukemia or lymphoma. Step (a) can include administering said TP-β antagonist. Non-limiting examples of TP-β antagonists that can be used in the context of the present invention include GR32191, SQ29548, sulotroban, daltroban, Z-335, LCB-2853 (CAS141335-11-7) SQ28668, ICI 192605, AH 23848, ONO3708, pinane $TXA_2$ or ifetroban, or derivatives or analogues thereof. Step (a) can include administering said TXAS inhibitor. Non-limiting examples of TXAS inhibitors that can be used in the context of the present invention include dazoxiben, furegulate, ozagrel, OKY1581 or CGS-12970, or derivatives or analogues thereof. The method can further include administering said TP-β antagonist and/or said TXAS inhibitor or said second anti-cancer therapy more than once. Non-limiting examples of second anti-cancer therapies include chemotherapy, radiotherapy, toxin therapy, gene therapy, surgery or immunotherapy. Non-limiting examples of cancer include recurrent, metastatic or multi-drug resistant cancers. Non-limiting examples of administration include intravenous, intra-arterial, subcutaneous, oral, topical or aerosol delivery.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The word "about" means plus or minus 5% of the stated number.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed.

(FIG. 1A) normal urothelium (X100); (FIG. 1B) Carcinoma in situ (X200); (FIG. 1C) invasive papillary carcinoma (X100) and (FIG. 1D) poorly differentiated, high grade carcinoma (X100). FIGS. 1A-D are from the same section.

(FIG. 4A) Representative immunoblot analysis of normal (N) and tumor (T) tissue for TP-α and TP-β. Tissues from 43 patients with bladder cancer were analyzed for the expression of TP-β by Western blotting. (FIG. 4B) Scatter-plot distribution of quantified TP-β receptor levels in bladder cancer tissues. The Western blots were scanned and quantitated. Protein levels are expressed as a fold increase over non-tumor bladder tissue. (FIG. 4C) Kaplan-Meier survival curve for patients with bladder cancer expressing either high (greater than 3-fold, n=28) or low levels (n=15) of TP-β. There was a statistically significant (p<0.005) difference in survival for the TP-β high versus TP-β low patients.

(FIG. 8A) Western blot analyses for expression of TP-α, TP-β, PCNA, and ICAM-1. GAPDH was used as a loading control. Data is representative of 3 experiments. Effect of transfection of TP-α and TP-β isoforms into SVHUC cells on proliferation (FIG. 8B) migration and invasion (FIG. 8C). Cell growth was determined using the MTT assay. The data are presented as the mean±SD for triplicate determinations. *Statistically significant (p<0.05) differences compared to control and TP-α (FIG. 8C) The cells were stimulated with U46619 (1 mM) and allowed to migrate or invade for 8 hrs or 24 hours, respectively, before being counted. The data are expressed as the mean±SD for 3 experiments conducted in triplicate. (FIG. 8D) Effect of different TP isoforms on SV-HUC cell transformation in vivo: SV-HUC stably transfected with TP-α, TP-β, or vector alone were injected subcutaneously into nude mice. Tumor growth was monitored over time. (Top) Summary table for tumor growth. (Bottom) Representative H&E staining for tumors derived from SV-HUC-TP-β injected mice.

(FIG. 9A) Anti-tumor effects of GR32191 and cisplatin treatment in immunocompromised mice. Subcutaneous TCC-SUP human bladder cancer xenografts in nude mice were treated with vehicle control (12 mice), GR32191 (15 mice), 5 mg/kg cisplatin (cisplatin high) (12 mice), 5 mg/kg cisplatin in combination with GR32191 (13 mice), or 0.5 mg/kg (single low dose cisplatin) alone (10 mice) or 0.5 mg/kg cisplatin in combination with GR32191 (10 mice). Tumor size was measured over time. Kaplan-Meier curves showing time to tumor onset across the treatment groups. (FIG. 9B) Pathological evaluation of tumors derived from mice treated with GR32191 (n=15) and vehicle control mice (n=12). Representative images of CD31 staining, TUNEL, staining, PCNA staining, and H&E staining are shown. Graphs on the left indicate the quantitative analysis for each of these markers. Five fields from 5 independent tumors (total 25) were counted and scored blindly. Statistically significant (p<0.05) differences compared to vehicle alone were indicated (++p<0.001 or +p<0.05).

(FIG. 11A) Northern blot analysis of different Gα protein mRNA in bladder cells. $G_\alpha 12$ mRNA is expressed at high levels in the majority of the bladder cell lines. (FIG. 11B) Western blot analysis showing $G_\alpha 12$ protein expression in T24 cells and knockdown using shRNAi specific for $G_\alpha 12$. (FIG. 11C) Knockdown of $G_\alpha 12$ resulted in reduction of TP agonist U46619 induced cell migration.

(FIG. 12A) Western blot analysis of β-arrestin in human bladder cancer tissues compared to matched non-tumor adjacent tissues. (FIG. 12B) Expression of β-arrestins in bladder cell lines. Bladder cancer cell lines express high levels of β-arrestin-2 and lower levels of β-arrestin-1 and no detectable levels of both in SVHUC cells (FIG. 12C) Western blot analysis showing specific knock down of β-arrestins-1 and -2 using isoform specific shRNA vectors. shRNA vector encoding no target (NT) was utilized as control. (FIG. 12D) Cells stably transfected with shRNA for β-arrestin-2 or shRNA vector with no target shRNA were treated for 12 hours with 1 μM U46619 and cell migration was measured by transwell migration assay. (*) indicates statistically significant differences compared to the control. (FIG. 12E) TP-β mediated increase in β-arrestin-2 measured by western blot analysis.

(FIG. 13A) Co-immunoprecipitation followed by Western blot analysis. Immunoprecipitation with TP-α or TP-β specific antibodies was performed using extracts prepared from HT-1376 cells. PH4 antibody (recognizes both TP isoforms) was used to demonstrate equal expression and IP of the TP receptors. Western blot demonstrated co-immunoprecipitation of TP-β but not TP-α with PTEN. (FIG. 13B) Increased association between TP-β and PTEN after receptor stimulation with U46619 agonist. Extracts prepared from solvent or agonist treated cells were immunoprecipitated with TP-β specific antibody. (FIG. 13C) Immunofluorescence studies demonstrate the co-localization of TP-β and PTEN. After TP-β stimulation with the U46619, PTEN translocated from the cytoplasm to the nuclear membrane. (FIG. 13D) PTEN lipid phosphatase activity was diminished in SV-HUC cells transfected with TP-β compared to those transfected with TP-α.

(FIG. 14A) Decreased PTN protein levels in T24 and TCCSUP cells transfected with TP-β-shRNAi and increased PTN protein in SV-HUC transfected with TP-β (FIG. 14B) Increased PTN mRNA in SV-HUC cells transfected with TP-β (FIG. 14C) Knockdown of TP-β resulted in reduction of PTN mRNA levels. (FIG. 14D) PTN mRNA reduction after PTXA2 treatment. The PTN mRNA levels are restored following the co-treatment with U46619. (FIG. 14E) shRNAi mediated knockdown of β-arrestin-2 reduced agonist dependent increase in PTN mRNA in HT-1376 cells (PTEN:wt), and UM-UC-3 cells (PTEN:minus). (FIG. 14F) Effect of U46619 on JNK1/2 and FOXO3a phosphorylation.

DETAILED DESCRIPTION OF THE INVENTION

Figure 1:
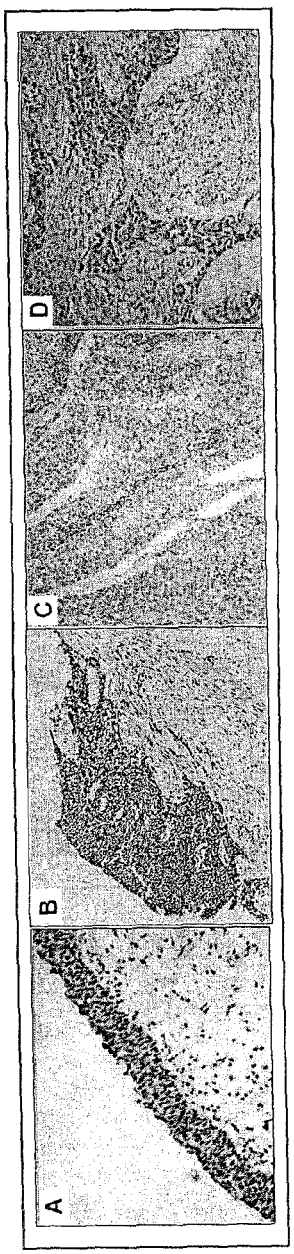
FIGS. 1A-D. TP receptor protein is over-expressed in bladder cancer. Immunohistochemical staining of TP receptor protein in human bladder tissue. Representative sections stained with rabbit anti-TP antibody (PH4) using Vectastain Elite ABC Kit.

The inventors previously showed that TP receptor protein was overexpressed in common types of bladder cancer (Moussa et al., 2005). They now show that it is in fact only the β isoform of the protein that has the link to bladder cancer. The overexpression of TP-β in bladder tumor identifies it as a marker of the disease and its potential importance in diagnosis and treatment. A survey of multiple bladder cancer cell lines revealed that TP-β receptors were highly expressed. In contrast to the immortalized normal bladder cell line, TP-α was either not expressed or present in lower levels in the bladder cancer cell lines.

Previous studies implicated a potential role of thromboxane $A_2$ in the pathogenesis of several different types of cancer. Specifically, thromboxane synthase was increased in these cancers and/or cell lines derived from them (Casey et al., 2004; Nie et al., 2004; Onguru et al., 2004; Yoshimoto et al., 2005). The inventors have previously found that thromboxane synthase is elevated in bladder cancer and carries a poor prognosis (Moussa et al., 2005) Inhibition of thromboxane $A_2$ synthesis results in a decrease in proliferation and migration (Moussa et al., 2005). These studies helped to establish a potential role for thromboxane $A_2$ in the cancer phenotype. The final step in the stimulation of the cell by thromboxane $A_2$ relies on the presence of TP receptors.

The transfection of the immortalized but non-transformed SV-HUC cell line with TP-β receptor recapitulated a potential cancer phenotype as demonstrated by an increased rate of proliferation, migration and invasion compared to both the control pcDNA3 and TP-α DNA transfected cells. The observation that TP-α did not have an increased rate of proliferation and migration compared to pcDNA3 demonstrates that the effect seen with TP-β is specific for this isoform and not a non-specific effect of transfection of a TP receptor or empty vector. Of greater significance was the observation that TP-β transfected SV-HUC cells formed tumors in nude mice.

Stimulation of T24 but not SV-HUC cells with U46619 was associated with an increased phosphorylation of ERK and FAK. Also, treatment with the TP receptor antagonist PTXA2 had no effect on phospho-ERK and phospho-FAK in the SV-HUC cells but significantly reduced these levels in the T24 cells. Collectively, these observations support the notion that the elevated expression of the TP-β receptor plays a role in the phenotype of bladder cancer cells.

The intracellular signaling pathways that mediate the cancer phenotype are uncertain. TP-α and TP-β receptors are G protein coupled, and couple to some of the same G proteins. TP-β but not TP-α has also been shown to interact with β-arrestins-1 and -2 (Theriault et al., 2004; Rochdi et al., 2004; Parent et al., 1999; Parent et al., 2001). Once thought to only enhance desensitization, β-arrestins have been shown to also act as scaffolding proteins and also to activate MAPK and phosphorylate ERK.

In further support of a role for β-arrestins in mediating the effects of TP-β are the observations of Buchanan et al. (2006), who found that β-arrestin-1 may play an important role in prostaglandin $E_2$ activation of Src and transactivation of EGFR in colorectal cancer cells. In addition, β-arrestin-1 was shown to enhance the metastatic potential of colorectal cancer cells in vivo (Buchanan et al., 2006). However, in contrast, the present inventors found that β-arrestin-2 and not β-arrestin-1 mediated TP-β induced migration. $G_α12$ also appears to play a role in TP-β-induced cell migration consistent with the previous observation of role for it in metastases (Chen et al., 2003; Kelley-Hickie and Kinsella, 2006). Thus, there are several intracellular signaling pathways unique to TP-β that could be responsible for the increased proliferation and migration seen in the bladder cancer cells and the SV-HUC cells transfected with TP-β. Further studies will be needed to sort out the critical intracellular signaling pathways responsible for the cancer phenotype. Of significant interest is the observation that there was a differential upregulation of only one of the two TP receptor isoforms. The mechanism(s) for this isoform specific upregulation are currently unknown. This is the first report of altered expression of a specific TP receptor isoform occurring in cancer cells and may represent the first report of this occurring with a GPCR.

The addition of GR32191 or SQ29548 to paclitaxel in vitro synergistically increased tumor cell death. Paclitaxel is a widely used anticancer drug with demonstrated activity in epithelial cell solid tumors including bladder cancers (Bokemeyer et al., 1998). Although paclitaxel is one of the most successfully used chemotherapeutic agents, the success rate for previously untreated bladder cancer patients is only 40-50%. Therefore, combination of paclitaxel and a TP receptor antagonist may improve efficacy. Cisplatin has been used as a chemotherapeutic agent for the treatment of bladder cancer (Calabro and Sternberg, 2002), but its use is associated with renal toxicity (Winston and Safirstein, 1985), and increased renal synthesis of thromboxane $A_2$ (Jariyawat et al., 1997; Blochl-Daum et al., 1995). Increased intra-renal synthesis of thromboxane $A_2$ has been shown to be associated with impaired function (Remuzzi et al., 1992; Fitzgerald et al., 1987). Thus, the use of a TP receptor antagonist as adjunctive therapy has the potential advantage of enhancing the chemotherapeutic effects of cisplatin, coupled with reducing the untoward side effects.

Previous studies have shown that TP receptor antagonist treatment increases $Na^+$, $K^+$-ATPase activity along with intracellular accumulation and sensitivity to cisplatin in non-small-cell lung cancer (Fitzgerald et al., 1987). Fujimura et al. (1999) found that TP receptor antagonists enhanced cisplatin induced apoptosis in lung cancer cell lines by up regulating ICH-1L (Fujimura et al., 1999). The results shown here further support the notion that TP receptor antagonists augment in vitro and in vivo responses to cisplatin.

Treatment with the TP receptor antagonist reduced cell proliferation in vitro and also increased the time of tumor onset and reduced the rate of tumor growth in vivo. Patients with the 3-fold or greater overexpression of TP-β in their tumor tissue had a significantly poorer prognosis. These results coupled with the cellular studies raise the possibility that the TP-β receptor could serve as a novel therapeutic target in bladder cancer. There have been previous clinical studies with the TP receptor antagonist GR32191 in healthy individuals (Thomas and Lumley, 1990) and in patients with asthma (Finnerty et al., 1991) or cardiovascular diseases (Humphrey et al., 1990) and was shown to be safe. Not only could the TP-β receptor be a therapeutic target, but its presence and/or over-expression could be used as a predictor of prognosis and dictate therapy.

PTEN, a tumor suppressor, was found to coimmuoprecipitate with TP-β, and interaction was enhanced in the presence of agonist. TP-β co-localized with PTEN in the cytoplasm and in the presence of U46619, the TP-β and PTEN proteins translocated to the nuclear membrane. One of the downstream molecules regulated by PTEN is Pleiotrophin (PTN). The inventors' preliminary cDNA microarray analyses indicated that PTN mRNA levels was increased following TP-β expression. Subsequent loss of function (TP-β-shRNAi) and gain of function (TP-β-expression) studies support the model that PTN mRNA and protein are regulated by TP-β expression. Agonist-dependent PTN mRNA increase was dependent upon β-arrestin-2. Collective results in multiple cell lines also indicate that TP-β regulation of PTN is independent PTEN status.

Although the role of G protein coupled receptors (GPCRs) in tumor progression has been extensively studied, to the inventors' knowledge this is the first report that a GPCR alone was able to transform primary cells. Significantly, the inventors have found that TP-β is highly expressed in multiple cancer-derived cell lines (prostate, breast, colon, and renal cell carcinoma) and is absent in additional primary normal epithelial cells (e.g., PrEC prostate cells). Collectively, these findings, coupled with its correlation with disease progression; metastatic potential and overall patient survival make TP-β an ideal candidate for therapeutic intervention.

I. CANCERS

A. Genitourinary Cancers

Genitourinary (GU) cancers are those cancers affecting organs of the body that help eliminate waste products, although not exclusively. Included within this group are cancers of the prostate, bladder, urethra, kidney (renal cell) and testicles. In 2007, it is estimated that nearly one out of four new cancers diagnosed in the United States will be a genitourinary (GU) malignancy (prostate, kidney, bladder/urethral or testicular cancer), and 10% of cancer deaths will result from GU cancers. Despite significant progress in molecular and cellular biology that has helped identify specific molecular pathways that contribute to the biological potential and behavior of GU cancers, current treatments for advanced prostate, kidney, urethral and bladder cancers remain limited.

i. Bladder Cancer a. General Background

Bladder cancer refers to any of several types of malignant growths of the urinary bladder, with over 65,000 new cases and some 13,750 attributed deaths reported in 2007 alone. It is a disease in which abnormal cells multiply without control in the bladder. The bladder is a hollow, muscular organ that stores urine; it is located in the pelvis. The most common type of bladder cancer begins in cells lining the inside of the bladder and is called urothelial cell or transitional cell carcinoma (UCC or TCC).

Bladder cancer characteristically causes blood in the urine, this may be visible to the naked eye (frank haematuria) or detectable only be microscope (microscopic haematuria). Other possible symptoms include pain during urination, frequent urination or feeling the need to urinate without results. These signs and symptoms are not specific to bladder cancer, and are also caused by non-cancerous conditions, including prostate infections and cystitis.

Exposure to environmental carcinogens of various types is responsible for the development of most bladder cancers. Tobacco use (specifically cigarette smoking) is thought to cause 50% of bladder cancers discovered in male patients and 30% of those found in female patients. Thirty percent of bladder tumors probably result from occupational exposure in the workplace to carcinogens such as benzidine. Occupations at risk are metal industry workers, rubber industry workers, workers in the textile industry and people who work in printing. Hairdressers are thought to be at risk as well because of their frequent exposure to permanent hair dyes. It has been proposed that hair dyes are a risk factor, and some have shown an odds ratio of 2.1 to 3.3 for risk of developing bladder cancer among women who use permanent hair yes, while others have shown no correlation between the use of hair dyes and bladder cancer. Certain drugs such as cyclophosphamide and phenacetin are known to predispose to bladder TCC. Chronic bladder irritation (infection, bladder stones, catheters, bilharzia) predisposes to squamous cell carcinoma of the bladder. Approximately 20% of bladder cancers occur in patients without predisposing risk factors. Bladder cancer is not currently believed to be heritable.

Like virtually all cancers, bladder cancer development involves the acquisition of mutations in various oncogenes and tumor supressor genes. Genes which may be altered in bladder cancer include FGFR3, HRAS, RB1 and P53. Several genes have been identified which play a role in regulating the cycle of cell division, preventing cells from dividing too rapidly or in an uncontrolled way. Alterations in these genes may help explain why some bladder cancers grow and spread more rapidly than others.

A family history of bladder cancer is also a risk factor for the disease. Many cancer experts assert that some people appear to inherit reduced ability to break down certain chemicals, which makes them more sensitive to the cancer-causing effects of tobacco smoke and certain industrial chemicals.

b. Traditional Diagnosis

The gold standard of diagnosing bladder cancer is urine cytology and transurethral (through the urethra) cystoscopy. Urine cytology can be obtained in voided urine or at the time of the cystoscopy ("bladder washing"). Cytology is very specific (a positive result is highly indicative of bladder cancer) but suffers from low sensitivity (a negative result does not exclude the diagnosis of cancer). There are newer urine bound markers for the diagnosis of bladder cancer. These markers are more sensitive but not as specific as urine cytology. They are much more expensive as well. Many patients with a history, signs, and symptoms suspicious for bladder cancer are referred to a urologist or other physician trained in cystoscopy, a procedure in which a flexible tube bearing a camera and various instruments is intruduced into the bladder through the urethra. Suspicious lesions may be biopsied and sent for pathologic analysis.

Ninety percent of bladder cancer are transitional cell carcinomas (TCC) that arise from the inner lining of the bladder called the urothelium. The other 10% of tumours are squamous cell carcinoma, adenocarcinoma, sarcoma, small cell carcinoma and secondary deposits from cancers elsewhere in the body.

TCCs are often multifocal, with 30-40% of patients having a more than one tumour at diagnosis. The pattern of growth of TCCs can be papillary, sessile (flat) or carcinoma-in-situ (CIS). The 1973 WHO grading system for TCCs (papilloma, G1, G2 or G3) is most commonly used despite being superseded by the 2004 WHO grading (papillary neoplasm of low malignant potential (PNLMP), low grade and high grade papillary carcinoma. CIS invariably consists of cytologically high grade tumour cells.

Bladder TCC is staged according to the 1997 TNM system:
Ta—non-invasive papillary tumour
T1—invasive but not as far as the muscular bladder layer
T2—invasive into the muscular layer
T3—invasive beyond the muscle into the fat outside the bladder
T4—invasive into surrounding structures like the prostate, uterus or pelvic wall The following stages are used to classify the location, size, and spread of the cancer, according to the TNM (tumor, lymph node, and metastases) staging system:

Stage 0: Cancer cells are found only on the inner lining of the bladder.
Stage I: Cancer cells have proliferated to the layer beyond the inner lining of the urinary bladder but not to the muscles of the urinary bladder.
Stage II: Cancer cells have proliferated to the muscles in the bladder wall but not to the fatty tissue that surrounds the urinary bladder.
Stage III: Cancer cells have proliferated to the fatty tissue surrounding the urinary bladder and to the prostate gland, vagina, or uterus, but not to the lymph nodes or other organs.
Stage IV: Cancer cells have proliferated to the lymph nodes, pelvic or abdominal wall, and/or other organs.
Recurrent: Cancer has recurred in the urinary bladder or in another nearby organ after having been treated.

ii. Renal Cancer a. General Background

Renal cell carcinoma is the most common form of kidney cancer arising from the renal tubule. It is the most common type of kidney cancer in adults. Initial treatment is surgery. It is notoriously resistant to radiation therapy and chemotherapy, although some cases respond to immunotherapy. The advent of targeted cancer therapies such as Sunitinib has vastly improved the outlook for treatment of RCC.

Renal cell carcinoma affects about three in 10,000 people, resulting in about 31,000 new cases in the US per year. Every year, about 12,000 people in the US die from renal cell carcinoma. It is more common in men than women, usually affecting men older than 55. Why the cells become cancerous is not known. A history of smoking greatly increases the risk for developing renal cell carcinoma. Some people may also have inherited an increased risk to develop renal cell carcinoma, and a family history of kidney cancer increases the risk. People with von Hippel-Lindau disease, a hereditary disease that also affects the capillaries of the brain, commonly also develop renal cell carcinoma. Kidney disorders that require dialysis for treatment also increase the risk for developing renal cell carcinoma.

b. Traditional Diagnosis

The characteristic appearance of renal cell carcinoma (RCC) is a solid renal lesion which disturbs the renal contour. It will frequently have an irregular or lobulated margin. 85% of solid renal masses will be RCC. Ten percent of RCC will contain calcifications, and some contain macroscopic fat (likely due to invasion and encasement of the perirenal fat). Following intravenous contrast administration (computed tomography or magnetic resonance imaging), enhancement will be noted, and will increase the conspicuity of the tumor relative to normal renal parenchyma.

A list of solid renal lesions includes renal cell carcinoma, metastasis from an extra-renal primary neoplasm, renal lymphoma, squamous cell carcinoma, juxtaglomerular tumor (reninoma), transitional cell carcinoma, angiomyolipoma, oncocytoma and Wilm's tumor. In particular, reliably distinguishing renal cell carcinoma from an oncocytoma (a benign lesion) is not possible using current medical imaging or percutaneous biopsy.

Renal cell carcinoma may also be cystic. As there are several benign cystic renal lesions (simple renal cyst, hemorrhagic renal cyst, multilocular cystic nephroma, polycystic kidney disease), it may occasionally be difficult for the radiologist to differentiate a benign cystic lesion from a malignant one. Bosniak developed a classification system for cystic renal lesions that classifies them based specific imaging features into groups that are benign and those that need surgical resection. At diagnosis, 30% of renal cell carcinoma has spread to that kidney's renal vein, and 5-10% has continued on into the inferior vena cava.

Percutaneous biopsy can be performed by a radiologist using ultrasound or computed tomography to guide sampling of the tumor for the purpose of diagnosis. However this is not routinely performed because when the typical imaging features of renal cell carcinoma are present, the possibility of an incorrectly negative result together with the risk of a medical complication to the patient make it unfavorable from a risk-benefit perspective. This is not completely accurate, there are new experimental treatments.

iii. Prostate Cancer a. General Background

Prostate cancer is a disease in which cancer develops in the prostate, a gland in the male reproductive system. In 2007, almost 220,000 new cases were reported, and over 27,000 deaths were attributed to this malignancy. It occurs when cells of the prostate mutate and begin to multiply out of control. These cells may spread (metastasize) from the prostate to other parts of the body, especially the bones and lymph nodes. Prostate cancer may cause pain, difficulty in urinating, erectile dysfunction and other symptoms.

Rates of prostate cancer vary widely across the world. Although the rates vary widely between countries, it is least common in South and East Asia, more common in Europe, and most common in the United States. According to the American Cancer Society, prostate cancer is least common among Asian men and most common among black men, with figures for white men in-between. However, these high rates may be affected by increasing rates of detection.

Prostate cancer develops most frequently in men over fifty. This cancer can occur only in men, as the prostate is exclusively of the male reproductive tract. It is the most common type of cancer in men in the United States, where it is responsible for more male deaths than any other cancer, except lung cancer. However, many men who develop prostate cancer never have symptoms, undergo no therapy, and eventually die of other causes. Many factors, including genetics and diet, have been implicated in the development of prostate cancer.

b. Traditional Diagnosis

Prostate cancer screening is an attempt to find unsuspected cancers. Screening tests may lead to more specific follow-up tests such as a biopsy, where small pieces of the prostate are removed for closer study. As of 2006 prostate cancer screening options include the digital rectal exam and the prostate specific antigen (PSA) blood test. Screening for prostate cancer is controversial because it is not clear if the benefits of screening outweigh the risks of follow-up diagnostic tests and cancer treatments.

Prostate cancer is a slow-growing cancer, very common among older men. In fact, most prostate cancers never grow to the point where they cause symptoms, and most men with prostate cancer die of other causes before prostate cancer has an impact on their lives. The PSA screening test may detect these small cancers that would never become life threatening. Doing the PSA test in these men may lead to overdiagnosis, including additional testing and treatment. Follow-up tests, such as prostate biopsy, may cause pain, bleeding and infection. Prostate cancer treatments may cause urinary incontinence and erectile dysfunction. Therefore, it is essential that the risks and benefits of diagnostic procedures and treatment be carefully considered before PSA screening.

Prostate cancer screening generally begins after age 50, but this can vary due to ethnic backgrounds. Thus, the American Academy of Family Physicians and American College of Physicians recommend the physician discuss the risks and benefits of screening and decide based on individual patient preference. Although there is no officially recommended cutoff, many health care providers stop monitoring PSA in men who are older than 75 years old because of concern that prostate cancer therapy may do more harm than good as age progresses and life expectancy decreases.

Digital rectal examination (DRE) is a procedure where the examiner inserts a gloved, lubricated finger into the rectum to check the size, shape, and texture of the prostate. Areas which are irregular, hard or lumpy need further evaluation, since they may contain cancer. Although the DRE only evaluates the back of the prostate, 85% of prostate cancers arise in this part of the prostate. Prostate cancer which can be felt on DRE is generally more advanced. The use of DRE has never been shown to prevent prostate cancer deaths when used as the only screening test.

The PSA test measures the blood level of prostate-specific antigen, an enzyme produced by the prostate. Specifically, PSA is a serine protease similar to kallikrein. Its normal function is to liquify gelatinous semen after ejaculation, allowing spermatazoa to more easily navigate through the uterine cervix.

PSA levels under 4 ng/mL (nanograms per milliliter) are generally considered normal, however in individuals below the age of 50 sometimes a cutoff of 2.5 is used for the upper limit of normal, while levels over 4 ng/mL are considered abnormal (although in men over 65 levels up to 6.5 ng/mL may be acceptable, depending upon each laboratory's reference ranges). PSA levels between 4 and 10 ng/mL indicate a risk of prostate cancer higher than normal, but the risk does not seem to rise within this six-point range. When the PSA level is above 10 ng/mL, the association with cancer becomes stronger. However, PSA is not a perfect test. Some men with prostate cancer do not have an elevated PSA, and most men with an elevated PSA do not have prostate cancer.

PSA levels can change for many reasons other than cancer. Two common causes of high PSA levels are enlargement of the prostate (benign prostatic hypertrophy (BPH)) and infection in the prostate (prostatitis). It can also be raised for 24 hours after ejaculation and several days after catheterization. PSA levels are lowered in men who use medications used to treat BPH or baldness. These medications, finasteride (marketed as Proscar or Propecia) and dutasteride (marketed as Avodart), may decrease the PSA levels by 50% or more.

Several other ways of evaluating the PSA have been developed to avoid the shortcomings of simple PSA screening. The use of age-specific reference ranges improves the sensitivity and specificity of the test. The rate of rise of the PSA over time, called the PSA velocity, has been used to evaluate men with PSA levels between 4 and 10 ng/ml, but as of 2006, it has not proven to be an effective screening test. Comparing the PSA level with the size of the prostate, as measured by ultrasound or magnetic resonance imaging, has also been studied. This comparison, called PSA density, is both costly and, as of 2006, has not proven to be an effective screening test. PSA in the blood may either be free or bound to other proteins. Measuring the amount of PSA which is free or bound may provide additional screening information, but as of 2006, questions regarding the usefulness of these measurements limit their widespread use.

When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

If cancer is suspected, a biopsy is offered. During a biopsy a urologist obtains tissue samples from the prostate via the rectum. A biopsy gun inserts and removes special hollow-core needles (usually three to six on each side of the prostate) in less than a second. Prostate biopsies are routinely done on an outpatient basis and rarely require hospitalization. Fifty-five percent of men report discomfort during prostate biopsy.

The tissue samples are then examined under a microscope to determine whether cancer cells are present, and to evaluate the microscopic features of any cancer found. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate. In the TNM system, clinical T1 and T2 cancers are found only in the prostate, while T3 and T4 cancers have spread elsewhere. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans should reveal osteoblastic appearance due to increased bone density in the areas of bone metastisis—opposite to what is found in many other cancers that metastisize.

iv. Urethral Cancer a. General Background

The urethra is the tube that carries urine from the bladder to outside the body. In women, the urethra is about 1½ inches long and is just above the vagina. In men, the urethra is about 8 inches long, and goes through the prostate gland and the penis to the outside of the body. In men, the urethra also carries semen. Urethral cancer is a rare cancer that occurs more often in women than in men. There are different types of urethral cancer that begin in cells that line the urethra. Squamous cell carcinoma is the most common type of urethral cancer. It forms in cells in the part of the urethra near the bladder in women, and in the lining of the urethra in the penis in men. Transitional cell carcinoma forms in the area near the urethral opening in women, and in the part of the urethra that goes through the prostate gland in men. Adenocarcinoma forms in glands near the urethra in both men and women.

Urethral cancer can metastasize quickly to tissues around the urethra and is often found in nearby lymph nodes by the time it is diagnosed. Age and a history of bladder cancer can affect the risk of developing urethral cancer, as well as having a history of bladder cancer, having conditions that cause chronic inflammation in the urethra, including sexually transmitted diseases (STDs), frequent urinary tract infections (UTIs), being 60 or older, and being a white female. Possible signs of urethral cancer include bleeding or trouble with urination (weak flow, frequent urination, discharge), or a lump or thickness in the perineum or penis or lymph nodes in the groin area.

Certain factors affect prognosis and treatment options. The prognosis depends on the stage and size of the cancer, where in the urethra the cancer first formed, the patient's general health, and whether the cancer has just been diagnosed or has recurred. Treatment options depend on the stage of the cancer and where it is in the urethra, the patient's sex and general health and whether the cancer has just been diagnosed or has recurred.

b. Traditional Diagnosis

Tests that examine the urethra and bladder are used to detect (find) and diagnose urethral cancer. The following tests and procedures may be used.

Physical exam and history. An exam of the body to check general signs of health, including checking for signs of disease, such as lumps or anything else that seems unusual. A history of the patient's health habits and past illnesses and treatments will also be taken.

Laboratory tests. Medical procedures that test samples of tissue, blood, urine, or other substances in the body. These tests help to diagnose disease, plan and check treatment, or monitor the disease over time.

Urine cytology. Examination of urine under a microscope to check for abnormal cells.

Urinalysis. A test to check the color of urine and its contents, such as sugar, protein, blood, and white blood cells. If white blood cells (a sign of infection) are found, a urine culture is usually done to find out what type of infection it is.

Digital rectal exam. An exam of the rectum. The doctor or nurse inserts a lubricated, gloved finger into the lower part of the rectum to feel for lumps or anything else that seems unusual. This procedure may be done while the patient is under anesthesia.

Pelvic exam. An exam of the vagina, cervix, uterus, fallopian tubes, ovaries, and rectum. The doctor or nurse inserts one or two lubricated, gloved fingers of one hand into the vagina and places the other hand over the lower abdomen to feel the size, shape, and position of the uterus and ovaries. A speculum is also inserted into the vagina and the doctor or nurse looks at the vagina and cervix for signs of disease. This may be done while the patient is under anesthesia.

Cystoscopy. A procedure to look inside the urethra and bladder to check for abnormal areas. A cystoscope (a thin, lighted tube) is inserted through the urethra into the bladder. Tissue samples may be taken for biopsy.

Biopsy. The removal of cells or tissues from the urethra, bladder, and, sometimes, the prostate gland, so they can be viewed under a microscope by a pathologist to check for signs of cancer.

B. Gastrointestinal Cancers i. Colorectal Cancers a. General Background

Colorectal cancer, also called colon cancer or bowel cancer, includes cancerous growths in the colon, rectum and appendix. It is the third most common form of cancer and the second leading cause of cancer-related death in the Western world. Colorectal cancer causes 655,000 deaths worldwide per year. Many colorectal cancers are thought to arise from adenomatous polyps in the colon. These mushroom-like growths are usually benign, but some may develop into cancer over time. The majority of the time, the diagnosis of localized colon cancer is through colonoscopy. Therapy is usually through surgery, which in many cases is followed by chemotherapy.

Colon cancer often causes no symptoms until it has reached a relatively advanced stage. Thus, many organizations recommend periodic screening for the disease with fecal occult blood testing and colonoscopy. When symptoms do occur, they depend on the site of the lesion. Generally speaking, the nearer the lesion is to the anus, the more bowel symptoms there will be, such as change in bowel habits, change in frequency (constipation and/or diarrhea), change in the quality of stools, change in consistency of stools, bloody stools or rectal bleeding, stools with mucus, tarry stools (melena) (more likely related to upper gastrointestinal, e.g., stomach or duodenal disease), feeling of incomplete defecation (tenesmus) (usually associated with rectal cancer), reduction in diameter of feces, and bowel obstruction (rare).

Especially in the cases of cancer in the ascending colon, sometimes only the less specific constitutional symptoms will be found: anemia, with symptoms such as dizziness, malaise and palpitations. Clinically there will be pallor and a complete blood picture will confirm the low hemoglobin level. Also seen are anorexia, asthenia, and unexplained weight loss.

There may also be symptoms attributed to distant metastasis, such as shortness of breath as in lung metastasis, epigastric or right upper quadrant pain, as in liver metastasis, and rarely can there be jaundice if the outflow of bile is blocked. Clinically there might be liver enlargement. Also, familial adenomatous polyposis (FAP) carries a near 100% risk of developing colorectal cancer by the age of 40 if untreated. Long-standing ulcerative colitis or Crohn's disease of the colon carries a risk of approximately 30% after 25 years if the entire colon is involved b. Traditional Diagnosis Digital rectal exam (DRE) is a common diagnostic approach, but only detects tumors large enough to be felt in the distal part of the rectum but is useful as an initial screening test. Fecal occult blood test (FOBT), a test for blood in the stool, is also used commonly. Measurement of the patient's blood for elevated levels of certain proteins can give an indication of tumor load. In particular, high levels of carcinoembryonic antigen (CEA) in the blood can indicate metastasis of adenocarcinoma. Stool DNA testing is an emerging technology in screening for colorectal cancer. Pre-malignant adenomas and cancers shed DNA markers from their cells which are not degraded during the digestive process and remain stable in the stool. Capture, followed by Polymerase Chain Reaction amplifies the DNA to detectable levels for assay. Clinical studies have shown a cancer detection sensitivity of 71%-91%.

Colonoscopy or FOBT plus sigmoidoscopy are the preferred screening options in the U.S. Other similar techniques include double-contrast barium enema, virtual colonoscopy, standard computed axial tomography, positron emission tomography (PET), whole-Body PET imaging, The pathology of the tumor is usually reported from the analysis of tissue taken from a biopsy or surgery. A pathology report will usually contain a description of cell type and grade. The most common colon cancer cell type is adenocarcinoma which accounts for 95% of cases. Other, rarer types include lymphoma and squamous cell carcinoma.

Colon cancer staging is an estimate of the amount of penetration of a particular cancer. It is performed for diagnostic and research purposes, and to determine the best method of treatment. The systems for staging colorectal cancers largely depend on the extent of local invasion, the degree of lymph node involvement and whether there is distant metastasis. Definitive staging can only be done after surgery has been performed and pathology reports reviewed. An exception to this principle would be after a colonoscopic polypectomy of a malignant pedunculated polyp with minimal invasion. Pre-operative staging of rectal cancers may be done with endoscopic ultrasound. Adjuncts to staging of metastasis include Abdominal Ultrasound, CT, PET Scanning, and other imaging studies.

ii. Pancreatic Cancer a. General Background

Pancreatic cancer is a malignant tumor within the pancreatic gland. Each year about 33,000 individuals in the United States are diagnosed with this condition, and more than 60,000 in Europe. Depending on the extent of the tumor at the time of diagnosis, the prognosis is generally regarded as poor, with few victims still alive five years after diagnosis, and complete remission still extremely rare. About 95% of pancreatic tumors are adenocarcinomas. The remaining 5% include other tumors of the exocrine pancreas (e.g., serous cystadenomas), acinar cell cancers, and pancreatic neuroendocrine tumors (such as insulinomas). These tumors have a completely different diagnostic and therapeutic profile, and generally a more favorable prognosis.

Early diagnosis of pancreatic cancer is difficult because the symptoms are so non-specific and varied. Common symptoms include pain in the upper abdomen that typically radiates to the back and is relieved by leaning forward (seen in carcinoma of the body or tail of the pancreas), loss of appetite, significant weight loss and painless jaundice related to bile duct obstruction (carcinoma of the head of the pancreas). All of these symptoms can have multiple other causes. Therefore, pancreatic cancer is often not diagnosed until it is advanced.

Jaundice occurs when the tumor grows and obstructs the common bile duct, which runs partially through the head of the pancreas. Tumors of the head of the pancreas (approximately 60% of cases) are more likely to cause jaundice by this mechanism. Trousseau sign, in which blood clots form spontaneously in the portal blood vessels, the deep veins of the extremities, or the superficial veins anywhere on the body, is sometimes associated with pancreatic cancer. Clinical depression has been reported in association with pancreatic cancer, sometimes presenting before the cancer is diagnosed. However, the mechanism for this association is not known.

Risk factors for pancreatic cancer include age, male gender, ethnicity (African increases risk), smoking, diets high in meat, obesity, diabetes mellitus, chronic pancreatitis, and *Helicobacter pylori* infection. Occupational exposure to certain pesticides, dyes, and chemicals related to gasoline Family history, including autosomal recessive ataxia-telangiectasia and autosomal dominantly inherited mutations in the BRCA2 gene, Peutz-Jeghers syndrome due to mutations in the STK11 tumor suppressor gene, hereditary non-polyposis colon cancer (Lynch syndrome), familial adenomatous polyposis, and the familial atypical multiple mole melanoma-pancreatic cancer syndrome (FAMMM-PC) due to mutations in the CDKN2A tumor suppressor gene.

b. Traditional Diagnosis

The Courvoisier sign defines the presence of jaundice and a painlessly distended gallbladder as strongly indicative of pancreatic cancer, and may be used to distinguish pancreatic cancer from gallstones. Pancreatic cancer is usually discovered during the course of the evaluation of aforementioned symptoms. Liver function tests may show a combination of results indicative of bile duct obstruction (raised conjugated bilirubin, γ-glutamyl transpeptidase and alkaline phosphatase levels). CA19-9 (carbohydrate antigen 19.9) is a tumor marker that is frequently elevated in pancreatic cancer. Imaging studies, such as ultrasound or abdominal CT may be used to identify tumors. Endoscopic ultrasound (EUS) is another procedure that can help visualize the tumor and obtain tissue to establish the diagnosis.

iii. Stomach Cancer a. General Background

Stomach cancer (also called gastric cancer) can develop in any part of the stomach and may spread throughout the stomach and to other organs; particularly the esophagus and the small intestine. Stomach cancer causes nearly one million deaths worldwide per year, and represents roughly 2% (25,500 cases) of all new cancer cases yearly in the United States; however, but it is much more common in Korea, Japan, Great Britain, South America, and Iceland, being associated with high salt in the diet, smoking, and low intake of fruits and vegetables. Infection with the bacterium *H. pylori* is the main risk factor in about 80% or more of gastric cancers. It is more common in men, with up to 3 males are affected for every female. Estrogen may protect women against the development of this cancer form. A very small percentage of diffuse-type gastric cancers (see Histopathology below) are thought to be genetic. Metastasis occurs in 80-90% of individuals with stomach cancer, with a five year survival rate of 75% in those diagnosed in early stages and less than 30% of those diagnosed in late stages. The death rate is 12,400 a year in the United States.

Stomach cancer is often asymptomatic or causes only non-specific symptoms in its early stages. By the time symptoms occur, the cancer has generally metastasized to other parts of the body, one of the main reasons for its poor prognosis. Stomach cancer can cause the following signs and symptoms: early—indigestion or a burning sensation (heartburn) and loss of appetite, especially for meat; late—abdominal or discomfort in the upper abdomen; nausea and vomiting; diarrhea or constipation; bloating of the stomach after meals; weight loss; weakness and fatigue; bleeding (vomiting blood or having blood in the stool), which can lead to anemia. These can be symptoms of other problems such as a stomach virus, gastric ulcer or tropical sprue and diagnosis should be performed by a gastroenterologist or an oncologist.

b. Traditional Diagnosis

Gastroscopic exam is the diagnostic method of choice, with an upper GI series (may be called barium roentgenogram) being common. Fecal occult blood test is obsolete except possibly as a screening test; a negative test proves nothing and a positive result may result from a large number of other conditions beside gastric carcinoma. Abnormal tissue seen in a gastroscope examination will be biopsied by the surgeon or gastroenterologist. This tissue is then sent to a pathologist for histological examination under a microscope to check for the presence of cancerous cells. A biopsy, with subsequent histological analysis, is the only sure way to confirm the presence of cancer cells. A condition of darkened hyperplasia of the skin, frequently of the axilla and groin, known as acanthosis nigricans, commonly prompts a study into gastric carcinoma. It should be noted that this hyperplasia can be found in obese individuals with no underlying cancer.

Gastric adenocarcinoma is a malignant epithelial tumor, originating from glandular epithelium of the gastric mucosa. It invades the gastric wall, infiltrating the muscularis mucosae, the submucosa and thence the muscularis propria. Histologically, there are two major types of gastric cancer (Lauren classification): intestinal type and diffuse type.

In intestinal type adenocarcinoma, tumor cells describe irregular tubular structures, harboring pluristratification, multiple lumens, reduced stroma ("back to back" aspect). Often, it associates intestinal metaplasia in neighboring mucosa. Depending on glandular architecture, cellular pleomorphism and mucosecretion, adenocarcinoma may present 3 degrees of differentiation: well, moderate and poorly differentiate.

For diffuse type adenocarcinoma (mucinous, colloid), tumor cells are discohesive and secrete mucus which is delivered in the interstitium producing large pools of mucus/colloid (optically "empty" spaces). It is poorly differentiated. If the mucus remains inside the tumor cell, it pushes the nucleus at the periphery—"signet-ring cell."

If cancer cells are found in the tissue sample, the next step is to stage, or find out the extent of the disease. Various tests determine whether the cancer has spread and, if so, what parts of the body are affected. Because stomach cancer can spread to the liver, the pancreas, and other organs near the stomach as well as to the lungs, the doctor may order a CT scan, an ultrasound exam, or other tests to check these areas. Blood tests for tumor markers, such as carcinoembryonic antigen (CEA) and carbohydrate antigen (CA) may be ordered, as their levels correlate to extent of metastasis, especially to the liver, and the cure rate. Staging may not be complete until after surgery. The surgeon removes nearby lymph nodes and possibly samples of tissue from other areas in the abdomen for examination by a pathologist.

C. Hematopoietic Cancers i. Leukemia a. General Background

Leukemia is a cancer of the blood or bone marrow and is characterized by an abnormal proliferation (production by multiplication) of blood cells, usually white blood cells (leukocytes). It is part of the broad group of diseases called hematological neoplasms. Damage to the bone marrow, by way of displacing the normal bone marrow cells with higher numbers of immature white blood cells, results in a lack of blood platelets, which are important in the blood clotting process. This means people with leukemia may become bruised, bleed excessively, or develop pinprick bleeds (petechiae). White blood cells, which are involved in fighting pathogens, may be suppressed or dysfunctional, causing the the patient's immune system to be unable to fight off a simple infection or to start attacking other body cells. Finally, the red blood cell deficiency leads to anemia, which may cause dyspnea.

All of the symptoms for leukemias can be attributed to other diseases: fever, chills, night sweats and other flu-like symptoms; weakness and fatigue; swollen or bleeding gums; neurological symptoms (headache); enlarged liver and spleen; frequent infection; bone pain; joint pain; dizziness; swollen tonsils.

The word leukemia, which means "white blood," is derived from the disease's namesake high white blood cell counts that most leukemia patients have before treatment. The high number of white blood cells are apparent when a blood sample is viewed under a microscope. Frequently, these extra white blood cells are immature or dysfunctional. The excessive number of cells can also interfere with the level of other cells, causing a harmful imbalance in the blood count.

Some leukemia patients do not have high white blood cell counts visible during a regular blood count. This less-common condition is called aleukemia. The bone marrow still contains cancerous white blood cells which disrupt the normal production of blood cells. However, the leukemic cells stay in the marrow instead of entering the bloodstream where they would be visible in a blood test. For an aleukemic patient, the white blood cell counts in the bloodstream can be normal or low. Aleukemia can occur in any of the four major types of leukemia, and is particularly common in hairy cell leukemia.

Leukemia is clinically and pathologically split into its acute and chronic forms. Acute leukemia is characterized by the rapid proliferation of immature blood cells. This crowding makes the bone marrow unable to produce healthy blood cells. Acute forms of leukemia can occur in children and young adults. Immediate treatment is required in acute leukemias due to the rapid progression and accumulation of the malignant cells, which then spill over into the bloodstream and spread to other organs of the body.

Chronic leukemia is distinguished by the excessive build up of relatively mature, but still abnormal, blood cells. Typically taking months to years to progress, the cells are produced at a much higher rate than normal cells, resulting in many abnormal white blood cells in the blood. Chronic leukemia mostly occurs in older people, but can theoretically occur in any age group. Whereas acute leukemia must be treated immediately, chronic forms are sometimes monitored for some time before treatment to ensure maximum effectiveness of therapy.

Furthermore, the diseases are classified into (a) lymphocytic or lymphoblastic, which indicate that the cancerous change took place in a type of marrow cell that normally goes on to form lymphocytes, and (b) myelogenous or myeloid, which indicate that the cancerous change took place in a type of marrow cell that normally goes on to form red cells, some types of white cells, and platelets (see lymphoid cells versus myeloid cells). Combining these two classifications provides a total of four main categories of leukemias.

Specific forms of leukemia include Acute Myelogenous Leukemia (AML), Chronic Myelogenous Leukemia (CML), Acute Lymphocytic Leukemia (ALL), Chronic Lymphocytic Leukemia (CLL), transformation of CLL to high-grade disease or aggressive non-Hodgkin's lymphoma, and Hairy Cell Leukemia (HCL).

b. Traditional Diagnosis

For diagnosis of leukemia, blood tests and a bone marrow examination are required.

ii. Lymphoma a. General Background

Lymphoma is a type of cancer that originates in lymphocytes (a type of white blood cell in the vertebrate immune system). There are many types of lymphoma. In the 19th and 20th centuries, the affliction was called Hodgkin's Disease, as it was discovered by Thomas Hodgkin in 1832. Colloquially, lymphoma is broadly categorized as Hodgkin's lymphoma and non-Hodgkin lymphoma (all other types of lymphoma). Scientific classification of the types of lymphoma is more detailed. Although older classifications referred to histiocytic lymphomas, these are recognized in newer classifications as of B, T or NK cell lineage. Histiocytic malignancies are rare and are classified as sarcomas.

According to the U.S. National Institutes of Health, lymphomas account for about five percent of all cases of cancer in the United States, and Hodgkin's lymphoma in particular accounts for less than one percent of all cases of cancer in the United States. Because the lymphatic system is part of the body's immune system, patients with a weakened immune system, such as from HIV infection or from certain drugs or medication, also have a higher incidence of lymphoma.

The WHO Classification is the latest classification of lymphoma, published by the World Health Organization in 2001. This classification attempts to classify lymphomas by cell type, i.e., the normal cell type that most closely resembles the tumor. They are classified in three large groups: the B cell tumors, the T cell and natural killer cell tumors, Hodgkin lymphoma, and other less common groups:

b. Traditional Diagnosis

Hodgkin's lymphoma must be distinguished from non-cancerous causes of lymph node swelling (such as various infections) and from other types of cancer. Definitive diagnosis is by lymph node biopsy (usually excisional biopsy with microscopic examination). Blood tests are also performed to assess function of major organs and to assess safety for chemotherapy. Positron emission tomography (PET) is used to detect small deposits that do not show on CT scanning In some cases, a Gallium Scan may be used instead of a PET scan.

If non-Hodgkin's lymphoma is suspected, the doctor asks about the person's medical history and performs a physical exam. The exam includes feeling to see if the lymph nodes in the neck, underarm, or groin are enlarged. In addition to checking general signs of health, the doctor may perform blood tests.

A biopsy is needed to make a diagnosis. A surgeon removes a sample of tissue, which a pathologist can examine under a microscope to check for cancer cells. A biopsy for non-Hodgkin's lymphoma is usually taken from lymph nodes that are enlarged, but other tissues may be sampled as well. Biopsies in internal lymph nodes can also taken as needle biopsies under the guidance of CT scans. Rarely, an operation called a laparotomy may be performed. During this operation, a surgeon cuts into the abdomen and removes samples of tissue to be checked under a microscope.

The doctor may also order tests that produce pictures of the inside of the body. These may include:

X-rays: Pictures of areas inside the body created by high-energy radiation.

CT scan (computed tomography scan, also known as a "CAT scan"): A series of detailed pictures of areas inside the body. The pictures are created by a computer linked to an x-ray machine.

PET scan (positron emission tomography scan): This is an imaging test that detects uptake of a radioactive tracer by the tumor. More often, the PET scan can be combined with the CT scan.

MRI (magnetic resonance imaging): Detailed pictures of areas inside the body produced with a powerful magnet linked to a computer.

These tests are only used under certain circumstances:

Lymphangiogram: Pictures of the lymphatic system taken with x-rays after a special dye is injected to outline the lymph nodes and vessels. This test is not used as often because of the adoption of CT scan and the PET scan technologies.

Gallium scan: Gallium is a rare metal that behaves in the body in a fashion similar to iron, so that it concentrates in areas of inflammation or rapid cell-division, and hence is useful for imaging the entire lymphatic system for staging of lymphoma once the presence of the disease has been confirmed. PET scans have supplanted gallium scans for evaluation and follow up of NHL.

II. THROMBOXANE RECEPTORS

A. Thromboxane Receptor Function

Thromboxane is intermediate in the metabolism of arachidonic acid via the COX pathway (Jabbour et al., 2006). After being made, it binds to thromboxane (TP) receptors which are G-protein coupled receptors (GPCRs) that have been shown to have a number of complex downstream signaling effects; although they are not fully understood and differ among cell types (Jabbour et al., 2006; Huang et al., 2004). The thromboxane receptor is found on the surface of cells in the endothelium of blood vessels and in the placenta which interacts with the eicosanoid lipid thromboxane. The TP GPCR has been implicated in a number of signaling effects such as platelet activation, smooth muscle contraction, and responses caused by the central and peripheral nervous system (Jabbour et al., 2006; Huang et al., 2004). Thromboxane is a potent stimulator for platelet aggregation and clot formation and also plays a role in vascular tone. Mutation of the receptor can lead to a bleeding disorder.

The gene responsible for the thromboxane receptor, TBXA2R is found on chromosome 19 and spans 15 kB.

B. β Isoform

It was discovered that TP receptors exist in two isoforms: TP-α and TP-β that differed in the amino acid sequence of their C-terminal tails which reside in the cytoplasm (Valentin et al., 2005). The α and β forms are differential regulated and under the control of 2 distinct promoters letting them have a wide variety of effects in a number of cell types (Coyle and Kinsella, 2005). The reason for and the effects of these two splices variants in humans is not understood (Valentin et al., 2005; Coyle and Kinsella, 2005).

The inventors have previously showed that the TP receptor is overexpressed in tissue of the most common forms of bladder cancer on the protein level, but not the mRNA level (Moussa et al., 2005). This first indicated TP receptor as a biomarker of bladder cancer. Further study by these inventors' laboratories has suggested that it is TPβ that is being overexpressed in relation to TP-α in common bladder tumor tissue samples. Based on this, it is hypothesized that TP-β protein detection could provide a new diagnostic tool in urine sample analysis. The detection of TP-β overexpression at low levels in patient urine samples provides a non-invasive early diagnosis method and easy technique for follow up detection of recurrence.

C. Sequences

The nucleic acid and amino acid sequences for TP-α and TP-β are found in the sequence listing as SEQ ID NOS:1-2 (NM_001060; NP_001051) and 3-4 (NM_201636; NP_963998), respectively.

III. TP-β PATIENT SELECTIONS AND MONITORING

According to the inventors' findings, detection of abnormal levels of TP-β is likely to be of diagnostic importance in GU cancers, GI cancers and leukemais. In certain cancers, e.g., bladder, prostate, the protein can be found in diagnostically significant levels in urine, semen and prostatic fluid. In others, a tumor biopsy may be required. Testing for increased levels of TP-β will permit identification of patients with GU and GI cancers and leukemias more likely to respond to TP-β antagonist therapies. In addition, one may monitor disease and/or treatment progression in GU/GI/leukemia cancer patients using these same techniques.

A commercial source for anti-TP-β antibody is Genway Biotech (San Diego, Calif.), cat. no. #18-461-10673.

A. Preparing Antibodies

Methods for the production of antibodies are well known in the art, as described in see, e.g., Harlow and Lane, 1988; U.S. Pat. No. 4,196,265. The methods for generating monoclonal antibodies (MAbs) generally begin along the same lines as those for preparing polyclonal antibodies. The first step for both these methods is immunization of an appropriate host. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes. Spleen cells and lymph node cells are preferred, the former because they are a rich source of antibody-producing cells that are in the dividing plasmablast stage. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Various methods may be employed for the cloning an expression of human light and heavy chain sequences. Wardemann et al. (2003) and Takekoshi et al. (2001), both of which disclose such techniques, are hereby incorporated by reference.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations; and U.S. Pat. No. 4,867,973 which describes antibody-therapeutic agent conjugates.

B. Immunologic Assays

Antibodies of the present invention can be used in characterizing the TP-β content of tumor biopsy, blood, urine, prostate fluid and semen through techniques such as RIAs, ELISAs and Western blotting. This provides early detection and monitoring of bladder cancer, possibly prior to tissue invasion and metastasis.

In the present invention, an ELISA assay is particularly contemplated. For example, antibodies to TP-β may be immobilized onto a selected surface, for example, a surface such as a microtiter well, a membrane, a filter, a bead or a dipstick. After washing to remove incompletely adsorbed material, it is desirable to bind or coat the surface with a non-specific agent that is known to be antigenically neutral with regard to the test sample, e.g., bovine serum albumin (BSA), casein or solutions of powdered milk. This allows for blocking of non-specific adsorption sites on the immobilizing surface and thus reduces the background caused by non-specific binding of antibody to antigen on the surface.

After binding of antibody to the surface and coating, the surface is exposed to urine, prostate fluid or semen. Following formation of specific immunocomplexes between antigens in the urine, prostate fluid or semen and the antibody, and subsequent washing, the occurrence and even amount of immunocomplex formation may be determined by subjecting the same to a second antibody having specificity for the antigen. Appropriate conditions preferably include diluting the sample with diluents such as BSA, bovine gamma globulin (BGG) and phosphate buffered saline (PBS)/Tween® (non-ionic surfactant). These added agents also tend to assist in the reduction of non-specific background. The detecting antibody is then allowed to incubate for from about 2 to about 4 hr, at temperatures preferably on the order of about 25° to about 27° C. Following incubation, the surface is washed so as to remove non-immunocomplexed material. A preferred washing procedure includes washing with a solution such as PBS/Tween® (non-ionic surfactant), or borate buffer.

To provide a detecting means, the second antibody will preferably have an associated label, e.g., an enzyme that will generate a color development upon incubating with an appropriate chromogenic substrate. Thus, for example, one will desire to contact and incubate the second antibody for a period of time and under conditions which favor the development of immunocomplex formation (e.g., incubation for 2 hr at room temperature in a PBS-containing solution such as PBS/Tween® (non-ionic surfactant)).

After incubation with the second antibody, and subsequent to washing to remove unbound material, the amount of label is quantified (e.g., by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label). Quantitation is then achieved by measuring the label, e.g., degree of color generation, e.g., using a visible spectrum spectrophotometer.

Other potential labels include radiolabels, fluorescent labels, dyes and chemilluminescent molecules (e.g., luciferase).

C. Dipstick Technology

U.S. Pat. No. 4,366,241, and Zuk, EP-A 0 143 574 describe migration type assays in which a membrane is impregnated with the reagents needed to perform the assay. An analyte detection zone is provided in which labeled analyte is bound and assay indicia is read.

U.S. Pat. No. 4,770,853, WO 88/08534, and EP-A 0 299 428 describe migration assay devices which incorporate within them reagents which have been attached to colored direct labels, thereby permitting visible detection of the assay results without addition of further substances.

U.S. Pat. No. 4,632,901, disclose a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

EP-A 0 125 118, disclose a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution.

EP-A 0 282 192, disclose a dipstick device for use in competition type assays.

U.S. Pat. No. 4,313,734 describes the use of gold sol particles as a direct label in a dipstick device.

U.S. Pat. No. 4,786,589 describes a dipstick immunoassay device in which the antibodies have been labeled with formazan.

U.S. Pat. No. 5,656,448 pertains to dipstick immunoassay devices comprising a base member and a single, combined sample contact zone and test zone, wherein the test zone incorporates the use of symbols to detect analytes in a sample of biological fluid. A first immunological component, an anti-immunoglobulin capable of binding to an enzyme-labeled antibody, is immobilized in a control indicator portion. A second immunological component, capable of specifically binding to a target analyte which is bound to the enzyme-labeled antibody to form a sandwich complex, is immobilized in a test indicia portion. The enzyme-labeled antibody produces a visual color differential between a control indicia portion and a non-indicia portion in the test zone upon contact with a substrate. The device additionally includes a first polyol and a color differential enhancing component selected from the group consisting of an inhibitor to the enzyme and a competitive secondary substrate for the enzyme distributed throughout the non-indicia portion of the test zone.

Figure 3:
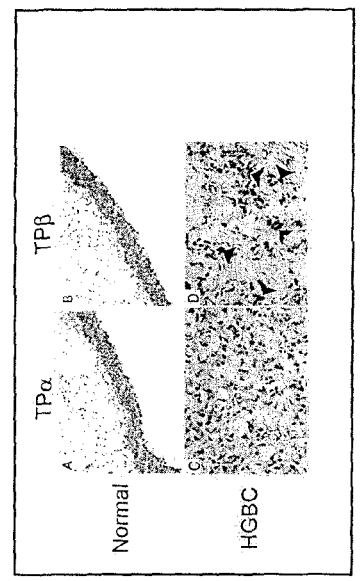
FIG. 3. TP isoform expression in bladder tissue. Immunohistochemical staining of TP receptor protein in human bladder tissue. Representative sections stained with rabbit anti-TP-α or TP-β isoform-specific antibody (From Anthony Ashton) using the Vectastain Elite ABC Kit. (Top panels) Normal urothelium (X100). (Bottom panels) Poorly differentiated, high grade bladder cancer (HGBC; 200X). Top and bottom panels are from the same section. Arrows indicate intensity staining The data presented are representative of 22 patient samples.

Assays for assessing TP-β levels are described in U.S. Ser. No. 12/253,592, filed Oct. 17, 2008, which is incorporated herein by reference. In particular, the use of TP-β levels in urine to diagnose cancers such as bladder cancers are described. Using ratios of TP-β to creatinine (see FIG. 3; used to assess urine concentration; normal creatinine is about 20 mg/dl-300 mg/dl), increased TP-β ratios as compared to controls are highly predictive of cancer. U.S. Pat. Nos. 5,955,370, 6,136,801 and 6,297,020, and U.S. Patent Publication 2008/0286825 each disclose the use of creatine in the normalization of urine testing, and are hereby incorporated by reference.

D. Kits

In still further embodiments, the present invention concerns immunodetection kits for use with the immunodetection methods described above. The kits will include antibodies to TP-β, and may contain other reagents as well. The immunodetection kits will thus comprise, in suitable container means, a first antibody that binds to TP-β, and optionally a second and distinct antibody to TP-β.

In certain embodiments, the antibody to TP-β may be pre-bound to a solid support, such as a column matrix, a microtitre plate, a filter, a membrane, a bead or a dipstick. The immunodetection reagents of the kit may take any one of a variety of forms, including antibodies to TP-β containing detectable labels. As noted above, a number of exemplary labels are known in the art and all such labels may be employed in connection with the present invention.

The kits may further comprise a suitably aliquoted composition of TP-β, whether labeled or unlabeled, as may be used to prepare a standard curve for a detection assay. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection or blow-molded plastic containers into which the desired vials are retained.

IV. TREATMENTS

A. TP-β/TXAS Inhibitors

The present invention relies on the use of thromboxane receptor β antagonists, alone or in conjunction with thromboxane synthase inhibitors, optionally further in conjunction with traditional anti-cancer therapies.

i. TP-β Inhibitors

TP-β inhibitors are available and can be obtained from commercial sources. A particular kind of drug is one that inhibits the actions of thromboxane $A_2$ (i.e., its ability to activate TP-β). Examples include GR32191 (VAPIPROST®), Daltroban (BM13505), Z-335, LCB-2853, SQ28668, SQ29548, ICI 192605, AH 23858, sulotroban, ONO3708, pinane $TXA_2$ or ifetroban. See also U.S. Pat. Nos. 5,128,359 and 5,280,034, and U.S. Patent Publication 2006/0217431.

ii. TXAS Inhibitors

TXAS inhibitors are available and can be obtained from commercial sources. A particular kind of drug is one inhibits the metabolism of arachidonic acid or prostaglandin $H_2$ to thromboxane A$_2$. Examples include dazoxiben, furegulate, ozagrel, OKY1581, CGS-12970, or UK 38485. See also U.S. Pat. Nos. 4,243,671, 5,597,848, 5,618,941, 5,158,967 and 5,091,191, and U.S. Patent Publication 2006/0217431.

B. Anti-Cancer Combinations

As discussed above, it may be desirable to combine TP-β/TXAS inhibitors with other therapies in the treatment of cancers. An "anti-cancer" therapy is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer therapies are described below as "standard of care" therapies and include biological agents (biotherapy), chemotherapy agents, and radiotherapy agents, surgery and immunotherapy. More generally, these therapies would be provided in a combined amount effective to kill or inhibit proliferation of the cancer cell. This process may involve contacting the cancer cell with the therapies at the same time, such as by contacting the cancer cell with a single composition or treatment that includes both agents, or by contacting the cancer cell with two distinct compositions or treatments at the same time.

Alternatively, the TP-β/TXAS therapy may precede or follow the other treatment by intervals ranging from minutes to weeks. In embodiments where the other agent and TP-β/TXAS therapy are applied separately to the cell, one would generally ensure that a significant period of time did not expire between the time of each delivery, such that the therapy and TP-β/TXAS therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, where TP-β/TXAS therapy is "A" and the secondary therapy is "B":

| A/B/A | B/A/B | B/B/A | A/A/B | A/B/B | B/A/A | A/B/B/B | B/A/B/B |
|---|---|---|---|---|---|---|---|
| B/B/B/A | B/B/A/B | A/A/B/B | | A/B/A/B | A/B/B/A | B/B/A/A | |
| B/A/B/A | B/A/A/B | A/A/A/B | | B/A/A/A | A/B/A/A | A/A/B/A | |

Administration of the TP-β/TXAS therapies of the present invention to a patient will follow general protocols for the administration of chemotherapeutics, taking into account the toxicity, if any, of the formulations. It is expected that the treatment cycles would be repeated as necessary, including two, three, four, five, six, seven, eight, nine, ten or more cycles.

In one embodiment, an anti-cancer therapy is radiotherapy. Radiotherapy includes, for example, fractionated radiotherapy, nonfractionated radiotherapy and hyperfractionated radiotherapy, and combination radiation and chemotherapy. Types of radiation also include ionizing (gamma) radiation, particle radiation, low energy transmission (LET), high energy transmission (HET), ultraviolet radiation, infrared radiation, visible light, and photosensitizing radiation.

In another embodiment, an anti-cancer therapy is chemotherapy. When the second anti-cancer therapy is chemotherapy, the chemotherapy may comprise administration of one or more of: 20-epi-1,25 dihydroxyvitamin D3; (1aS,8S,8aR,8bS)-6-amino-8-(((aminocarbonyl)oxy)methyl)-1,1a,2,8,8a,8b-hexahydro-8a-methoxy-5-methylazirino(2',3':3.4) pyrrolo[1,2-a]in-dole-4,7-dione; (8S-cis)-10-((3-amino-2,3,6-trideoxy-alpha-L-lyxo-hexopyranosyl)oxy)-7,8,-9,1,0-tetrahydro-6,8,11-trihydroxy-8-(hydroxyacetyl)-1-methoxy-5; (I)-mimosine; 1-(2-chloroethyl)-3-(4-methylcyclohexyl)-1-nitrosourea; 12-naphthacenedione; 131-meta-iodobenzyl guanidine (1-131 MIBG); 1,1',1"-phosphinothioylidynetris aziridine; 2-chloro-N-(2-chloroethyl)-N-methylethanamine; 2-deoxy-2-(((methylnitrosoamino)carbonyl)amino)-D-glucose; 2-deoxy-2-(3-methyl-3-nitrosoureido)-D-glucopyranose; 2,3,5-tris(1-aziridinyl)-2,5-cyclohexadiene-1,4-dione; 2,4,6-tris(1-aziridinyl)-s-thiazine; 2,4,6-tris(1-aziridinyl)-s-triazine; 3-deazauridine; 3-iodobenzylguanidine; 4-(bis(2-chloroethyl)amino)benzenebutanoic acid; 4-(bis(2-chloroethyl)amino)-L-phenylalanine; 4-demethoxy-3-deamino-3-aziridinyl-4-methylsulphonyl-daunorubicin; 5-(3,3-dimethyl-1-triazenyl)-1H-imidazole-4-carboxamide; 5-(bis(2-chloroethyl)amino)-2,4(1H,3H)-pyrimidinedione; 5-azacytidine; 5-ethynyluracil; 5-fluorouracil (5-FU); 5-FU and radiation; 5-FU plus leucovorin; 5,12-naphthacenedione; 6-azauridine; 6-mercaptopurine; 6-thioguanine; 8-azaguanine; 9-dioxamycin; 9-nitrocamptothecin; abiraterone; acivicin; aclacinomycin A; aclarubicin; acodazole; acodazole hydrochloride; acronine; acronycine; actinomycin D; Actinomycin D (also called Dactinomycin); acylfulvene; adecypenol; adozelesin; aldesleukin (interleukin-2); alitretinoin; allopurinol; ALL-TK antagonists; altretamine (hexamethylmelamine); altretamine (Hexylen); ambamustine; ambomycin; ametantrone; ametantrone acetate; amidox; amifostine; aminoglutethimide (cytadren); aminoimidazole carboxamide; aminolevulinic acid; amrubicin; amsacrine (also called "mAMSA"; m-AMSA or amsidine); anagrelide; anastrazole (arimidex); anastrozole; ancitabine; andrographolide; angiogenesis inhibitors; annamycin; antagonist D; antagonist G; antarelix; anthracycline antibiotics; anthracyline; anthramycin; antiandrogen; antibiotic derivatives; anti-dorsalizing morphogenetic protein-1; antiestrogen; antiestrogens; antimetabolites; antineoplaston; antisense oligonucleotides; aphidicolin glycinate; apoptosis gene modulators; apoptosis regulators; apurinic acid; Ara C; ara-CDP-DL-PTBA; arginine deaminase; arifostine; Arimidex; Aromasin; arsenic trioxide; asparaginase; asparaginase (elspar); asperlin; asulacrine; atamestane; atrimustine; axinastatin 1; axinastatin 2; axinastatin 3; azacitdine; azacitidine; azacitidine (ladakamycin); azaguanine; azaserine; azasetron; azatoxin; azatyrosine; azauridine; azetepa; azirino(2',3':3,4)pyrrolo[1,2-a]indole-4,7-dione; azotomycin; baccatin III derivatives; balanol; batimastat; BCG (theracys); BCG live; BCNU; BCNU chloroethyl nitrosoureas; BCR/ABL antagonists; benzamide; benzochlorins; benzodepa; benzoylstaurosporine; benzylguanine; beta lactam derivatives; beta-alethine; betaclamycin B; bethamethasone sodium phosphate; betulinic acid; bevacizumab; bexarotene; bFGF inhibitor; bicalutamide; bisanthrene; bisantrene; bisantrene hydrochloride; bisaziridinylspermine; bischloroethyl nitrosourea; bisnafide; bisnafide dimesylate; bistratene A; bizelesin; bleomycin; bleomycin (blenozane); bleomycin sulfate; bleomycins; breflate; brequinar; brequinar sodium; bromodeoxyuridine; bropirimine; broxuridine; budotitane; busulfan; busulfan (myleran); buthionine sulfoximine; cachectin; cactinomycin; calcipotriol; calphostin C; calusterone; camptothecin derivatives; canarypox IL-2; caracemide; carbamic acid ethyl ester; carbetimer; carboplatin (Paraplatin); carboxamide-amino-triazole; carboxyamidotriazole; CaRest M3; carmustine (BCNU or BiCNU); CARN 700; carubicin; carubicin hydrochloride; carzelesin; casein kinase inhibitors (ICOS); castanospermine; CCNU; cecropin B; cedefingol; celecoxib; cetrorelix; cetuximab; chlorambucil (leukeran); chlorins; chloroethyl nitrosoureas; chloroquinoxaline sulfonamide; chlorotrianisene; CHOP (cyclophosphamide, doxorubicin, vincristine, and prednisone including any combination of the components of CHOP); chorambucil; chorozotocin (DCNU); chromomycin A3; cicaprost; cirolemycin; cis-aminedichloro(2-methylpyridine) platinum; cisplatin (also called cis-ddpl or platinol); cisplatin and radiation; cisporphyrin; cis-retinoic acid; clomifene analogues; clotrimazole; coformycin; colchicine; collismycin B; combretastatin A4; combretastatin analogue; conagenin; CPT-11; crambescidin 816; crisnatol; crisnatol mesylate; cryptophycin 8; cryptophycin A derivatives; curacin A; cycloleucine; cyclopentanthraquinones; cyclophosphamide; cyclo-phosphamide; cyclophosphamide (cytoxan); cyclophosphamide anhydrous; cycloplatam; cypemycin; cytarabine; cytarabine HCl (cytosar-u); cytarabine ocfosfate; cytochalasin B; cytolytic factor; cytosine arabinoside; cytostatin; dacarbazine; daclizimab; dactinomycin (cosmegen); daunoinycin; daunorubicin; Daunorubincin HCl (cerubidine); decarbazine (DTIC-dome); decitabine; dehydrodidemnin B; demecolcine; depsipeptide; deslorelin; dexamethasone; dexormaplatin; dexverapamil; dezaguanine; dezaguanine mesylate; dianhydrogalactitol; diarizidinylspennine; diaziquone; diazooxonorleucine; dibromodulcitol; dibrospidium chloride; dicarbazine; didemnin B; didox; diethylnorspermine; diethylstilbestrol; diethylstilbestrol diphosphate; dihydro-5-azacytidine; diphenyl spiromustine; docetaxel; docetaxel (taxotere); docosanol; dolasetron; doxifluridine; doxorubicin; Doxorubicin (Adriamycin); Doxorubicin and Doxetaxel; doxorubicin HCl (adriamycin); droloxifene; droloxifene citrate; dromostanolone; dromostanolone propionate; dronabinol; duazomycin; duocarmycin SA; ebselen; ecomustine; edatrexate; edelfosine; edrecolomab; eflornithine; eflornithine hydrochloride; elemene; elinafide; elsamitrucin; emetine; emitefur; enloplatin; enpromate; epipodophyllotoxins; epipropidine; epirubicin; epirubicin hydrochloride; epristeride; erbulozole; erlinotib; erythrocyte gene therapy; esorubicin; esorubicin hydrochloride; estradiol; estramustine; estramustine analogue; estramustine phosphate sodium (emcyt); estrogen agonists; estrogen antagonists; ET-743; etanidazole; ethinyl estradiol; ethiodized oil; ethoglucid; ethyl carbamate; ethyl ester; ethyl methanesulfonate; etoposide; etoposide (VP16-213); etoposide orthoquinone; etoposide phosphate; etoprine; exemestane; fadrozole; fadrozole hydrochloride; fazarabine; Femara; fenretinide; filgrastim; finasteride; flavopiridol; flezelastine; floxuridine; floxuridine (fudr); fluasterone; Fludarabine; fludarabine (fludara); fludarabine phosphate; fluorocitabine; fluorodaunorunicin hydrochloride; fluoxymesterone (halotestin); flutamide; flutamide (eulexin); fluxuridine; forfenimex; formestane; fosquidone; fostriecin; fostriecin sodium; fotemustine; fulvestrant; gadolinium texaphyrin; galarubicin; gallium nitrate; gallium nitrate (granite); galocitabine; ganirelix; gefitinib; gelatinase inhibitors; gemcitabine; gemcitabine (gemzar); gemcitabine hydrochloride; gemicitabine; gemtuzumab; genistein; glufosfamide; glutamic acid; glutathione inhibitors; goserelin (zoladex); GPX100; gramicidin D; hepsulfiun; heptaplatin; heregulin; hexamethylene bisacetamide; hexestrol; human chorionic gonadotrophin; hydroxyurea; hydroxyurea (hydra); hypericin; ibandronic acid; ibritumomab; idarubicin; idarubicin (idamycin); idarubicin hydrochloride; idoxifene; idramantone; ifosfagemcitabine; ifosfamide; ifosfamide (iflex); ifosfamide with mesna (MAID); ilmofosine; ilomastat; imatinib mesylate; imidazoacridones; imiquimod; immunostimulant peptides; improsulfan tosylate; insulin-like growth factor-1 receptor inhibitor; interferon; interferon a; interferon a-2a; interferon a-2b; interferon agonists; interferon a-n1; interferon a-n3; interferon b-Ia; interferon g-1b; interferons; interleukin II (IL-2, including recombinant interleukin II or rIL2); interleukin II (including recombinant interleukin II or rIL2); interleukin-2; interleukins; iobenguane; iobenguane iobenguane; iododoxorubicin; ipomeanol; iproplatin; irinotecan; irinotecan (camptosar); irinotecan hydrochloride; irofulven; iroplact; irsogladine; isobengazole; isohomohalicondrin B; isotretinoin (accutane); itasetron; jasplakinolide; kahalalide F; ketoconazole; lamellarin-N triacetate; lanreotide; lanreotide acetate; leinamycin; lenalidomide; lenograstim; lentinan; lentinan sulfate; leptolstatin; letrozole; leucovorin; leukemia inhibiting factor; leukocyte alpha interferon; leuprolide; leuprolide acetate; leuprolide acetate (LHRH-analog); leuprolide+estrogen+progesterone; leuprorelin; levamisole; levamisole (ergamisol); liarozole; liarozole hydrochloride; linear polyamine analogue; lipophilic disaccharide peptide; lipophilic platinum compounds; lissoclinamide 7; lobaplatin; lombricine; lometrexol; lometrexol sodium; lomustine (CCNU or CeeNU); lonidamine; losoxantrone; losoxantrone hydrochloride; lovastatin; loxoribine; L-serine diazoacetate; lurtotecan; lutetium texaphyrin; lysofylline; lytic peptides: maitansine; mannomustine; mannostatin A; marimastat; masoprocol; maspin; matrilysin inhibitors; matrix metalloproteinase inhibitors; maytansine; mechlorethamine; mechlorethamine HCl (nitrogen mustard); medroxyprogesterone; medroxyprogesterone acetate (also called provera or depo provera); megestrol; megestrol acetate (menace); melphalan (ALKERAN®); MEN 10755; menogaril; mephalen; merbarone; mercaptopurine (purinethol); mercaptopurine anhydrous; MESNA; mesna (mesne); meterelin; methanesulfonic acid; methioninase; methotrexate (also called mtx); methotrexate sodium; methyl-ccnu; methyltestosterone; metoclopramide; metoprine; meturedepa; microalgal; MIF inhibitor; mifepristone; miltefosine; mimosine; mirimostim; mismatched double-stranded RNA; misonidazole; mithramycin; mitindomide; mitoantrone; mitobronitol; mitocarcin; mitocromin; mitogillin; mitoguazone; mitolactol; mitomalcin; mitomycin (MUTAMYCIN®); mitomycin analogues; mitomycin C; mitonafide; mitosper; mitotane; mitotane (also called o,p'-DDD or lysodren); mitotoxin fibroblast growth factor-saporin; mitoxantrone; mitoxantrone HCl (novantrone); mofarotene; molgramostim; mopidamol; multiple drug resistance gene inhibitor; multiple tumor suppressor 1-based therapy; mustard anticancer agent; mycaperoxide B; mycobacterial cell wall extract; mycophenolic acid; myriaporone; N-(1-methylethyl)-4-((2-methylhydrazino)methyl) benzamide; N-acetyldinaline; nafarelin; nagrestip; naloxone and pentazocine; napavin; naphterpin; nartograstim; nedaplatin; nelarabine; nemorubicin; neridronic acid; neutral endopeptidase; nicardipine; nilutamide (nilandron); nimustine; nisamycin; nitracrine; nitric oxide modulators; nitroxide antioxidant; nitrullyn; N-methyl-bis(2-chloroethyl)amine; nocodazole; nogalamycin; novobiocin; N-substituted benzamides; N,N-bis(2-chloroethyl)tetrahydro-2H-1,3,2-oxazaphosphorin-2-amine-2-oxide-; O6-benzylguanine; octreotide (sandostatin); okicenone; oligonucleotides; onapristone; ondansetron; oracin; oral cytokine inducer; ormnaplatin; osaterone; oxaliplatin; oxaunomycin; oxisuran; Paeliteet pactamycin; palauamine; palmitoylrhizoxin; pamidronic acid; panaxytriol; panomifene; parabactin; pazelliptine; pegaspargase (PEGx-1); peldesine; peliomycin; pemetrexed; pentamustine; pentosan polysulfate sodium; pentostatin (2'-deoxycoformycin); pentrozole; peplomycin; peplomycin sulfate; peptichemio; perflubron; perfosfamide; perillyl alcohol; phenazinomycin; phenylacetate; phosphatase inhibitors; photophoresis; picamycin (mithracin); picibanil; pilocarpine hydrochloride; pinafide; pipobroman; piposulfan; pirarubicin; piritrexim; piroxantrone hydrochloride; placetin A; placetin B; plasminogen activator inhibitor; platinum complex; platinum compounds; platinum-triamine complex; Plicamycin (also called mithramycin); plomestane; podofilox; podophyllotoxin; porfimer, porfimer sodium; porfirimer; prednimustine; prednisolone; prednisone; procarbazine; procarbazine HCl (matulane); profiromycin; propyl bis-acridone; prospidium; prostaglandin J2; proteasome inhibitors; protein A-based immune modulator; puromycin; puromycin aminonucleoside; puromycin hydrochloride; purpurins; PUVA (psoralen+ultraviolet a); pyran copolymer; pyrazofurin; pyrazoloacridine; pyridoxylated hemoglobin polyoxyethylene conjugate; raf antagonists; raltitrexed; ramosetron; ranimustine; rapamycin; ras farnesyl protein transferase inhibitors; ras inhibitors; ras-GAP inhibitor; rebeccamycin; retelliptine demethylated; rhenium Re 186 etidronate; rhizoxin; riboprine; ribozymes; RII retinamide; rituximab; rogletimide; rohitukine; romurtide; roquinimex; rubiginone B1; ruboxyl; safingol; safingol hydrochloride; saintopin; SarCNU; sarcophytol A; sargramostim; satraplatin; s-azacytidine; Sdi 1 mimetics; semustine; senescence derived inhibitor 1; sense oligonucleotides; sertenef; showdomycin; signal transduction modulators; single chain antigen-binding protein; sizofuran; sodium borocaptate; sodium phenylacetate; solverol; somatomedin binding protein; sonermin; sparfosate; sparfosate sodium; sparfosic acid; sparsomycin; spicamycin D; spirogermanium hydrochloride; spiromustine; splenopentin; spongistatin I; stem cell inhibitor, stem-cell division inhibitors; steroids; stipiamide; streptonigrin; streptozocin; streptozocin (zanosar); stromelysin inhibitors; sulfinosine; sulofenur; superactive vasoactive intestinal peptide antagonist; suradista; suramin; swainsonine; synthetic glycosaminoglycans; talisomycin; tallimustine; tamoxifen; tamoxifen citrate (nolvadex); tamoxifen methiodide; tasonermin; tauromustine; taxanes such as taxol and taxotere; TAXOL® (paclitaxel); taxon; TAXOTERE® (docetaxel); tazarotene; tecogalan; tecogalan sodium; tegafur, tellurapyrylium; telomerase inhibitors; teloxantrone; teloxantrone hydrochloride; temoporfin; temozolomide; teniposide; teniposide (also called VM-26 or vumon); tenuazonic acid; TEPA; teroxirone; testolactone; tetrachlorodecaoxide; tetrazomine; thaliblastine; thalidomide; thiamiprine; thiocoraline; thioguanine; thiotepa (thioplex); thrombopoietin; thrombopoietin mimetic; thymotrinan; thyroid stimulating hormone; tiazofurin; tilorone; tin ethyl etiopurpurin; tirapazamine; titanocene bichloride; topotecan; topsentin; toremifene; toremifene citrate; totipotent stein cell factor; Toxotere; translation inhibitors; trantuzumab; trastuzumab; trestolone; trestolone acetate; tretinoin (vesanoid); triacetyluridine; triaziquone; trichodermin; triciribine; triciribine phosphate; triethylene glycol diglycidyl ether; triethylenemelamine; triethylenephosphoramide; triethylenethiophosphoramide; trimetrexate (neutrexin); trimetrexate glucuronate; triptorelin; tris(1-aziridinyl)phosphine oxide; tris(1-aziridinyl)phosphine sulfide; tris(aziridinyl)-p-benzoquinone; trofosfamide; tropisetron; troxacitabine; tubulozole; tubulozole hydrochloride; turosteride; tyrosine kinase inhibitors; tyrphostins; UBC inhibitors; ubenimex; uracil mustard; uredepa; urogenital sinus-derived growth inhibitory factor, urokinase receptor antagonists; valrubicin; vapreotide; variolin B; vclaresol; veramine; Vercyte; verdins; verteporfin; vidarabine; vidarabine phosphate; vinblastine; vinblastine sulfate (velban); vinca alkaloids; vincristine or vincristine sulfate (ONCOVIN®); vindesine; vindesine sulfate; vinepidine; vinepidine sulfate; vinglycinate; vinglycinate sulfate; vinleurosine; vinleurosine sulfate; vinorelbine; vinorelbine tartrate (navelbine); vinrosidine; vinrosidine sulfate; vinxaltine; vinzolidine; vinzolidine sulfate; vitaxin; vorozole; zanoterone; zeniplatin; zilascorb; zinostatin; zinostatin stimalamer, zoledronate; zorubicin; zorubicin hydrochloride; and combinations thereof.

In a further embodiment, the TP-β/TXAS therapy is administered concurrently, subsequently and/or prior to one or more other anti-cancer therapies that is used in standard of care therapies for a particular cancer.

V. CANCER AND STANDARD OF CARE THERAPIES

Cancers and pre-cancerous conditions which can be prevented and/or treated by the methods described herein include, but are not limited to: adenofibroma; adenoma; agnogenic myeloid metaplasia; AIDS-Related Malignancies; ameloblastoma; anal cancer; angiofollicular mediastinal lymph node hyperplasia; angiokeratoma; angiolymphoid hyperplasia with eosinophilia; angiomatosis; anhidrotic ectodermal dysplasia; anterofacial dysplasia; apocrine metaplasia; apudoma; asphyxiating thoracic dysplasia; Astrocytoma (including, for example, cerebellar and cerebral); atriodigital dysplasia; atypical melanocytic hyperplasia; atypical metaplasia; autoparenchymatous metaplasia; basal cell hyperplasia; benign giant lymph node hyperplasia; bile duct cancer (including, for example, extrahepatic bile duct cancer); bladder cancer; bone cancer; brain tumor (including, for example, brain stem glioma, cerebellar astrocytoma glioma, malignant glioma, supratentorial primitive neuroectodermal tumors, visual pathway and hypothalamic glioma, ependymoma, medulloblastoma, gestational trophoblastic tumor glioma, and paraganglioma); branchionia; breast cancer (male and female); bronchial adenomas/carcinoids; bronchopulmonary dysplasia; cancer or pre-cancerous growths or metastatic growths of epithelial cells; carcinoid heart disease; carcinoid tumor (including, for example, gastrointestinal); carcinoma (including, for example, unknown primary origin, adrenocortical, islet cells, adeno-, adeoncortical, basal cell, basosquamous, bronchiolar, Brown-Pearce, cystadeno-, ductal, hepato-, Krebs, papillary, oat cell, small cell lung, non-small cell lung, squamous cell, transitional cell, Walker, Merkel Cell, and skin carcinomas); cementoma; cementum hyperplasia; cerebral dysplasia; cervical cancer; cervical dysplasia; cholangioma; cholesteatoma; chondroblastoma; chondroectodermal dysplasia; chordoma; choristoma; chrondroma; cleidocranial dysplasia; colon cancer; colorectal cancer; colorectal/local metastasized colorectal cancer; congenital adrenal hyperplasia; congenital ectodermal dysplasia; congenital sebaceous hyperplasia; connective tissue metaplasia; craniocarpotarsal dysplasia; craniodiaphysial dysplasia; craniometaphysial dysplasia; craniopharyngioma; cylindroma; cystadenoma; cystic hyperplasia (including, for example, cystic hyperplasia of the breast); cystosarconia phyllodes; dentin dysplasia; denture hyperplasia; diaphysial dysplasia;

ductal hyperplasia; dysgenninoma; dysplasia epiphysialis hemimelia; dysplasia epiphysialis multiplex; dysplasia epiphysialis punctata; ectodermal dysplasia; Ehrlich tumor; enamel dysplasia; encephalo-ophthalmic dysplasia; endometrial cancer (including, for example, Ependymoma and endometrial hyperplasia); ependymoma; epithelial cancer; epithelial dysplasia; epithelial metaplasia; esophageal cancer; Ewing's Family of tumors (including, for example, Ewing sarcoma); extrahepatic bile duct cancer; eye cancer (including, for example, intraocular melanoma and retinoblastoma); faciodigitogenital dysplasia; familial fibrous dysplasia of jaws; familial white folded dysplasia; fibroma; fibromuscular dysplasia; fibromuscular hyperplasia; fibrous dysplasia of bone; florid osseous dysplasia; focal epithelial hyperplasia; gall bladder cancer; ganglioneuroma; gastric cancer (for example, stomach cancer); gastrointestinal carcinoid tumor; gastrointestinal tract cancer; gastrointestinal tumors; Gaucher's disease; germ cell tumors (including, for example, extracranial, extragonadal, and ovarian germ cell tumors); giant cell tumor; gingival hyperplasia; glioblastoma; glomangioma; granulosa cell tumor; gynandroblastoma; hamartoma; head and neck cancer; hemangioendothelioma; hemangioma; hemangiopericytoma; hepatocellular cancer; hepatoma; hereditary renal-retinal dysplasia; hidrotic ectodermal dysplasia; histiocytonia; histiocytosis; hypergammaglobulinemia; hypohidrotic ectodermal dysplasia; hypopharyngeal cancer; inflammatory fibrous hyperplasia; inflammatory papillary hyperplasia; intestinal cancers; intestinal metaplasia; intestinal polyps; intraocular melanoma; intravascular papillary endothelial hyperplasia; kidney cancer; laryngeal cancer; leiomyoma; leukemia (including, for example, acute and chronic forms of: lymphoblastic, lymphocytic, myeloid, myelogenous, Hairy Cell, B-cell, T-cell, and HTLV leukemias); Leydig cell tumor; lip and oral cavity cancer; lipoma; liver cancer; lung cancer (including, for example, small cell and non-small cell); lymphangiomyoma; lymphaugioma; lymphoma (including, for example, AIDS-Related, central nervous system (primary), Hodgkin's during pregnancy, Non-Hodgkin's, Hodgkin's, Non-Hodgkin's during pregnancy, primary central nervous system, mast cell, B-cell, adeno, Burkitt's, cutaneous T-Cell, large cell, and small cell lymphomas); lymphopenic thymic dysplasia; lymphoproliferative disorders; macroglobulinemia (including, for example, Waldenstrom's macroglobulinemia); malignant carcinoid syndrome; malignant mesothelioma; malignant thymoma; mammary dysplasia; mandibulofacial dysplasia; medulloblastoma; meningioma; mesenchymoma; mesonephroma; mesothelioma (including, for example, malignant mesothelioma); metaphysial dysplasia; metaplastic anemia; metaplastic ossification; metaplastic polyps; metastatic squamous neck cancer (for example, with Occult Primary); Mondini dysplasia; monostotic fibrous dysplasia; mucoepithelial dysplasia; multiple endocrine neoplasia syndrome; multiple epiphysial dysplasia; multiple myeloma/plasma cell neoplasm; mycosis fungoides; myelodysplastic syndrome; myeloid metaplasia; myeloproliferative disorders (including, for example, chronic myeloproliferative disorders); myoblastoma; myoma; myxoma; nasal cavity and paranasal sinus cancer; nasopharyngeal cancer; neoplasms located in the: prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital tract; neurilemmoma; neuroblastoma; neuroepithelioma; neurofibroma; neurofibromatosis; neuroma; nodular hyperplasia of prostate; nodular regenerative hyperplasia; oculoauriculovertebral dysplasia; oculodentodigital dysplasia; oculovertebral dysplasia; odontogenic dysplasia; odontoma; opthalmomandibulomelic dysplasia; oropharyngeal cancer; osteoma; ovarian cancer (including, for example, ovarian epithelial cancer and ovarian low malignant potential tumor); pancreatic cancer (including, for example islet cell and exocrine pancreatic cancers); papilloma; paraganglionia. nonchromaffin; paranasal sinus and nasal cavity cancer; paraproteinemias; parathyroid cancer; periapical cemental dysplasia; pheochromocytoma (including, for example, penile cancer); pineal and supratentorial primitive neuroectodermal tumors; pinealoma; pituitary tumor; plasma cell neoplasm/multiple myeloma; plasmacytoma; pleuropulmonary blastoma; polyostotic fibrous dysplasia; polyps; pregnancy cancer; pre-neoplastic disorders including but not limited to benign dysproliferative disorders such as benign tumors, fibrocystic conditions, tissue hypertrophy, intestinal polyps, colon polyps, esophageal dysplasia, leukoplakia, keratoses, Bowen's disease, Farmer's Skin, solar cheilitis, and solar keratosis); primary hepatocellular cancer; primary liver cancer; primary myeloid metaplasia; prostate cancer; pseudoachondroplastic spondyloepiphysial dysplasia; pseudoepitheliomatous hyperplasia; purpura; rectal cancer; renal cancer (including, for example, kidney cancer, renal pelvis and ureter cancer, transitional cell cancer of the renal pelvis and ureter, ureter cancer); reticuloendotheliosis; retinal dysplasia; retinoblastoma; salivary gland cancer; sarcomas (including, for example, uterine, soft tissue, carcino-, chondro-, fibro-, hemangio-, Kaposi's, leiomyo, lipo-, lymphangio-, myo-, myxo-, Rhabdo-, sarcoidosis, osteo-, and Ewing sarcomas as well as malignant fibrous histiocytoma of bone and clear cell sarcoma of tendon sheaths); sclerosing angioma; secondary myeloid metaplasia; senile sebaceous hyperplasia; septo-optic dysplasia; Sertoli cell tumor; Sezary Syndrome; skin cancer (for example, including melanoma and non-melanoma skin cancer); small intestine cancer; spondyloepiphysial dysplasia; squamous metaplasia (for example, squamous metaplasia of amnion); stomach cancer; supratentorial primitive neuroectodermal and pineal tumors; supratentorial primitive neuroectodermal tumors; symptomatic myeloid metaplasia; teratoma; testicular cancer; theca cell tumor; thymoma (including, for example, malignant thymoma); thyroid Cancer; trophoblastic tumors (including for example gestational trophoblastic tumors); ureter cancer; urethral cancer; uterine cancer; vaginal cancer; ventriculoradial dysplasia; verrucous hyperplasia; vulvar cancer; Waldenstrom's macroglobulinemia; and Wilms' tumor.

In a particular embodiment, the cancer is renal cell carcinoma, prostate, breast, colorectal, bladder, stomach, kidney, pancreatic or lung cancer. In a further embodiment, the cancer is renal cell carcinoma, prostate, breast, colorectal or bladder cancer. In another embodiment, the cancer is a genitourinary cancer, gastrointestinal cancer or hematopoietic cancer.

As discussed above, the present invention involves the treatment of various cancers using TP-β antagonists and/or TXAS inhibitors, optionally in combination with other treatments known as the "standard of care" in oncology. As discussed below, a variety of different treatments are applied to cancers that are characterized by TP-β overexpression.

A. Genitourinary Cancer i. Bladder Cancer

The treatment of bladder cancer depends on how deep the tumor invades into the bladder wall. Superficial tumors (those not entering the muscle layer) can be "shaved off" using an electrocautery device attached to a cystoscope.

Immunotherapy in the form of BCG instillation is also used to treat and prevent the recurrence of superficial tumors. BCG immunotherapy is effective in up to ⅔ of the cases at this stage. Instillations of chemotherapy into the bladder can also be used to treat superficial disease. Bacillus Calmette-Guerin (BCG) has been in use since the 1980's, and is the most proven and effective form of immunotherapy at this point in time. BCG is an inactivated form of the bacterium *Mycobacterium tuberculosis*, which is given both intravesically mixed in a saline solution and instilled directly into the bladder via a catheter, as well as in the form of a percutaneous vaccine. Although it is not yet totally understood why BCG and other immunotherapies work against cancer, they are thought to elicit an immune response.

It has been shown that BCG induces a variety of cytokines into the urine of patients with superficial TCC, and that some cytokines have anti-angiogenic activity. One study demonstrated that interferon-inducible protein 10 (IP-10) and its inducing anti-angiogenic cytokines, interferon-γ and interleukin-12, are increased during intravesical BCG immunotherapy of bladder TCC. These data suggest that, in addition to a cellular immune response, BCG may induce a cytokine-mediated anti-angiogenic environment that aids in inhibiting future tumor growth and progression.

Though side effects vary with the individual, the great majority of people find BCG treatments tolerable with side effects being temporary, and some have no adverse reactions at all. Dysuria (pain or difficulty upon urination) and urinary frequency are expected as a consequence of the inflammatory response, and cystitis is the most frequent adverse reaction-occurring in up to 90% of cases. Blood in the urine may occur with cystitis and is seen in one-third of patients. Irritative bladder symptoms are unlikely in the week after the first intravesical BCG. Side effects of BCG are cumulatory, and generally increase with successive treatments. Some people complain of flu like symptoms including fatigue, joint pain and muscle ache.

Untreated, superficial tumors may gradually begin to infiltrate the muscular wall of the bladder. Tumors that infiltrate the bladder require more radical surgery where part or all of the bladder is removed (a cystectomy) and the urinary stream is diverted. In some cases, skilled surgeons can create a substitute bladder (a neobladder) from a segment of intestinal tissue, but this largely depends upon patient preference, age of patient, renal function, and the site of the disease.

A combination of radiation and chemotherapy can also be used to treat invasive disease. It has not yet been determined how the effectiveness of this form of treatment compares to that of radical ablative surgery. There is weak observational evidence from one very small study (n=84) to suggest that the concurrent use of statins is associated with failure of BCG immunotherapy.

ii. Renal Cancer

If only the kidneys are involved, which is about 40% of cases, it can be cured roughly 90% of the time with surgery. If it has spread outside of the kidneys, often into the lymph nodes or the main vein of the kidney, then it must be treated with chemotherapy and other treatments.

Surgical removal of all or part of the kidney (nephrectomy) is recommended. This may include removal of the adrenal gland, retroperitoneal lymph nodes, and possibly tissues involved by direct extension (invasion) of the tumor into the surrounding tissues. In cases where the tumor has spread into the renal vein, inferior vena cava, and possibly the right atrium (angioinvasion), this portion of the tumor can be surgically removed, as well. In case of metastases surgical resection of the kidney ("cytoreductive nephrectomy") may improve survival, as well as resection of a solitary metastatic lesion.

Percutaneous, image-guided therapies, usually managed by radiologists, are being offered to patients with localized tumor, but who are not good candidates for a surgical procedure. This sort of procedure involves placing a probe through the skin and into the tumor using real-time imaging of both the probe tip and the tumor by computed tomography, ultrasound, or even magnetic resonance imaging guidance, and then destroying the tumor with heat (radiofrequency ablation) or cold (cryotherapy). These modalities are at a disadvantage compared to traditional surgery in that pathologic confirmation of complete tumor destruction is not possible.

Radiation therapy is not commonly used for treatment of renal cell carcinoma because it is usually not successful. Radiation therapy may be used to palliate the symptoms of skeletal metastases.

Medications such as α-interferon and interleukin-2 (IL-2) have been successful in reducing the growth of some renal cell carcinomas, including some with metastasis. Studies have demonstrated that IL-2 offers the possibility of a complete and long-lasting remission in these diseases. In addition, the anti-VEGF monoclonal antibody bevacizumab has been shown to be promising in advanced disease.

Sorafenib (Nexavar) was FDA approved in December 2005 for treatment of advanced renal cell cancer, the first receptor tyrosine kinase (RTK) inhibitor indicated for this use Sunitinib, an oral, small-molecule, multi-targeted (RTK) inhibitor, and sorafenib both interfere with tumor growth by inhibiting angiogenesis as well as tumor cell proliferation. Sunitinib appears to offer greater potency against advanced RCC, perhaps because it inhibits more receptors than sorafenib. However, these agents have not been directly compared against one another in a single trial. Temsirolimus (CCI-779) is an inhibitor of mTOR kinase (mammalian target of rapamycin) that was shown to prolong overall survival versus interferon-α2b in patients with previously untreated metastatic renal cell carcinoma with three or more poor prognostic features.

Chemotherapy may be used in some cases, but cure is unlikely unless all the cancer can be removed with surgery.

In November 2006, it was announced that a vaccine had been developed and tested with very promising results. The new vaccine, called TroVax, works by harnessing the patient's own immune system to fight the disease.

iii. Prostate Cancer

Prostate cancer can be treated with surgery, radiation therapy, hormonal therapy, occasionally chemotherapy, proton therapy, or some combination of these. The age and underlying health of the man as well as the extent of spread, appearance under the microscope, and response of the cancer to initial treatment are important in determining the outcome of the disease. Since prostate cancer is a disease of older men, many will die of other causes before a slowly advancing prostate cancer can spread or cause symptoms. This makes treatment selection difficult. The decision whether or not to treat localized prostate cancer (a tumor that is contained within the prostate) with curative intent is a patient trade-off between the expected beneficial and harmful effects in terms of patient survival and quality of life.

Watchful waiting, also called "active surveillance," refers to observation and regular monitoring without invasive treatment. Watchful waiting is often used when an early stage, slow-growing prostate cancer is found in an older man. Watchful waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.). Most men who choose watchful waiting for early stage tumors eventually have signs of tumor progression, and they may need to begin treatment within three years. Although men who choose watchful waiting avoid the risks of surgery and radiation, the risk of metastasis (spread of the cancer) may be increased. For younger men, a trial of active surveillance may not mean avoiding treatment altogether, but may reasonably allow a delay of a few years or more, during which time the quality of life impact of active treatment can be avoided. Published data to date suggest that carefully selected men will not miss a window for cure with this approach. Additional health problems that develop with advancing age during the observation period can also make it harder to undergo surgery and radiation therapy.

Clinically insignificant prostate tumors are often found by accident when a doctor incorrectly orders a biopsy not following the recommended guidelines (abnormal DRE and elevated PSA). The urologist must check that the PSA is not elevated for other reasons, prostatitis, etc. An annual biopsy is often recommended by a urologist for a patient who has selected watchful waiting when the tumor is clinically insignificant (no abnormal DRE or PSA). The tumors tiny size can be monitored this way and the patient can decide to have surgery only if the tumor enlarges which may take many years or never.

Surgical removal of the prostate, or prostatectomy, is a common treatment either for early stage prostate cancer, or for cancer which has failed to respond to radiation therapy. The most common type is radical retropubic prostatectomy, when the surgeon removes the prostate through an abdominal incision. Another type is radical perineal prostatectomy, when the surgeon removes the prostate through an incision in the perineum, the skin between the scrotum and anus. Radical prostatectomy can also be performed laparoscopically, through a series of small (1 cm) incisions in the abdomen, with or without the assistance of a surgical robot.

Radical prostatectomy is effective for tumors which have not spread beyond the prostate; cure rates depend on risk factors such as PSA level and Gleason grade. However, it may cause nerve damage that significantly alters the quality of life of the prostate cancer survivor. The most common serious complications are loss of urinary control and impotence. Reported rates of both complications vary widely depending on how they are assessed, by whom, and how long after surgery, as well as the setting (e.g., academic series versus community-based or population-based data). Although penile sensation and the ability to achieve orgasm usually remain intact, erection and ejaculation are often impaired. Medications such as sildenafil (Viagra), tadalafil (Cialis), or vardenafil (Levitra) may restore some degree of potency. For most men with organ-confined disease, a more limited "nerve-sparing" technique may help avoid urinary incontinence and impotence.

Radical prostatectomy has traditionally been used alone when the cancer is small. In the event of positive margins or locally advanced disease found on pathology, adjuvant radiation therapy may offer improved survival. Surgery may also be offered when a cancer is not responding to radiation therapy. However, because radiation therapy causes tissue changes, prostatectomy after radiation has a higher risk of complications.

Transurethral resection of the prostate, commonly called a "TURP," is a surgical procedure performed when the tube from the bladder to the penis (urethra) is blocked by prostate enlargement. TURP is generally for benign disease and is not meant as definitive treatment for prostate cancer. During a TURP, a small tube (cystoscope) is placed into the penis and the blocking prostate is cut away.

In metastatic disease, where cancer has spread beyond the prostate, removal of the testicles (called orchiectomy) may be done to decrease testosterone levels and control cancer growth.

Radiation therapy, also known as radiotherapy, uses ionizing radiation to kill prostate cancer cells. When absorbed in tissue, ionizing radiation such as γ and x-rays damage the DNA in cells, which increases the probability of apoptosis. Two different kinds of radiation therapy are used in prostate cancer treatment: external beam radiation therapy and brachytherapy.

External beam radiation therapy uses a linear accelerator to produce high-energy x-rays which are directed in a beam towards the prostate. A technique called Intensity Modulated Radiation Therapy (IMRT) may be used to adjust the radiation beam to conform with the shape of the tumor, allowing higher doses to be given to the prostate and seminal vesicles with less damage to the bladder and rectum. External beam radiation therapy is generally given over several weeks, with daily visits to a radiation therapy center. New types of radiation therapy may have fewer side effects then traditional treatment, one of these is Tomotherapy.

Permanent implant brachytherapy is a popular treatment choice for patients with low to intermediate risk features, can be performed on an outpatient basis, and is associated with good 10-year outcomes with relatively low morbidity. It involves the placement of about 100 small "seeds" containing radioactive material (such as iodine$^{125}$ or palladium$^{103}$) with a needle through the skin of the perineum directly into the tumor while under spinal or general anesthetic. These seeds emit lower-energy X-rays which are only able to travel a short distance. Although the seeds eventually become inert, they remain in the prostate permanently. The risk of exposure to others from men with implanted seeds is generally accepted to be insignificant.

Radiation therapy is commonly used in prostate cancer treatment. It may be used instead of surgery for early cancers, and it may also be used in advanced stages of prostate cancer to treat painful bone metastases. Radiation treatments also can be combined with hormonal therapy for intermediate risk disease, when radiation therapy alone is less likely to cure the cancer. Some radiation oncologists combine external beam radiation and brachytherapy for intermediate to high risk situations. One study found that the combination of six months of androgen suppressive therapy combined with external beam radiation had improved survival compared to radiation alone in patients with localized prostate cancer. Others use a "triple modality" combination of external beam radiation therapy, brachytherapy, and hormonal therapy.

Less common applications for radiotherapy are when cancer is compressing the spinal cord, or sometimes after surgery, such as when cancer is found in the seminal vesicles, in the lymph nodes, outside the prostate capsule, or at the margins of the biopsy.

Radiation therapy is often offered to men whose medical problems make surgery more risky. Radiation therapy appears to cure small tumors that are confined to the prostate just about as well as surgery. However, as of 2006 some issues remain unresolved, such as whether radiation should be given to the rest of the pelvis, how much the absorbed dose should be, and whether hormonal therapy should be given at the same time.

Side effects of radiation therapy might occur after a few weeks into treatment. Both types of radiation therapy may cause diarrhea and rectal bleeding due to radiation proctitis, as well as urinary incontinence and impotence. Symptoms tend to improve over time. Men who have undergone external beam radiation therapy will have a higher risk of later developing colon cancer and bladder cancer.

Cryosurgery is another method of treating prostate cancer. It is less invasive than radical prostatectomy, and general anesthesia is less commonly used. Under ultrasound guidance, metal rods are inserted through the skin of the perineum into the prostate. Highly purified Argon gas is used to cool the rods, freezing the surrounding tissue at −196° C. (−320° F.). As the water within the prostate cells freeze, the cells die. The urethra is protected from freezing by a catheter filled with warm liquid. Cryosurgery generally causes fewer problems with urinary control than other treatments, but impotence occurs up to ninety percent of the time. When used as the initial treatment for prostate cancer and in the hands of an experienced cryosurgeon, cryosurgery has a 10 year biochemical disease free rate superior to all other treatments including radical prostatectomy and any form of radiation Cryosurgery has also been demonstrated to be superior to radical prostatectomy for recurrent cancer following radiation therapy.

Hormonal therapy uses medications or surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. Hormonal therapy is therefore usually used when cancer has spread from the prostate. It may also be given to certain men undergoing radiation therapy or surgery to help prevent return of their cancer.

Hormonal therapy for prostate cancer targets the pathways the body uses to produce DHT. A feedback loop involving the testicles, the hypothalamus, and the pituitary, adrenal, and prostate glands controls the blood levels of DHT. First, low blood levels of DHT stimulate the hypothalamus to produce gonadotropin releasing hormone (GnRH). GnRH then stimulates the pituitary gland to produce luteinizing hormone (LH), and LH stimulates the testicles to produce testosterone. Finally, testosterone from the testicles and dehydroepiandrosterone from the adrenal glands stimulate the prostate to produce more DHT. Hormonal therapy can decrease levels of DHT by interrupting this pathway at any point.

There are several forms of hormonal therapy. Orchiectomy is surgery to remove the testicles. Because the testicles make most of the body's testosterone, after orchiectomy testosterone levels drop. Now the prostate not only lacks the testosterone stimulus to produce DHT, but also it does not have enough testosterone to transform into DHT.

Anti-androgens are medications such as flutamide, bicalutamide, nilutamide, and cyproterone acetate which directly block the actions of testosterone and DHT within prostate cancer cells.

Medications which block the production of adrenal androgens such as DHEA include ketoconazole and aminoglutethimide. Because the adrenal glands only make about 5% of the body's androgens, these medications are generally used only in combination with other methods that can block the 95% of androgens made by the testicles. These combined methods are called total androgen blockade (TAB). TAB can also be achieved using anti-androgens.

GnRH action can be interrupted in one of two ways. GnRH antagonists suppress the production of LH directly, while GnRH agonists suppress LH through the process of down-regulation after an initial stimulation effect. Abarelix is an example of a GnRH antagonist, while the GnRH agonists include leuprolide, goserelin, triptorelin, and buserelin. Initially, GnRH agonists increase the production of LH. However, because the constant supply of the medication does not match the body's natural production rhythm, production of both LH and GnRH decreases after a few weeks.

As of 2006 the most successful hormonal treatments are orchiectomy and GnRH agonists. Despite their higher cost, GnRH agonists are often chosen over orchiectomy for cosmetic and emotional reasons. Eventually, total androgen blockade may prove to be better than orchiectomy or GnRH agonists used alone.

Each treatment has disadvantages which limit its use in certain circumstances. Although orchiectomy is a low-risk surgery, the psychological impact of removing the testicles can be significant. The loss of testosterone also causes hot flashes, weight gain, loss of libido, enlargement of the breasts (gynecomastia), impotence and osteoporosis. GnRH agonists eventually cause the same side effects as orchiectomy but may cause worse symptoms at the beginning of treatment. When GnRH agonists are first used, testosterone surges can lead to increased bone pain from metastatic cancer, so anti-androgens or abarelix are often added to blunt these side effects. Estrogens are not commonly used because they increase the risk for cardiovascular disease and blood clots. The anti-androgens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer.

Bone pain due to metastatic disease is treated with opioid pain relievers such as morphine and oxycodone. External beam radiation therapy directed at bone metastases may provide pain relief. Injections of certain radioisotopes, such as strontium-89, phosphorus-32, or samarium-153, also target bone metastases and may help relieve pain.

High Intensity Focused Ultrasound (HIFU) for prostate cancer utilizes ultrasonic waves to ablate/destroy the tissue of the prostate. During the HIFU procedure, sound waves are used to heat the prostate tissue thus destroying the cancerous cells. Essentially, ultrasonic waves are precisely focused on specific areas of the prostate to eliminate the prostate cancer with minimal risks of effecting other tissue or organs. Temperatures at the focal point of the sound waves can exceed 100° C. The ability to focus the ultrasonic waves leads to a relatively low occurrence of both incontinence and impotence. (0.6% and 0-20%, respectively). According to international studies, when compared to other procedures, HIFU has a high success rate with a reduced risk of side effects. Studies using the Sonablate 500 HIFU machine have shown that 94% of patients with a pretreatment PSA (Prostate Specific Antigen) of less than 10 g/ml were cancer-free after three years. However, many studies of HIFU were performed by manufacturers of HIFU devices, or members of manufacturers' advisory panels.

HIFU was first used in the 1940's and 1950's in efforts to destroy tumors in the central nervous system. Since then, HIFU has been shown to be effective at destroying malignant tissue in the brain, prostate, spleen, liver, kidney, breast, and bone. Today, the HIFU procedure for prostate cancer is performed using a transrectal probe. This procedure has been performed for over ten years and is currently approved for use in Japan, Europe, Canada, and parts of Central and South America.

Although not yet approved for use in the Unites States, many patients have received the HIFU procedure at facilities in Canada, and Central and South America. Currently, therapy is available using the Sonablate 500 or the Ablatherm. The Sonablate 500 is designed by Focus Surgery of Indianapolis, Ind. and is used in international HIFU centers around the world.

Several medications and vitamins may also help prevent prostate cancer. Two dietary supplements, vitamin E and selenium, may help prevent prostate cancer when taken daily. Estrogens from fermented soybeans and other plant sources (called phytoestrogens) may also help prevent prostate cancer. The selective estrogen receptor modulator drug toremifene has shown promise in early trials. Two medications which block the conversion of testosterone to dihydrotestosterone, finasteride and dutasteride, have also shown some promise. As of 2006 the use of these medications for primary prevention is still in the testing phase, and they are not widely used for this purpose. The problem with these medications is that they may preferentially block the development of lower-grade prostate tumors, leading to a relatively greater chance of higher grade cancers, and negating any overall survival improvement. Green tea may be protective (due to its polyphenol content), though the data is mixed. A 2006 study of green tea derivatives demonstrated promising prostate cancer prevention in patients at high risk for the disease. In 2003, an Australian research team led by Graham Giles of The Cancer Council Australia concluded that frequent masturbation by males appears to help prevent the development of prostate cancer. Recent research published in the Journal of the National Cancer Institute suggests that taking multivitamins more than seven times a week can increase the risks of contracting the disease. This research was unable to highlight the exact vitamins responsible for this increase (almost double), although they suggest that vitamin A, vitamin E and beta-carotene may lie at its heart. It is advised that those taking multivitamins never exceed the stated daily dose on the label. Scientists recommend a healthy, well balanced diet rich in fiber, and to reduce intake of meat. A 2007 study published in the Journal of the National Cancer Institute found that men eating cauliflower, broccoli, or one of the other cruciferous vegetables, more than once a week were 40% less likely to develop prostate cancer than men who rarely ate those vegetables. Scientists believe the reason for this phenomenon has to do with a phytochemical called Diindolylmethane in these vegetables that has anti-androgenic and immune modulating properties. This compound is currently under investigation by the National Cancer Institute as a natural therapeutic for prostate cancer.

B. Gastrointestinal Cancers i. Colorectal Cancers

Treatment of colorectal cancer depends heavily on the stage. When caught at early stages, it can be curable, but when detected later, it is less likely to be curable. Surgery remains the primary treatment while chemotherapy and/or radiotherapy may be recommended depending on the individual patient's staging and other medical factors.

Surgeries can be categorised into curative, palliative, bypass, fecal diversion, or open-and-close. Curative treatment can be offered if the tumor is localized, such as by removing a polyp at the time of colonoscopy. In colon cancer, a more advanced tumor typically requires surgical removal of the section of colon containing the tumor with sufficient margins, and radical en-bloc resection of mesentery and lymph nodes to reduce local recurrence (i.e., colectomy). If possible, the remaining parts of colon are anastomosed together to create a functioning colon. In cases when anastomosis is not possible, a stoma (artificial orifice) is created. Curative surgery on rectal cancer includes total mesorectal excision (anterior resection) or abdominoperineal excision.

In case of multiple metastases, palliative (non-curative) resection of the primary tumor is still offered in order to reduce further morbidity caused by tumor bleeding, invasion, and its catabolic effect. Surgical removal of isolated liver metastases is, however, common and may be curative in selected patients; improved chemotherapy has increased the number of patients who are offered surgical removal of isolated liver metastases. If the tumor has invaded adjacent vital structures, making excision technically difficult, the surgeons may prefer to bypass the tumor (ileotransverse bypass) or to do a proximal fecal diversion through a stoma.

Chemotherapy is used to reduce the likelihood of metastasis developing, shrink tumor size, or slow tumor growth. Chemotherapy is often applied after surgery (adjuvant), before surgery (neo-adjuvant), or as the primary therapy if surgery is not indicated (palliative). Adjuvant (post-surgery) chemotherapy includes the combination of infusional 5-fluorouracil, leucovorin, and oxaliplatin (FOLFOX®)

Chemotherapy for metastatic disease is commonly used as first line treatment and involves the combination of infusional 5-fluorouracil, leucovorin, and oxaliplatin (FOLFOX®) with bevacizumab or infusional 5-fluorouracil, leucovorin, and irinotecan (FOLFIRI®) with bevacizumab. Other drugs include Cetuximab (ERBITUX®), Panitumumab VECTIBIX®), Bortezomib (VELCADE®), Oblimersen (GENASENSE®, G3139), Gefitinib and Erlotinib (TARCEVA®), and Topotecan (HYCAMTIN®).

Radiotherapy is not used routinely in colon cancer, as it could lead to radiation enteritis, and it is difficult to target specific portions of the colon. It is more common for radiation to be used in rectal cancer, since the rectum does not move as much as the colon and is thus easier to target. Sometimes chemotherapy agents are used to increase the effectiveness of radiation by sensitizing tumor cells if present.

In November 2006, it was announced that a vaccine had been developed and tested with very promising results. The vaccine, called TroVax, works in a totally different way to existing treatments by harnessing the patient's own immune system to fight the disease. Experts say this suggests that gene therapy vaccines could prove an effective treatment for a whole range of cancers. Oxford BioMedica is a British spin-out from Oxford University specialising in the development of gene-based treatments. Phase III trials are underway for renal cancers and planned for colon cancers.

ii. Pancreatic Cancer

Treatment of pancreatic cancer depends on the stage of the cancer. Recent advances have made possible resection (surgical removal) of tumors that were previously unresectable due to blood vessel involvement. The Whipple procedure is the most common surgical treatment for cancers involving the head of the pancreas.

Fluorouracil, gemcitabine, and erlotinib are the chemotherapeutic drug agents of choice. Gemcitabine was approved by the FDA in 1998 after a clinical trial reported improvements in quality of life in patients with advanced prostate cancer. This marked the first FDA approval of a chemotherapy drug for a non-survival clinical trial endpoint.

In addition, the FDA has licensed the use of erlotinib (Tarceva) in combination with gemcitabine as a palliative agent for pancreatic cancer. This trial compared the action of gemcitabine/erlotinib vs gemcitabine/placebo and demonstrated modestly improved survival rates, improved tumour response and improved progression free survival rates.

iii. Stomach Cancer

Cancer of the stomach is difficult to cure unless it is found in an early stage. Unfortunately, because early stomach cancer causes few symptoms, the disease is usually advanced when the diagnosis is made. Treatment for stomach cancer may include surgery, chemotherapy, and/or radiation therapy, and more recently biological therapy.

Surgery is the most common treatment for stomach cancer. The surgeon removes part (subtotal or partial gastrectomy) or all (total gastrectomy) of the stomach, as well as some of the tissue around the stomach, with the basic goal of removing all cancer and a margin of normal tissue. Depending on the extent of invasion and the location of the tumor, surgery may also include removal of part of the esophagus, spleen, ovaries, intestine or pancreas. Endoscopic mucosal resection is a treatment for early gastric cancer that has been pioneered in Japan, but is available in the United States at some centers. In this procedure, the tumor is removed from the wall of the stomach using an endoscope, with the advantage in that it is a smaller operation than removing the stomach. Surgical interventions are currently curative in less than 40% of cases, and, in cases of metastasis, may only be palliative.

Unfortunately, gastric cancer has not been especially sensitive to these drugs until recently, and historically served to palliatively reduce the size of the tumor and increase survival time. Some drugs used in stomach cancer treatment include: 5-FU (fluorouracil), BCNU (carmustine), methyl-CCNU (Semustine), and doxorubicin (Adriamycin), as well as Mitomycin C, and more recently cisplatin and taxotere in various combinations. Radiation therapy is generally used in combination with surgery and chemotherapy, or used only with chemotherapy in cases where the individual is unable to undergo surgery. Radiation therapy may be used to relieve pain or blockage by shrinking the tumor for palliation of incurable disease.

C. Leukemias i. Acute Myelogenous Leukemia (AML)

AML is most common for adults; more men than women are affected. Many different chemotherapeutic plans are available for the treatment of AML. Overall, the strategy is to control bone marrow and systemic (whole-body) disease while offering specific treatment for the central nervous system (CNS), if involved. In general, most oncologists rely on combinations of drugs for the initial, induction phase of chemotherapy. Such combination chemotherapy usually offers the benefits of early remission (lessening of the disease) and a lower risk of disease resistance. Consolidation or "maintenance" treatments may be given to prevent disease recurrence once remission has been achieved. Consolidation treatment often entails a repetition of induction chemotherapy or the intensification chemotherapy with added drugs. By contrast, maintenance treatment involves drug doses that are lower than those administered during the induction phase.

In addition, specific treatment plans may be used, depending on the type of leukemia that has been diagnosed. Whatever the plan, it is important for the patient to understand the treatment that is being given and the decision-making process behind the choice.

Initial treatment of AML usually begins with induction chemotherapy using a combination of drugs such as daunorubicin (DNR), cytarabine (ara-C), idarubicin, thioguanine, etoposide, or mitoxantrone, anabolic steroids.

Follow-up therapy for such patients may involve supportive care, such as intravenous nutrition and treatment with oral antibiotics (e.g., ofloxacin, rifampin), especially in patients who have prolonged granulocytopenia; that is too few mature granulocytes (neutrophils), the bacteria-destroying white blood cells that contain small particles, or granules (<100 granulocytes per cubic millimeter for 2 weeks); injection with colony-stimulating factors such as granulocyte colony-stimulating factor (G-CSF), which may help to shorten the period of granulocytopenia that results from induction therapy; transfusions with red blood cells and platelets Patients with newly diagnosed disease also may be considered for stem cell transplantation (SCT), either from the bone marrow or other sources. Allogeneic bone marrow transplant (alloBMT) is reserved primarily for patients under 55 years of age who have a compatible family donor. Approximately half of newly diagnosed AML patients are in this age group, with 75% achieving a complete remission (CR) after induction and consolidation therapy. Allogeneic bone marrow transplant is available for about 15% of all patients with AML. Unfortunately, it is estimated that only 7% of all AML patients will be cured using this procedure.

People who receive stem cell transplantation (SCT, alloBMT) require protective isolation in the hospital, including filtered air, sterile food, and sterilization of the microorganisms in the gut, until their total white blood cell (WBC) count is above 500.

Treatment of central nervous system leukemia, if present, may involve injection of chemotherapeutic drugs (e.g., cytarabine or ara-C, methotrexate) into the areas around the brain and spinal cord.

Once the patient is in remission, he or she will receive consolidation or maintenance therapy, for example, consolidation therapy with high-dose ara-C (HDAC) with/without anthracycline drugs). If, however, the AML patient has resistant disease (about 15%) or relapses (about 70%), second remissions sometimes are achieved by treating them with conventional induction chemotherapy, high-dose ara-C (HDAC), with/without other drugs, etoposide or other single chemotherapeutic agents.

Elderly AML patients have special treatment concerns. They may be less able to tolerate the septicemia (blood poisoning) associated with granulocytopenia, and they often have higher rates of myelodysplastic ("preleukemia") syndrome (MDS). Individuals who are over age 75 or who have significant medical conditions can be treated effectively with low-dose ara-C. High-dose post-induction chemotherapy is unlikely to be tolerated by elderly patients.

Until recently, the treatment plans and responses of children with AML did not differ much from those of adults. Yet new, more intensive induction and consolidation treatments have resulted in higher remission rates and prolonged survivals. Many induction trials have produced good results using combinations of cytarabine (ara-C) plus an anthracycline (e.g., daunorubicin, doxorubicin). In children under 3 years of age, the anthracycline used for induction should be chosen with care, since doxorubicin produces more toxicity and related deaths than daunorubicin.

Consolidation therapy is complex, but it should include at least two courses of high-dose ara-C (HDAC). Children who have hyperleukocytosis (too many white blood cells), especially monocytic M5 leukemia, have a poor prognosis.

ii. Chronic Myelogenous Leukemia (CML)

The challenge of treating newly diagnosed CML is to determine the best overall strategy to control the disease.

General strategies for management include a variety of options. Leukapheresis, also known as a peripheral blood stem cell transplant, with stem cell cryopreservation (frozen storage) prior to any other treatment. The patient's blood is passed through a machine that removes the stem cells and then returns the blood to the patient. Leukapheresis usually takes 3 or 4 hours to complete. The stem cells may or may not be treated with drugs to kill any cancer cells. The stem cells then are stored until they are transplanted back into the patient.

Another choice is chemotherapy with drugs such as hydroxyurea (FHYDREA®), busulfan (MYLERAN®) or imatinib mesylate (GLEEVEC™). In general, CML treatment options are divided into two groups: those that do not increase survival and those that do. Chemotherapeutic drugs such as hydroxyurea (HYDREA®) and busulfan (MYLERAN®) can normalize the blood count for a period of time, but they do not increase survival. They often are used to control blood counts in patients who cannot undergo SCT or who do not respond to interferon therapy because of age or medical considerations.

GLEEVEC™ is one of a new class of cancer drugs that disables an abnormal enzyme in the cancerous cell, kills it, but leaves healthy cells virtually untouched. Other cancer therapies, such as chemotherapy, attack healthy cells as well as cancer cells, leaving patients with unpleasant and often severe side effects.

In June of 2006, the Food and Drug Administration (FDA) approved the oral tyrosine kinase inhibitor dasatinib (SPRYCEL™) to treat CML that does not respond to other therapy.

One treatment that does impact on CML survival is allogeneic bone marrow transplantation, the use of high dose chemotherapy and radiation followed by infusion of a donor bone marrow. This procedure removes the chromosomal abnormality in a large percentage of patients and for them is curative. In addition, there is treatment with interferon (INF). About 20% to 30% of patients taking interferon show elimination of the abnormal chromosome and improved survival. Recent findings also suggest that low-dose cytarabine (ara-C), in combination with interferon, may be more beneficial than interferon alone. For patients who do not respond to interferon, autologous or allogeneic stem cell transplantation is the only alternative.

Patients with advanced-phase disease may be treated with cytotoxic drugs. For example, individuals showing myeloid transformation may be given drugs that are used to induce remission in AML—that is, daunorubicin and cytarabine, with or without 6-thioguanine or etoposide. Blast cell numbers will be reduced temporarily, but they will increase again within 3 to 6 weeks. Individuals showing lymphoid transformation have a slightly better outlook. They are treated with drugs used in the management of acute lymphocytic leukemia (ALL)—that is, prednisone, vincristine, and daunorubicin, with or without L-asparaginase.

New drugs that are being studied in clinical trials of CML include homoherringtonine with interferon-alpha (INF-α), paclitaxel (TAXOL®), QS21 (a plant extract that heightens immune responses), and amifostin (a chemical that lessens some side effects of chemotherapy). In addition, clinical trials are evaluating the potential benefits of substances such as vaccines, monoclonal antibodies (immunologic substances that can direct the patient's immune system to kill cancer cells), and hormones (e.g., growth factors, interleukins).

iii. Acute Lymphocytic Leukemia (ALL)

Proper management of ALL focuses on control of bone marrow and systemic (whole-body) disease as well as prevention of cancer at other sites, particularly the central nervous system (CNS). In general, ALL treatment is divided into several phases.

Induction chemotherapy is designed to bring about remission—that is, leukemic cells are no longer found in bone marrow samples. For adult ALL, standard induction plans include prednisone, vincristine, and an anthracycline drug; other drug plans may include L-asparaginase or cyclophosphamide. For children with low-risk ALL, standard therapy usually consists of three drugs (prednisone, L-asparaginase, and vincristine) for the first month of treatment. High-risk children may receive these drugs plus an anthracycline such as daunorubicin.

Consolidation therapy (1-3 months in adults; 4-8 months in children) is used to eliminate any leukemia cells that are still "hiding" within the body. A combination of chemotherapeutic drugs is used to keep the remaining leukemia cells from developing resistance. Patients with low- to average-risk ALL receive therapy with antimetabolite drugs such as methotrexate and 6-mercaptopurine (6-MP). High-risk patients receive higher drug doses plus treatment with extra chemotherapeutic agents.

CNS prophylaxis (preventive therapy) stops the cancer from spreading to the brain and nervous system. Standard prophylaxis may consist of: cranial (head) irradiation plus spinal tap or intrathecal (IT) delivery (into the space around the spinal cord and brain) of the drug methotrexate; high-dose systemic and IT methotrexate, without cranial irradiation; and IT chemotherapy. Only children with T-cell leukemia, a high white blood cell count, or leukemia cells in the cerebrospinal fluid (CSF) need to receive cranial irradiation as well as IT therapy.

Maintenance treatments with chemotherapeutic drugs (e.g., prednisone+vincristine+cyclophosphamide+doxorubicin; methotrexate+6-MP) prevent disease recurrence once remission has been achieved. Maintenance therapy usually involves drug doses that are lower than those administered during the induction phase. In children, an intensive 6-month treatment program is needed after induction, followed by 2 years of maintenance chemotherapy.

Follow-up therapy for ALL patients usually consists of supportive care, such as intravenous nutrition and treatment with oral antibiotics (e.g., ofloxacin, rifampin), especially in patients with prolonged granulocytopenia; that is, too few mature granulocytes (neutrophils), the bacteria-destroying white blood cells that contain small particles, or granules (<100 granulocytes per cubic millimeter for 2 weeks) and transfusions with red blood cells and platelets.

Polymerase chain reaction (PCR) tests are advisable for ALL patients since they may help to identify specific genetic abnormalities. Such abnormalities have a large impact upon prognosis and, consequently, treatment plans. PCR testing is especially important for patients whose disease is B-cell in type. B-cell ALL usually is not cured by standard ALL therapy. Instead, higher response rates are achieved with the aggressive, cyclophosphamide-based regimens that are used for non-Hodgkin's lymphoma. Among ALL patients, 3-5% children and 25-50% of adults are positive for the Philadelphia chromosome (Ph1). Because these patients have a worse prognosis than other individuals with ALL, many oncologists recommend allogeneic bone marrow transplantation (alloBMT), since remission may be brief following conventional ALL chemotherapy.

People who receive bone marrow transplantation will require protective isolation in the hospital, including filtered air, sterile food, and sterilization of the microorganisms in the gut, until their total white blood cell (WBC) count is above 500.

Recurrent ALL patients usually do not benefit from additional chemotherapy alone. If possible, they should receive re-induction chemotherapy, followed by allogeneic bone marrow transplant (alloBMT).

Alternatively, patients with recurrent ALL may benefit from participation in new clinical trials of alloBMT, immune system agents, and chemotherapeutic agents, or low-dose radiotherapy, if the cancer recurs throughout the body or CNS.

iv. Chronic Lymphocytic Leukemia (CLL)

CLL is probably incurable by present treatments. But, fortunately, a large group of CLL patients do not require therapy. Studies suggest that people with Stage A CLL (that is, individuals who have fewer than three areas of enlarged lymphoid tissue) do not benefit from early treatment. They may, in fact, suffer drawbacks because of it. Therefore, most oncologists base CLL treatment upon both the stage and symptoms of the patient.

For example, in older patients (60+ years) who have low-risk early stage disease (Rai Stage 0) a conservative "watch and wait" approach may be taken. By contrast, older individuals with CLL-related complications or more advanced disease (Rai Stage III or IV) may benefit from chemotherapy and treatment with a corticosteroid (e.g., prednisone, prednisolone).

Corticosteroids are first-line agents for people in whom the immune system has been altered by CLL. CLL may cause autoimmune syndromes in which the patient's immune system attacks and destroys his or her own blood cells. When the red blood cells are affected, the condition is known as immunohemolytic anemia, characterized by decreased numbers of red blood cells, which may cause fatigue, dizziness, and shortness of breath. When the blood platelets are affected, it is called immune-mediated thrombocytopenia, in which a decreased numbers of platelets may lead to bleeding.

For younger patients who are experiencing symptoms, the physician may consider early chemotherapy, plus allogeneic or autologous bone marrow transplantation (alloBMT; autoBMT).

In general, the indications for treatment are falling hemoglobin or platelet count progression to a later stage of disease, painful, disease-related overgrowth of lymph nodes or spleen, lymphocyte doubling time (an indicator of lymphocyte reproduction) of fewer than 12 months.

If the patient experiences blood flow problems caused by high numbers of leukemia cells in the circulation, the physician may recommend leukapheresis, also known as apheresis, to separate out white blood cells, prior to chemotherapy. Symptoms that are related to enlargement of the lymph nodes in one area or an overgrown spleen may be treated by localized, low-dose radiotherapy, or surgical management by splenectomy (removal of the spleen). But if leukemia has invaded the lymph nodes at many different sites, total body irradiation (TBI) may be needed The chemotherapeutic plans that are used most often for CLL are combination chemotherapy with chlorambucil (Leukeran®) or cyclophosphamide (Cytoxan®) plus a corticosteroid drug such as prednisone, or single-agent treatments with nucleoside drugs such as fludarabine, pentostatin, or cladribine (2-chlorodeoxyadenisine; 2-CDA). However, such drugs usually are reserved for cases in which CLL is resistant (unresponsive to treatment) or returns after chemotherapy with chlorambucil or cyclophosphamide.

People with intermediate or advanced disease may be helped by participation in a clinical trial. At the present time, clinical trials are being conducted using immunologic compounds (e.g., interferons, monoclonal antibodies) as well as new chemotherapeutic agents (e.g., bryostatin, dolastatin 10, and PSC 83—a cyclosporine drug given with chemotherapy to overcome drug resistance).

v. Hairy Cell Leukemia (HCL)

Hairy cell leukemia is an incurable, indolent blood disorder in which mutated, partly matured B cells accumulate in the bone marrow. Its name is derived from the shape of the cells, which look like they are covered with short, fine, hair-shaped projections. Unlike any other leukemia, HCL is characterized by low white blood cell counts.

Patients with hairy cell leukemia who are symptom-free typically do not receive immediate treatment. They engage in "watchful waiting" with routine bloodwork and exams every three to six months to monitor disease progression and identify any new symptoms.

Treatment is generally considered necessary when the patient shows signs and symptoms such as low blood cell counts (e.g., infection-fighting neutrophil count below 1.0 K/µl), frequent infections, unexplained bruises, anemia, or fatigue that is significant enough to disrupt the patient's everyday life.

Patients who need treatment, which includes most newly diagnosed HCL cases, usually receive either cladribine or pentostatin, which are both in a class of chemotherapeutic drugs known as purine analogs or nucleosides. In most cases, one round of treatment will produce a prolonged remission.

Other treatments include rituximab infusion or self-injection with interferon-α. In limited cases, the patient may benefit from splenectomy (removal of the spleen). These treatments are not typically given as the first treatment for a new patient because their success rates are lower than cladribine or pentostatin.

In the short term, especially when neutrophil counts are low, an immune system hormone called granulocyte colony-stimulating factor may be taken to increase white blood cell counts. This is believed to help prevent or treat an infection. Many patients also take antibiotics until their white blood cell counts have recovered to normal levels.

vi. Hodgkin's Lymphoma

Patients with early stage disease (IA or HA) are effectively treated with radiation therapy or chemotherapy. The choice of treatment depends on the age, sex, bulk and the histological subtype of the disease. Patients with later disease (III, IVA, or IVB) are treated with combination chemotherapy alone. Patients of any stage with a large mass in the chest are usually treated with combined chemotherapy and radiation therapy.

Currently, the ABVD chemotherapy regimen is the gold standard for treatment of Hodgkin's disease. The abbreviation stands for the four drugs adriamycin, bleomycin, vinblastine, and dacarbazine. Developed in Italy in the 1970's, the ABVD treatment typically takes between six and eight months, although longer treatments may be required. Another form of treatment is the newer Stanford V regimen, which is typically only half as long as the ABVD but which involves a more intensive chemotherapy schedule and incorporates radiation therapy. However, in a randomized controlled study, Stanford V was inferior.

With appropriate treatment, over 93% of Hodgkin's lymphoma cases are curable to the point of remission. The high cure rates and long survival of many patients with Hodgkin's lymphoma has led to a high concern with late adverse effects of treatment, including cardiovascular disease and second malignancies such as acute leukemias, lymphomas, and solid tumors within the radiation therapy field. Most patients with early stage disease are now treated with abbreviated chemotherapy and involved-field radiation therapy rather than with radiation therapy alone. Clinical research strategies are exploring reduction of the duration of chemotherapy and dose and volume of radiation therapy in an attempt to reduce late morbidity and mortality of treatment while maintaining high cure rates. Hospitals are also treating those who respond quickly to chemo-therapy with no radiation.

vii. Non-Hodgkin's Lymphoma

Treatment for non-Hodgkin's lymphoma depends on the stage of the disease, the type of cells involved, whether they are indolent or aggressive, and the age and general health of the patient. Non-Hodgkin's lymphoma is often treated by a team of specialists that may include a hematologist, medical oncologist, and/or radiation oncologist. Non-Hodgkin's lymphoma is usually treated with chemotherapy, radiation therapy, or a combination of these treatments. In some cases, bone marrow transplantation, biological therapies, or surgery may be options. For indolent lymphomas, the doctor may decide to wait until the disease causes symptoms before starting treatment. Often, this approach is called "watchful waiting."

Chemotherapy and radiation therapy are the most common treatments for non-Hodgkin's lymphoma, although bone marrow transplantation, biological therapies, or surgery are sometimes used. CHOP, with rituximab added in certain circumstances, is the most commonly used combination of chemotherapy.

Rituximab is an antibody-based therapy. Ibritumomab tiuxetan (commonly known as Zevalin) and Tositumomab (Bexxar) are FDA-approved options, requiring a Nuclear Medicine facility, but only two short infusions one week apart. There is mounting evidence that more patients have long-term remission if they use radioimmunotherapy first.

Radiation therapy (also called radiotherapy) is the use of high-energy rays to kill cancer cells. Treatment with radiation may be given alone or with chemotherapy. Radiation therapy is local treatment; it affects cancer cells only in the treated area. Radiation therapy for Non Hodgkin's lymphoma comes from a machine that aims the high-energy rays at a specific area of the body. There is no radioactivity in the body when the treatment is over.

Sometimes patients are given chemotherapy and/or radiation therapy to kill undetected cancer cells that may be present in the central nervous system (CNS). In this treatment, called central nervous system prophylaxis, the doctor injects anticancer drugs directly into the cerebrospinal fluid.

Hematopoietic stem cell transplantation (HSCT), or Bone marrow transplantation (BMT) may also be a treatment option, especially for patients whose non-Hodgkin's lymphoma has recurred (come back). BMT provides the patient with healthy stem cells (very immature cells, found in the marrow, that produce blood cells), the function of which is to replace white blood cells that are damaged or destroyed by treatment with very high doses of chemotherapy and/or radiation therapy. The healthy bone marrow may come from a donor, or it may be "autologous" (marrow that was removed from the patient, stored, and then given back to the person following the high-dose treatment). Autologous transplants are preferred, as the recipient is less likely to reject the cells, the origins of which were the same entity. However, in order for an autologous transplant to be performed, certain physiological conditions must be optimal within the patient. If these conditions are not present, transplanted stem cells can come from other donors. Until the transplanted bone marrow begins to produce enough white blood cells, patients have to be carefully protected from infection due to the virtual elimination of the auto-immune system resulting from the high-intensity treatment. Without the introduction of the stem cells following the high dose treatment, the patient will not survive as the body will be unable to produce infection-fighting white blood cells. Patients usually stay in the hospital for several weeks and will be monitored for transplant rejection and overall health.

Biological therapy (also called immunotherapy) is a form of treatment that uses the body's immune system, either directly or indirectly, to fight cancer or to lessen the side effects that can be caused by some cancer treatments. It uses materials made by the body or made in a laboratory to boost, direct, or restore the body's natural defenses against disease. This approach is under close investigation. Biological therapy is sometimes also called biological response modifier therapy.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Patients and Tumor Specimens.

Samples from 43 tumors were obtained from untreated patients who underwent surgery for bladder cancer at the Urology and Nephrology Center in Mansoura, Egypt between August 1998 and April 2000. The bladder cancer tissue bank used in this study was established in 1992 and contains clinical data on all patients presenting with bladder cancer. Tumor stage and grade were defined according to UICC and WHO classification, as previously described (Muscheck et al., 2000). In all cases, tumor and adjacent non-neoplastic bladder tissue were available for the study. Prior to surgery at the Center, all patients provided written informed consent to allow any excess tissue for research studies. Human bladder cancer paraffin blocks were obtained from the Hollings Cancer Center Tumor Bank, MUSC for the immunohistochemical studies. All specimens were formalin-fixed and paraffin embedded.

Cell culture and Chemicals:

Bladder cancer cell lines T24, TSU-PR1, TCC-SUP, UMUC-3, SW780, HT-1376, 5637, J82, SCaBER, and RT4 were obtained from ATCC and cultured in RPMI 1640 with 10% fetal bovine serum (FBS). The SV-HUC immortalized, non-transformed urothelial cell line was provided Dr. Santhanam Swaminathan (University of Wisconsin) and cultured in Ham's F-12 (Gibco/Invitrogen) supplemented with 1% FBS. All cell lines were propagated at 37° C. in an atmosphere containing 5% CO2. PTXA2 and SQ29548 were purchased from Cayman Chemical Company and GR32191 was a gift from the Glaxo-Smith Kline pharmaceutical company.

Generation of Human TP Isoform Specific Anti-Peptide Antibodies.

Rabbit polyclonal antibodies were raised against peptides representing residues 329-343 of human TP-α and residues 394-407 of human TP-β. Peptides were synthesized and conjugation to BSA performed using the Imject EDC kit (Pierce). Anti-sera were assessed for reactivity by ELISA using the corresponding TP receptor peptides. The TP-α-Ab and TP-β-Ab antisera had titers of 1/15000-1/20000 and 1/5000-1/10000, respectively. The antibodies were specific, reacting only with the epitopes they were raised against, with no cross reactivity against other peptides derived from divergent regions of TP receptors. Active bleeds from the same rabbit were pooled and, after sterilization, were stored at −20° C. in the presence of 0.01% sodium azide. Antisera were further purified on Affigel 10-peptide affinity columns before use in immunohistochemistry and immunoblotting.

Immunohistochemistry and TUNEL Staining.

Antigen retrieval was done by heating in a microwave oven for 5 min on high power in 10 mM citrate, pH 6.0. Sections were washed and nonspecific binding was blocked with 10% horse serum in Tris-buffered saline (TBS) (50 mM Tris-HCl, 0.9% NaCl, pH 8.0) for 20 min, then incubated overnight at 4° C. with the TP isoform-specific primary antibodies at a 1:200 dilution in the blocking solution, anti-CD31 antibody (DAKO) was used at dilution 1:25. After overnight incubation at 4° C. followed by three 10-min washes in TBS. Immpress™ horse anti-rabbit secondary was incubated (Vector Laboratories, Burlingame, Calif.) for 45 min at room temperature. Slides were counterstained with hematoxylin. PCNA staining was done utilizing mouse monoclonal antibody against human PCNA (SantaCruz) at dilution 1:200. For TUNEL staining, sections were stained using the Situ Cell Death Detection Kit (Roche Applied Science).

Western Blot Analysis.

Tumor and normal bladder tissues were snap-frozen in liquid nitrogen within 30 minutes after the surgery. Frozen sections were stained with hematoxylin and eosin and samples identified that had at least 70% tumor cells were selected for further studies. Pulverized tissue powders were lysed in RIPA buffer (150 mM NaCl, 50 mM Tris-HCl [pH 8.0], 1% Triton X100, 0.1% SDS, 1% deoxycholate and protease inhibitor cocktail [Complete Protease Inhibitors, Roche]) for 15 minutes on ice. Equal amounts of total protein (40 µg) were resolved by 12% SDS-PAGE and subjected to Western blot analyses using ECL system (Amersham-Pharmacia). Screening Western blots for TP-α and TP-β isoform expression in bladder cancer cell lines was done using rabbit polyclonal antibodies against TP-α or TP-β (described above). SVHUC cells stably transfected with TP-α or TP-β plasmids were screened for PCNA, tubulin, GAPDH, FAK, pFAK, ERK, pERK protein (Santa Cruz) and ICAM-1 (Abcam).

Transfection of Cells with TP-α and TP-β DNA.

SV-HUC cells were grown to 80% confluence and transfected with 2 µg of pcDNA3 vector encoding either the TP-α or TP-β receptor isoforms. Transfection was performed in 6-well plates using the Fugene reagent (Roche) according to the manufacturer's instructions. After 72 hours post-transfection, cells were selected with 500 µg/ml G418 (Roche) and stable pools isolated after 14 days.

Cell Growth Assay.

SV-HUC and T24 cells were seeded at 5,000 cells per well in 96-well plates, and then treated with either compound or vehicle (ethanol) alone. The number of viable cells were quantified at the indicated time points, using the MTT (3-(4, 5-Dimethyl-2-thiazolyl)-2,5-diphenyl-2H-tetrazolium bromide thiazole blue) assay, performed in quadruplicate, according to the manufacturer's instructions (Sigma-Aldrich). Optical density (OD) was measured at wavelength of 550 nm with reference wavelength of 690 nm.

Migration and Invasion Assays.

Cell migration experiments were carried out using 8-µm pore size migration chambers (Falcon, Becton Dickinson) precoated at 4° C. overnight with fibronectin (Becton Dickinson) at a concentration of 5 µg per square centimeter in PBS. The following day, the fibronectin solution was aspirated and the migration chambers were rinsed one time with water and allowed to air dry prior to the migration experiment. Cell invasion experiments were carried out using re-hydrated 8-µm pore size invasion chambers precoated with Matrigel (Becton Dickinson). Cells at 80% confluence were trypsinized, harvested, and counted. For each condition, cells were seeded at 25,000 cells/well (T24) or 100,000 cells/well (SV-HUC) in 500 µl serum free media, then added to each migration and invasion chamber. Medium (750 µl) containing 10% serum was used as a chemoattractant in the lower chamber. Both upper and lower chambers contained the indicated compound. Cells were allowed to migrate for eight hours or invade for 24 hours at 37° C. in the presence of 5% CO2. Cells that did not migrate or invade were removed by wiping the top of the membrane with a cotton swab and the migrating and invading cells were fixed and stained with Diff-Quik per the manufacturers protocol (Dade Behring). Migrating and invading cells in 10 high power fields in each chamber were counted and the mean cell number was calculated. Each experiment was conducted in triplicate and repeated three times.

Cell Morphology and Immunofluorescence Studies.

Cell morphology and immunofluorescence analyses were performed on glass chamber slides pre-coated with 5 µg/ml fibronectin. T24 cells were seeded at low density (~4 cells/mm$^2$) in normal growth media and incubated for a period of 12 hours. For U46619, or PTXA2 treatment and solvent control, cells were incubated for another 12 hours with either U46619 (1 µM), PTXA2 (1 µM), or solvent control (water). Cells were examined using phase contrast microscopy and bright field pictures were taken. For actin cytoskeletal reorganization, cells were fixed with 2% formaldehyde for 10 minutes. After washing twice with cold PBS, cells were permeabilized with 0.1% Triton X-100. Cover slips were blocked in 2% BSA and actin distribution was examined by phalloidin staining as per the manufacturer's instructions (Molecular Probes, Eugene, Oreg.). Slides were examined using an Olympus Fluoview IX70 confocal microscope.

Determination of Cell Viability and Analysis of Apoptosis.

Cell viability was analyzed under the microscope at 200× using trypan blue staining. Flow cytometric measurements of apoptosis were as follows. After 12 hours treatment with solvent control or TP receptor antagonists, cells were washed twice in ice cold phosphate buffered saline (PBS) and resuspended in binding buffer (10 mM HEPES, 140 mM NaCl, 2.5 mM CaCl$_2$), at 1×10$^6$ cells in a 400 µl volume of binding buffer, in duplicate. Cells were incubated with 10 µl of human annexin V-phycoerythrin (PE) (BD Bioscience Inc.) for 15 min at room temperature in dark. The cells were kept on ice and analyzed with a BD FACSARIA™ flow cytometer within 1 hour after staining. The TUNEL assay was performed following the protocol of the TUNEL kit's manufacturer (Roche Diagnostics).

Xenograft Mouse Model.

TCC-SUP human bladder cancer cells or SV-HUC cells stably transfected with pcDNA3, TP-α or TP-β were used in a subcutaneous model in immunocompromised (nu/nu) mice.

TCC-SUP cells (5×10⁶ in PBS) or SV-HUC cells (5×10⁷ in Matrigel™, BD Bioscience Inc.) were injected s.c. into the right and left flanks of anesthetized mice. Tumor growth was monitored in these mice twice a week. For mice injected with TCC-SUP, GR32191 or vehicle control was administered daily (20 mg/kg) by gavage with treatment initiated 24 hrs after initial injection. Two cycles of cisplatin (single high dose (5 mg/kg) or single low dose (0.5 mg/kg)) were administrated at day 4 and day 11 post tumor cell injection.

Statistical Analysis.

Kaplan-Meier survival curves were constructed for overall mouse survival for two groups with and without over-expressed TP-β receptor protein. ANOVA was used to analyze the in vitro drug treatments and drug combination data. Data are presented as the mean±SD. For all statistical tests, a two-sided p-value<0.05 was used to reject the null hypothesis. Kaplan-Meier curves were used to describe time to tumor onset in each mouse group, and a Cox proportional hazards model was used to estimate and test for differences across treatment groups. Hazard ratios and their 95% confidence intervals were to describe rates of tumor onset and p-values used to compare tumor onset across groups. The proportional hazards assumption was tested using Schoenfeld residuals. Differences in tumor growth were assessed by comparing the slopes of tumor growth across groups based on a linear longitudinal two-stage analysis where slopes were estimated in stage 1 and compared across mice in stage 2. Linear regression coefficients were evaluated using Wald tests. Statistical analyses were performed using R statistical software and utilized the survival library.

Example 2

Results

Immunohistochemical Demonstration of TP Receptor Protein in Invasive Bladder Cancer Tissues.

Human bladder cancer samples were obtained from the HCC Tumor Bank, MUSC. All specimens were formalin-fixed and paraffin embedded. Immunohistochemistry studies were performed utilizing the PH4 polyclonal antibody that recognizes both TP-α and TP-β isoforms. Normal urothelium had low level TP expression, localized to the umbrella epithelial cells facing the lumen (FIG. 1A). In contrast, TP expression was increased in carcinoma in situ (FIG. 1B) and maintained throughout cancer progression (FIGS. 1C-D). These data are representative of 7 cases that showed the same expression pattern.

Distribution of TP Receptors in Human Bladder Cancer Cell Lines.

Figure 2:
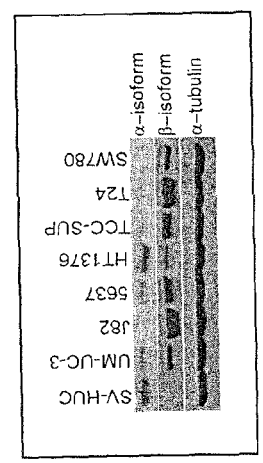
FIG. 2. TP receptor isoform expression in bladder cell lines. Isoform-specific antibodies were used in western blot analysis. Total cell lysates were prepared from the indicated bladder cell lines, resolved by SDS-PAGE and western blots were probed with anti-TP-α (top panel) or anti-TP-β (middle panel) antibodies. α-tubulin is provided as a loading control.

Because the TP receptor exists in two isoforms, its expression was determined in a series of immortalized and transformed bladder cell lines (FIG. 2). All cancer cell lines show predominant expression of the TP-β receptor protein. In contrast, immortalized non-transformed normal urothelial cells, SV-HUC, express only TP-α receptor protein. This data served to validate the specificity of the antibody.

Bladder Cancer Tissues Express Both TP Receptor Isoforms.

Figure 5:
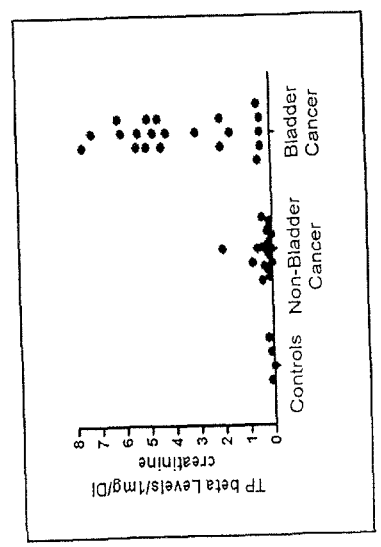
FIG. 5. Urinary TP-β receptor levels in bladder cancer patients and controls. The levels of the TP-β isoform were determined by enzyme linked immunosorbent assay (ELISA). The rabbit-TP-β-specific antibody was used as the capture antibody. 96-well plates were coated with capture antibody. Urine samples (200 ml) were added to the wells. After incubation for 2 hrs at 37° C., microplates were washed 5 times with PBST, then the rat anti-TP detection antibody was added for 30 min at RT, then washed and goat anti-rat HRP were added. After incubation for 30 min at RT, plates were washed again for 5 times and chromogenic substrate was added. After color development for 30 min at RT in dark, absorbance at 450 nm was measured using microplate reader.

The initial Northern and Western blot studies did not distinguish between the TP receptor isoforms. Using TP receptor isoform-specific antibody, the inventors evaluated the expression of TP isoforms protein in bladder cell lines (FIG. 2). Interestingly, TP-α is the predominant isoform in the immortalized, non-transformed SV-HUC cell line. In contrast, TP-β is predominant in the bladder cancer derived cell lines. Based upon these results, they performed IHC studies using these isoform-specific antibodies to determine whether both protein isoforms are expressed in bladder tissue and cancer (FIG. 5). While TP-α and TP-β are both expressed in normal tissue, TP-β is the predominant isoform expressed in cancer.

Expression of TP-β Receptors in Bladder Cancer Patients.

Figure 4:
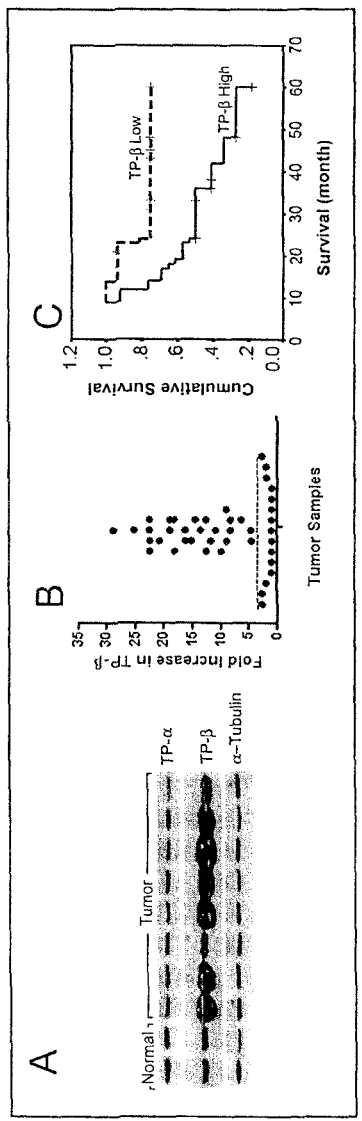
FIGS. 4A-C. Expression of TP receptors and cumulative survival in patients with bladder cancer.

Because the inventors found an increased expression of the TP-β receptor isoform in bladder cancer cell lines, they decided to determine the level of expression of the receptor in tissues previously obtained from patients with bladder cancer for whom they already had outcome data. TP receptor protein expression was evaluated by western analysis of protein prepared from tumor and non-tumor matched pairs. Using TP receptor isoform specific antibodies, the inventors assessed the level of expression of the receptors in bladder cancer tissue (FIG. 4A). An arbitrary cutoff of 3-fold increase in TP-β expression was defined as a high expression subject. The TP-β protein level is elevated in the tumor tissue extracts from 65% (n=28 out of 43) of the samples examined (FIG. 4B). There was a statistically significant (p<0.005) poor survival for the TP-β high versus TP-β low patients (FIG. 4C). No such association existed with the TP-α isoform (data not shown).

Urinary TP-β Receptor Protein Excretion in Patients with Bladder Cancer and Control Subjects.

Since the inventors found an increased expression of the TP-β receptor in the patients with bladder cancer, they sought to determine if they could find an increased level of the protein in urine. Urine samples previously collected from patients and controls were assayed for the presence of the receptor using an ELISA assay. TP-β protein levels were significantly (p<0.05) increased in the patients with bladder cancer compared to those patients who either had bladder cancer in the past or some other urological disorder (FIG. 5). In contrast there was no significant increase in urinary TP-α protein levels (data not shown). These results mirror the data obtained in cell lines and tissue samples.

TP Receptor Antagonists Reduce the Growth, Migration and Invasion of Bladder Cancer Cells.

T24 and TCC-SUP human bladder cancer cell lines treated with TP receptor antagonists showed reduced cell growth and reduced cell migration and invasion. In contrast, treatment with the receptor agonist significantly stimulated cell migration, and invasion (Moussa et al., 2005).

The inventors have performed complementary studies demonstrating 65% inhibition of cell migration and invasion by the TP receptor antagonist, GR32191 (GR) (data not shown). GR has been utilized for over a decade for studies examining the role of TP signaling in platelet aggregation (Watts et al., 1989) and vascular disease in patients (Humphrey et al., 1990). Its pharmacodynamics have been studied and has an excellent safety profile (Thomas & Lemley, 1990; Finnerty et al., 1991).

ERK and FAK Phosphorylation are Modulated by Receptor Antagonist and Agonist Treatments.

Focal adhesion kinase (FAK) is a non-receptor tyrosine kinase that mediates downstream signals from receptors for matrix proteins and growth factors. It has been implicated in cell migration, invasion, proliferation and apoptosis, and is a regulator of both assembly and disassembly of focal contacts (Wozniak et al., 2004; Schlaepfer et al., 2004; Mitra et al., 2005). FAK is often over-expressed as tumors become invasive and metastatic and attenuation of the FAK signaling pathway causes tumor cells to lose their adhesive properties and become apoptotic. Both FAK and the extracellular signal-regulated kinase/activated mitogen-activated protein kinase (ERK/MAPK) signaling pathways are required for efficient cell migration. Specifically, FAK regulates the integrin-mediated adhesive and migratory properties of tumor cells, acting in part by modulating RhoA activity, and FAK is implicated in ERK and PI3-kinase activation. Furthermore, FAK siRNA-treated cells have reduced migration and colony formation (Han et al., 2004).

Figure 6:
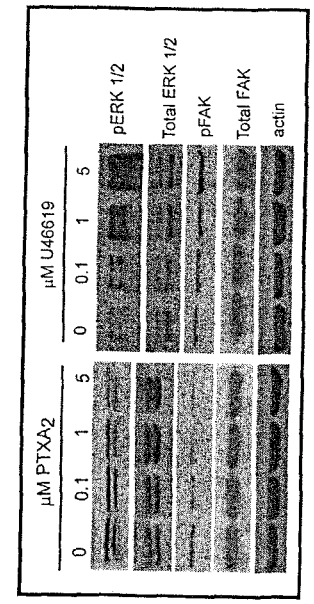
FIG. 6. Effect of TP receptor agonist (U46619) and antagonist (PTXA2) treatment on phosphorylation of FAK and ERK. T24 cells were serum starved for 12 hrs then treated with PTXA2 or U46619 for 1 hr. Tyrosine phosphorylation of FAK was assessed with western blot analysis on 30 mg of cell lysate using anti-FAK pY397 (BD Bioscience) and pERK using a pERK specific antibody.
Figure 7:
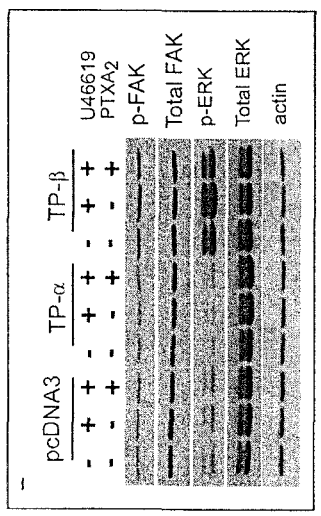
FIG. 7. Effects of U46619 and PTXA2 on phosphorylation of ERK and FAK. SV-HUC cells transfected with pcDNA3, TP-α or TP-β data are representative of 3 experiments. U46619 failed to stimulate p-ERK1/2 or pFAK in cells transfected with pcDNA3 or TP-α. U46619 stimulated pERK1/2 and pFAK in cells transfected with TP-β and the increase was blocked by PTXA2.

Based upon the effects of receptor antagonists and agonists on cell migration (Moussa et al., 2005), the inventors examined whether such treatments modulated ERK and FAK phosphorylation. Incubation of T24 cells with the TP receptor antagonist PTXA2 was associated with a reduction in the elevated basal levels of phospho-ERK and phospho-FAK (FIG. 6) and the agonist U46619 significantly increased ERK and FAK phosphorylation (FIG. 6). Significantly, they did not detect any alterations with similar treatments of the immortalized, non-transformed cell line, SV-HUC (TP-α expressor), suggesting that cancer cells may have acquired a unique dependence on TXA2 signaling (FIG. 7 and data not shown). These studies collectively implicated the TP-β receptor as playing a role in the pathophysiology of bladder cancer cells.

To further explore the role of the TP-β receptor isoform in conferring the cancer phenotype in cells, the inventors transfected SV-HUC cells with cDNA for TP-β, TP-α or pcDNA3. The TP receptor agonist U46619 stimulated the phosphorylation of FAK and ERK in the cells transfected with TP-β but not TP-α or pcDNA3 (FIG. 7). Interestingly, the TP receptor antagonist PTXA2 decreased the basal levels of pFAK and pERK in the TP-β transfected cells but not in the TP-α or pcDNA3 cells (data not shown).

TP-β Induced Cellular Transformation In Vivo.

Figure 8:
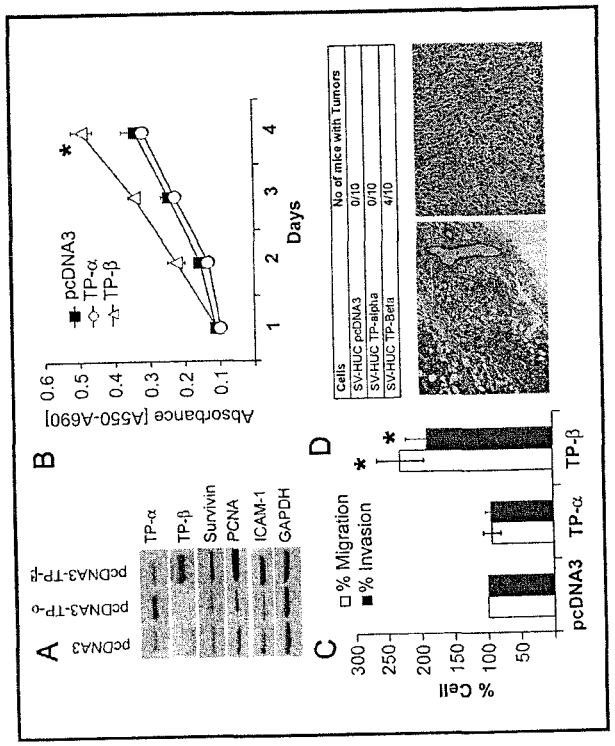
FIGS. 8A-D. Biological effects of TP receptor isoforms in bladder cells. SV-HUC cells were transfected with TP-α, TP-β or pcDNA3 vector DNA and G418 resistant stable pooled clones were selected.

Transfection of TP-β into SV-HUC cells increased the expression of proliferative cellular nuclear antigen (PCNA), intercellular adhesion molecule-1 (ICAM-1) and the anti-apoptotic gene survivin (FIG. 8A). The growth rate, migration, and invasion were observed in SV-HUC cells expressing TP-β are each is higher compared to SV-HUC cells transfected with pcDNA3 vector alone or TP-α-pcDNA3 (FIGS. 8B and 8C).

Since it appeared that the TP-β-SV-HUC cells possessed some of the biochemical phenotypes of bladder cancer cells, the inventors sought to determine if they had tumorigenic potential in vivo. TP-β-SV-HUC cells, TP-α-SVHUC cells or pcDNA-SV-HUC cells ($5 \times 10^6$ cells) were injected subcutaneously into nu/nu mice (n=10 per group). No tumors were found in the mice injected with the TP-α-SV-HUC cells or pcDNA-SV-HUC cells. However, 4 of the 10 mice injected with the TP-β-SV-HUC cells developed tumors.

Figure 9:
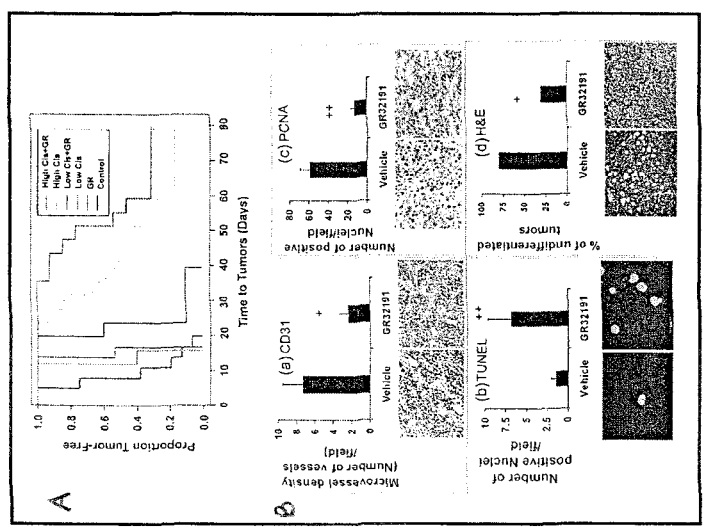
FIGS. 9A-B. TP receptor antagonist inhibits bladder cancer tumor growth.

TP receptor antagonists modulate the growth of bladder cancer cells in vivo. To initiate these studies, TCC-SUP human bladder cancer cells were used in a subcutaneous (s.c.) model in immunocompromised (nu/nu) mice. TCC-SUP cells ($5 \times 10^6$ in PBS) were injected s.c. into the right and left flanks of anesthetized mice. GR32191 or vehicle control (PBS) was administered daily (20 mg/kg) by gavage with treatment initiated 24 hrs after initial injection. Detection of palpable tumors was delayed in mice treated with GR32191. Tumor growth was monitored in these mice over time and, tumor growth was significantly inhibited in GR treated mice (FIG. 9A). In addition, the time of tumor free mice was significantly (P<0.04) extended in the GR treated group. To further characterize the tumors derived from vehicle treated mice versus GR32191 treated mice, immunohistochemical analysis and H&E staining was performed to assess the phenotypes of the tumor. There was a significantly higher percentage (p<0.01) of undifferentiated tumors detected by H&E staining of the tumors xenografts (FIG. 9B-d), and significantly increased (p<0.05) cell proliferation as indicated by Proliferating Cell Nuclear Antigen (PCNA) staining in vehicle treated mice (FIG. 9B-c) compared to GR32191 treated mice. There was a significantly higher (p<0.05) microvessel density (MVD), measured by staining with the endothelial marker CD31 in tumors derived from mice treated with vehicle control compared to mice treated with GR32191 (FIG. 9B-a). In contrast, a significant increase in apoptosis (TUNEL staining, p<0.05) was observed in tumors derived from mice treated with GR32191 (FIG. 9B-b) compared to vehicle treated mice. Thus, the reduced tumor growth observed following treatment with TP receptor antagonist was due to decreased proliferation, increased apoptosis and diminished angiogenesis. The tumors have been harvested and cell lines are being created from them. These observations further support the notion that signaling via the TP-β receptor has the potential to contribute to a cancer phenotype.

TP Receptor Antagonists and Cisplatin and Paclitaxel Sensitivity.

The inventors determined that treatment of T24 cells with TP receptor antagonists, GR32191 and SQ29,548, enhanced sensitivity to cisplatin. In addition, they found that receptor antagonists synergize with to enhance cell death (data not shown). Significantly, GR32191 prolonged survival alone or in combination with cisplatin (FIG. 9A). Collectively, these observations support the use of combination therapy with standard chemotherapies in vivo.

Expression of TP-β Receptors in Genitourinary Derived Cancer Cell Lines.

Figure 10:
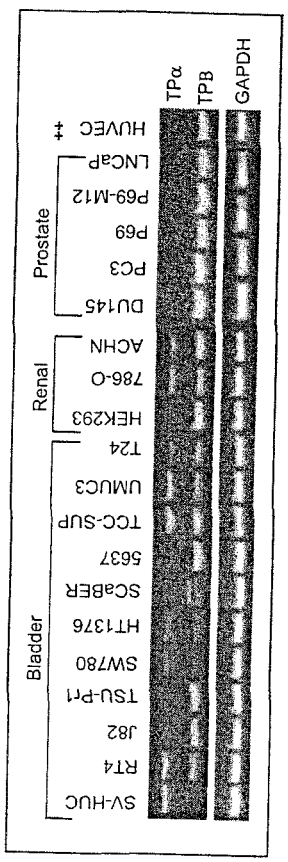
FIG. 10. Expression of TP receptors isoforms in genitourinary tumors derived cell lines. RT-PCR analysis was performed on total RNA extracted from various GU derived cell lines. PCR primers that distinguish between the two isoforms based on amplicon size were utilized.

Since the inventors found that the TP-β receptor was overexpressed in the bladder cancer cell lines and TP receptor antagonists have been reported to decrease the growth of other cancer cell lines, they sought to determine if the TP-β receptor is specifically overexpressed in other cancer cell lines. As can be seen in FIG. 10, TP-β receptors were expressed in all of the cancer cell lines analyzed. Thus, it would appear that the expression of TP-β in cancer cells may be a fairly common phenomenon and contribute to the cancer phenotype. These observations collectively raise the possibility that TP receptor antagonists may be useful, safe adjuncts to cancer chemotherapy regimens.

Expression of G Proteins in Bladder Cancer Cell Lines.

Figure 11:
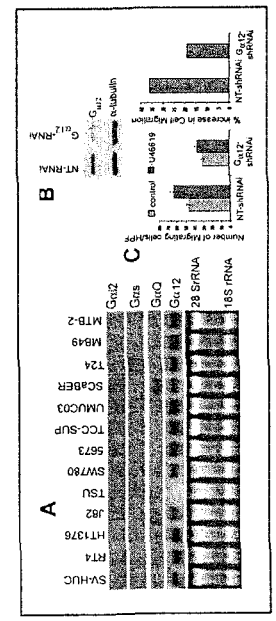
FIGS. 11A-C. Expression of the Gα proteins in bladder cells.

Since the inventors postulated that some of the oncogenic effects of TP-β are via G proteins, they performed Western blot analysis for the major G proteins that TP-β signals through and found that the predominant G protein expressed was $G_\alpha 12$ (FIG. 11). To determine if $G_\alpha 12$ played a role in migration, the cells were treated with shRNAi for $G_\alpha 12$ or NT (no-target) shRNAi. U46619 stimulated migration was significantly reduced by shRNAi for $G_\alpha 12$ (FIG. 11).

Expression of β-Arrestins in Bladder Cancer Cell Lines.

Figure 12:
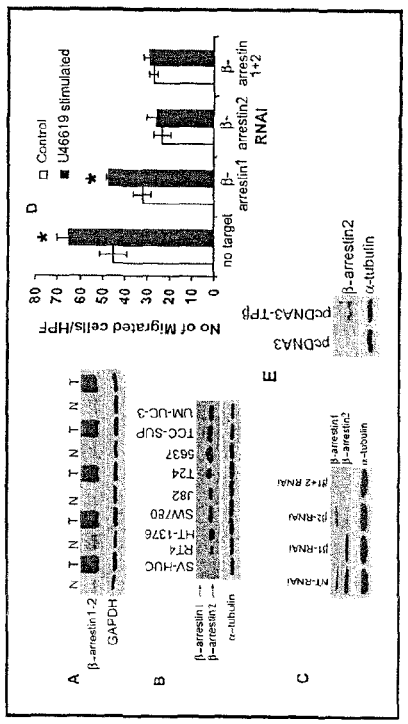
FIGS. 12A-E. Expression of β-arrestins in bladder tumors and cell lines.

To determine whether non-G protein dependent signaling of the TP-β receptor is via β-arrestins, the inventors first examined the distribution of β-arrestin-1 and/or -2 expression in human bladder normal and malignant tissues, and bladder cell lines. In matched tumor/normal tissues obtained from bladder cancer patients, β-arrestin-2 is highly over expressed in tumor tissues compared to the normal tissues (FIG. 12A). β-arrestin-2 was highly expressed in the bladder cancer cell lines, in contrast to immortalized non-transformed cells SV-HUC cells (FIG. 12B). To determine if β-arrestin-1 or -2 played a role in migration, T-24 cells were treated with shRNAi specific for β-arrestin-1 or -2 or NT-shRNAi control (specificity shown in FIG. 12C). ShRNAi for β-arrestin-2, but not -1, inhibited the increase in migration induced by U46619 (FIG. 12D). Significantly, the inventors found that β-arrestin-2 level is increased by expression of TP-β receptor in SV-HUC cells (FIG. 12E).

TP-β Receptor Binding Partners and Genes Altered by its Expression.

Although the TP-β receptor is reported to regulate the expression of several cancer associated genes such as the apoptosis related protein 14-3-3 (Yan et al., 2006), and metastases promoting gene, plasminogen activator inhibitor 1 (PAI1) (Davi et al., 1996; Fitzgerald and Fitzgerald, 1989), there were not any reports about the target genes regulated by TP-β in tumor cells. TP-β receptor signaling is also regulated by its binding partner such as the regulation by binding to the metastases suppressor protein NM23 (Rochdi et al., 2004). For this study, the inventors utilized a global approach using cDNA microarrays to identify gene that are altered by TP-β expression. Among the genes identified was the anti-apoptotic gene survivin and the pro-angiogenesis, pro-metastatic gene pleiotrophin. The inventors also utilized a novel approach using Protein-Protein-Interaction (PPI) system (Invitrogen) to identify the TP-β binding partners. PTEN genes were identified as a binding partner of TP-β.

TP-β and PTEN.

Figure 13:
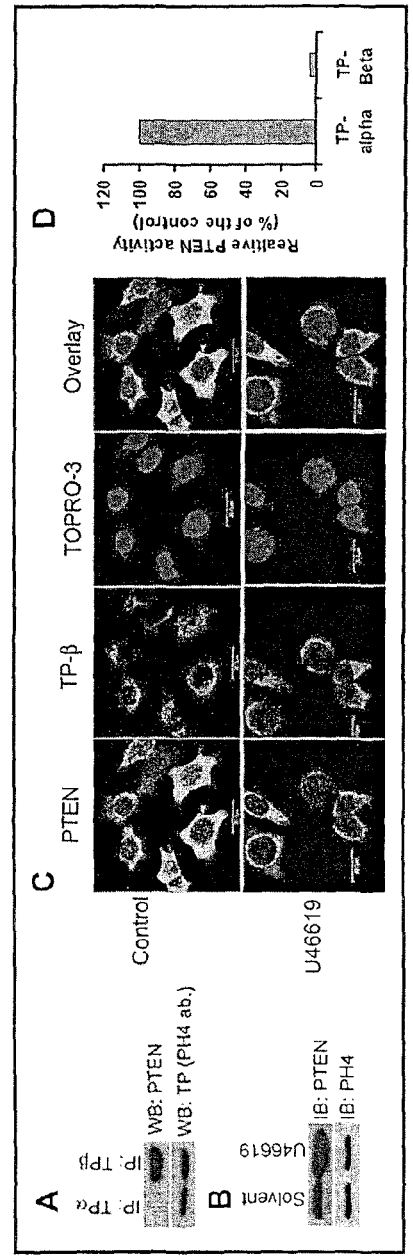
FIGS. 13A-D. TP-β receptor localization and interaction with PTEN.

Since PTEN is a tumor suppressor gene, the inventors sought to confirm if TP receptors interaction with PTEN and to examine whether TP-β receptor expression would alter the activity of PTEN. Cell lysates prepared from HT-1376 (wild-type PTEN) were incubated with TP-β specific antibody and PTEN was found to coimmunoprecipitate with TP-β (FIG. 13A). This interaction was enhanced in the presence of agonist (FIG. 13B). TP-β co-localized with PTEN in the cytoplasm and in the presence of U46619, the TP-β and PTEN proteins translocated to the nuclear membrane (FIG. 13C). Significantly, the activity of PTEN measured after immunoprecipitation was found to be significantly decreased in the SV-HUC cells transfected with TP-β, but not TP-α (FIG. 13D).

TP-β and Pleiotrophin.

Figure 14:
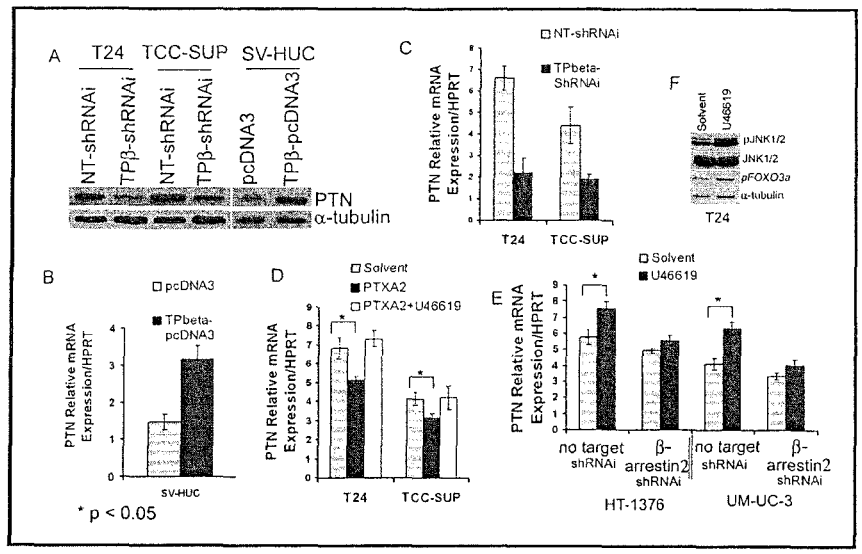
FIGS. 14A-F. TP-β regulation of pleiotrophin (PTN).
Figure 15:
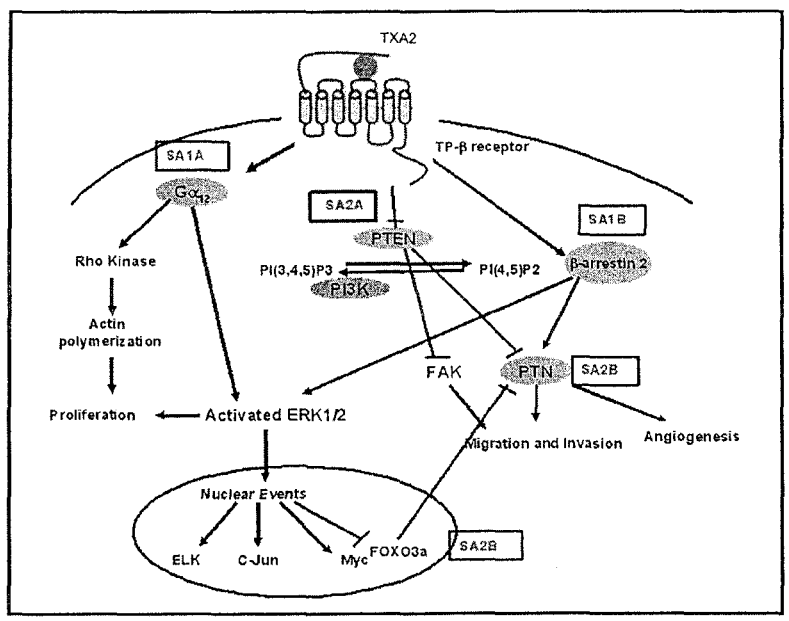
FIG. 15. Proposed model for the TP-β receptor signaling pathways resulting in a malignant phenotype. The arrows signify the integration of the specific aims and which components of the TP-β signaling pathways will be investigated. These pathways will be explored to determine their potential roles in proliferation (anti-apoptosis), migration, invasion and metastatic potential. The diagram provides a working hypothesis and does not encompass all the possible signaling molecules, proteins and genes that may mediate the oncogenic potential of TP-β.

One of the downstream molecules regulated by PTEN is Pleiotrophin (PTN). PTN expression has been linked to increased angiogenic potential of cancer (Perez-Pinera et al., 2007). Secretion of this growth factor is also linked to tissue remodeling and increased metastatic potential of breast cancer (Chang et al., 2007). The inventors' preliminary cDNA microarray analyses indicated that PTN mRNA levels was increased following TP-β expression. Subsequent loss of function (TP-β-shRNAi) and gain of function (TP-β-expression) studies support the model that PTN mRNA and protein are regulated by TP-β expression (FIGS. 14A-C), which suggests a role of TP-β in the transcription regulation of PTN. Incubation with receptor antagonist PTXA2 reduced PTN mRNA expression and PTN expression was restored by co-incubation with the receptor agonist U46619 (FIG. 14D). Agonist-dependent PTN mRNA increase was dependent upon β-arrestin-2 (FIG. 14E). Collective results in multiple cell lines also indicate that TP-β regulation of PTN is independent PTEN status. Furthermore, agonist stimulation with U46619 induced JNK1/2 activation, and reduced the expression of the transcription factor FOXO3a (FIG. 14F).

Summary.

Although a role for G protein coupled receptors (GPCRs) in tumor progression has been reported, to the inventors' knowledge, these data are the first to demonstrate the direct association between GPCR activation and in vivo malignant transformation and also its direct interaction with a tumor suppressor gene (PTEN). Of major significance was the observation is that this GPCR alone was able to transform primary cells. These findings, coupled with the up-regulation of the TP-β in several human cancers, and its correlation with disease progression, metastasis potential and overall bladder cancer patients' survival make it an ideal candidate for mechanistic studies and therapeutic intervention. Thromboxane receptor antagonists have been in clinical trials for cardiovascular disease and have excellent safety profiles, raising the possibility of using them as adjunct therapy in a clinical trial for bladder cancer. The inventors have further demonstrated that TP-β receptor overexpression is correlated with shortened patient survival, providing the basis for examining the possible correlation between TP-β receptor expression and urinary TP-β receptor protein excretion with prognosis and outcome in patients with bladder cancer.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

U.S. Pat. No. 4,196,265
U.S. Pat. No. 4,243,671
U.S. Pat. No. 4,313,734
U.S. Pat. No. 4,366,241
U.S. Pat. No. 4,632,901
U.S. Pat. No. 4,770,853
U.S. Pat. No. 4,786,589
U.S. Pat. No. 4,816,567
U.S. Pat. No. 4,867,973
U.S. Pat. No. 5,091,191
U.S. Pat. No. 5,128,359
U.S. Pat. No. 5,158,967
U.S. Pat. No. 5,280,034
U.S. Pat. No. 5,565,332
U.S. Pat. No. 5,597,848
U.S. Pat. No. 5,618,941
U.S. Pat. No. 5,656,448
U.S. Pat. No. 5,955,370
U.S. Pat. No. 6,136,801
U.S. Pat. No. 6,297,020
U.S. Publication. 2006/0217431
U.S. Patent Publication 2008/0286825
U.S. Ser. No. 12/253,592
Becker et al., *Biochim. Biophys. Acta*, 1450:288-296, 1999.
Blochl-Daum et al., *Clin. Pharmacol. Therap.*, 58:418-424, 1995.
Bokemeyer et al., *World J. Urol.*, 16:155-162, 1998.
Buchanan et al., *Proc. Natl. Acad. Sci.*, 103:1492-1497, 2006.
Calabro and Sternberg, *Curr. Opin. Urol.*, 12:441-448, 2002.
Campbell, In: *Monoclonal Antibody Technology, Laboratory Techniques in Biochemistry and Molecular Biology*, Burden and Von Knippenberg (Eds.), Elseview, Amsterdam, 13:71-74/75-83, 1984.

Casey et al., *Endocr. Pathol.*, 15:107-116, 2004.
Chang et al., *PNAS USA* 104:10888-10893, 2007.
Chen et al., *Science*, 301:1394-1397, 2003.
Coyle and Kinsella, *FEBS J.*, 272:1036-1053, 2005.
Davi et al., *Thromb. Haemost.* 76:34-37, 1996.
European Appln. EP-A 0 125 118
European Appln. EP-A 0 143 574
European Appln. EP-A 0 282 192
European Appln. EP-A 0 299 428
Finnerty et al., *Thorax,* 46:190-192, 1991.
Fitzgerald et al., *Fed. Proc.*, 46:154-158, 1987.
Fitzgerald & Fitzgerald, *PNAS USA* 86:7585-7589, 1989.
Fujimura et al., *J. Cancer Res. Clin. Oncol.*, 125:389-394, 1999.
Gao et al., *J. Pharmacol. Exp. Ther.*, 296:426-33, 2001.
Gefter et al., *Somatic Cell Genet.*, 3:231-236, 1977.
Goding, In: *Monoclonal Antibodies: Principles and Practice*, 2d ed., Academic Press, Orlando, Fla., pp 60-61, 71-74, 1986.
Halushka et al., *Annu. Rev. Pharmacol. Toxicol.*, 29:213-239, 1989.
Halushka et al., In: *Handbook of Experimental Pharmacology, Platelets and Their Factors*, Vol. 126, Von Bruchhusen and Walter (Eds.), 459-482, Springer-Verlag, Berlin, Germany, 1997.
Halushka, *Prostaglandins Other Lipid Mediators,* 60:175-189, 2000.
Han et al., *Anticancer Res.* 24:3899-3905, 2004.
Harlow and Lane, In: *Antibodies: A Laboratory Manual*, Cold Spring Harbor Laboratory, 1988.
Hirata et al., *J. Clin. Invest.*, 94:1662-1667, 1994.
Hirata et al., *J. Clin. Invest.*, 97:949-956, 1996.
Hirata et al., *Nature,* 349:617-620, 1991.
Huang et al., *Cell. Signal.*, 16:521-533, 2004.
Humphrey et al., *Circulation,* 81, 142-52; 159-60, 1990.
Jabbour et al., *Molec. Cell. Endocrin.*, 252:191-200, 2006.
Jariyawat et al., *Biochem. Mol. Biol. Int.*, 42:113-121, 1997.
Jemal et al., *CA Cancer J. Clin.*, 57:43-66, 2007.
Kelley-Hickie and Kinsella, *Biochim. Biophys. Acta,* 1761: 1114-1131, 2006.
Kohler and Milstein, *Eur. J. Immunol.,* 6:511-519, 1976.
Kohler and Milstein, *Nature,* 256:495-497, 1975.
Miggin and Kinsella, *Biochim. Biophys. Acta,* 1425:543-559, 1998.
Miggin and Kinsella, *Mol. Pharm.,* 61:817-831, 2002.
Mitra et al., *Nat. Rev. Mol. Cell Biol.* 6:56-68, 2005.
Moussa et al., *Cancer Res.,* 65:11581-11587, 2005.
Muscheck et al., *Carcinogenesis,* 21:1721-176, 2000.
Nagata et al., *Am. J. Physiol.,* 263:H1331-H1338, 1992.
Needleman et al., *Science,* 193:163-165, 1976.
Nie et al., *Am. J. Pathol.,* 164:429-439, 2004.
Onguru et al., *Endocr. Pathol.,* 15:17-27, 2004.
Parent et al., *J. Biol. Chem.,* 274:8941-8948, 1999.
Parent et al., *J. Biol. Chem.,* 276:7079-7085, 2001.
Perez-Pinera et al., *Cell Cycle* 6:2877-2883, 2007.
PCT Appln. WO 88/08534
Raychowdhury et al., *J. Biol. Chem.,* 269:19256-19261, 1994.
Remuzzi et al., *Kidney Internatl.*, 41:1483-1493, 1992.
Rochdi et al., *J. Biol. Chem.*, 279:18981-18989, 2004.
Schlaepfer et al., *Biochim. Biophys. Acta* 1692:77-102, 2004.
Sengupta and Blute, *J. Urol.*, 67(Suppl. 3A):48-55, 2006.
Shenker et al., *J. Biol. Chem.*, 266:9309-9313, 1991.
Takekoshi et al., *J. Biochem.*, 130, pp. 299-303, 2001.
Theriault et al., *Biochemistry,* 43:5600-5607, 2004.
Thomas & Lumley, *Circulation* 81, 153-8; 159-60, 1990.
Valentin et al., *Biochem. Biophys. Res. Comm.*, 329:898-904, 2005.
Wardemann et al. *Science,* 301(5638):1374-1377, 2003.
Watts et al., *Br. J. Pharmacol.* 98(supp):842P, 1989.
Wozniak et al., *Biochim. Biophys. Acta* 1692:103-119, 2004.
Winston and Safirstein, *Am. J. Physiol.*, 249:F490-496, 1985.
Yan et al., *Biochem. Pharmacol.* 71:624-633, 2006.
Yoshimoto et al., *Oncol. Rep.*, 13:1049-1057, 2005.

The invention claimed is:

1. A method of treating genitourinary cancer or pancreatic cancer in a subject comprising:
    (a) assessing thromboxane receptor β (TP-β) expression in a genitourinary or pancreatic cancer cell or urine sample from said subject; and
    (b) administering to said subject a TP-β antagonist and/or a thromboxane synthase (TXAS) inhibitor if TP-β expression in said genitourinary cancer cell or urine sample is elevated as compared to an appropriate control cell or sample.

2. The method of claim 1, wherein said genitourinary cancer cell is a a bladder cancer cell, a prostate cancer cell, a kidney cancer cell, a testicular cancer cell or a urethral cancer cell.

3. The method of claim 1, wherein step (b) comprises administering said TP-β antagonist.

4. The method of claim 1, wherein step (b) comprises administering said TXAS inhibitor.

5. The method of claim 1, wherein step (b) comprises administering both said TP-β antagonist and said TXAS inhibitor or compounds that have both actions as TP receptor antagonist and TXAS inhibitor within a single molecular entity.

6. The method of claim 1, wherein step (a) comprises immunohistochemistry, ELISA, RIA, or Western blot.

7. The method of claim 1, further comprising assessing TP-β expression from said control cell or sample.

8. The method of claim 7, wherein said control cell is a non-cancer cell obtained from said subject.

9. The method of claim 1, further comprising administering to said subject a second anti-cancer therapy.

10. The method of claim 9, wherein said second anti-cancer therapy is chemotherapy, radiotherapy, toxin therapy, gene therapy, surgery, targeted therapy using small molecules or immunotherapy.

11. The method of claim 1, wherein said genitourinary pancreatic cancer is recurrent, metastatic or multi-drug resistant.

12. The method of claim 1, wherein said subject is a human.

13. The method of claim 1, wherein said subject is a non-human mammal.

14. The method of claim 1, further comprising obtaining said genitourinary or pancreatic cancer cell or urine sample from said subject.

15. The method of claim 1, wherein administering comprises intravenous, intra-arterial, subcutaneous, intratumoral, oral, topical, intraperitoneal or aerosol delivery.

16. A method of treating a genitourinary (GU) cancer or pancreatic cancer in a subject comprising administering to said subject (a) a thromboxane receptor β (TP-β) antagonist and/or a thromboxane synthase (TXAS) inhibitor and (b) a second anti-cancer therapy, wherein said GU or pancreatic cancer cells in said subject exhibit elevated TP-β expression as compared to an appropriate control cell.

* * * * *

UNITED STATES PATENT AND TRADEMARK OFFICE
CERTIFICATE OF CORRECTION

PATENT NO. : 8,551,489 B2
APPLICATION NO. : 12/811321
DATED : October 8, 2013
INVENTOR(S) : Omar Moussa et al.

Page 1 of 1

It is certified that error appears in the above-identified patent and that said Letters Patent is hereby corrected as shown below:

In the Claims:

In claim 11, column 62, line 46, after "genitourinary" insert --or--.

Signed and Sealed this
Fifth Day of August, 2014

Michelle K. Lee
*Deputy Director of the United States Patent and Trademark Office*